United States Patent
Ito

(10) Patent No.: US 11,700,767 B2
(45) Date of Patent: Jul. 11, 2023

(54) CONDENSED CYCLIC COMPOUND, COMPOSITION INCLUDING THE CONDENSED CYCLIC COMPOUND, AND ORGANIC LIGHT-EMITTING DEVICE INCLUDING THE COMPOSITION

(71) Applicant: SAMSUNG ELECTRONICS CO., LTD., Suwon-si (KR)

(72) Inventor: Mitsunori Ito, Kanagawa (JP)

(73) Assignee: SAMSUNG ELECTRONICS CO., LTD., Gyeonggi-Do (KR)

(*) Notice: Subject to any disclaimer, the term of this patent is extended or adjusted under 35 U.S.C. 154(b) by 543 days.

(21) Appl. No.: 16/217,194

(22) Filed: Dec. 12, 2018

(65) Prior Publication Data
US 2019/0189931 A1 Jun. 20, 2019

(30) Foreign Application Priority Data

Dec. 20, 2017 (JP) .................................. 2017-244291
Jun. 29, 2018 (KR) ........................ 10-2018-0076110

(51) Int. Cl.
*C07D 405/14* (2006.01)
*H10K 85/60* (2023.01)
(Continued)

(52) U.S. Cl.
CPC ....... *H10K 85/6572* (2023.02); *C07D 405/14* (2013.01); *C07D 409/14* (2013.01);
(Continued)

(58) Field of Classification Search
None
See application file for complete search history.

(56) References Cited

U.S. PATENT DOCUMENTS 8,895,966 B2 11/2014 Numata et al.
9,647,217 B2 5/2017 Lin et al.
(Continued)

FOREIGN PATENT DOCUMENTS

CN 104829626 A 8/2015
CN 107226811 A 10/2017
(Continued)

OTHER PUBLICATIONS

Gilman, H. Journal of the American Chemical Society, 1934, 1415-1416.*
(Continued)

*Primary Examiner* — Clinton A Brooks
(74) *Attorney, Agent, or Firm* — Cantor Colburn LLP

(57) ABSTRACT

A condensed cyclic compound represented by Formula 1 and including 9 to 60 aromatic rings:

$$(A)_{\overline{n}}-L \qquad \text{Formula 1}$$

A is a group represented by Formula 10, n is selected from 1, 2, 3, and 4, L is hydrogen, a single bond or a linking group, and when n is 1, p is selected from 1, 2, 3, and 4, and q is selected from 1, 2, 3, and 4, (Continued)

US 11,700,767 B2

Page 2

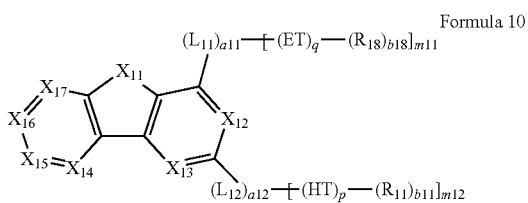

Formula 10 wherein Formula 10 is the same as described in the specification.

7 Claims, 1 Drawing Sheet

(51) Int. Cl.
  C09K 11/06      (2006.01)
  C07D 409/14     (2006.01)
  H10K 50/11      (2023.01)
  H10K 50/15      (2023.01)
  H10K 50/16      (2023.01)
  H10K 50/17      (2023.01)
  H10K 50/18      (2023.01)
  H10K 101/10     (2023.01)

(52) U.S. Cl.
  CPC .......... C09K 11/06 (2013.01); H10K 85/654 (2023.02); H10K 85/6574 (2023.02); *C09K 2211/1018* (2013.01); *H10K 50/11* (2023.02); *H10K 50/15* (2023.02); *H10K 50/16* (2023.02); *H10K 50/17* (2023.02); *H10K 50/171* (2023.02); *H10K 50/18* (2023.02); *H10K 2101/10* (2023.02)

(56) References Cited

U.S. PATENT DOCUMENTS

| | | |
|---|---|---|
| 2009/0030202 A1 | 1/2009 | Iwakuma et al. |
| 2015/0228909 A1 | 8/2015 | Kim et al. |
| 2015/0333272 A1 | 11/2015 | Ozeki et al. |
| 2016/0056393 A1 | 2/2016 | Oikawa et al. |
| 2016/0111657 A1 | 4/2016 | Lee et al. |
| 2016/0315259 A1 | 10/2016 | Fennimore et al. |
| 2017/0194570 A1 | 7/2017 | Kang et al. |
| 2017/0194574 A1 | 7/2017 | Ishidai et al. |
| 2017/0213988 A1 | 7/2017 | Park et al. |
| 2018/0037546 A1 | 2/2018 | Sugino et al. |
| 2018/0072945 A1 | 3/2018 | Otsu et al. |
| 2018/0287072 A1 | 10/2018 | Park et al. |

FOREIGN PATENT DOCUMENTS

| | | | | |
|---|---|---|---|---|
| JP | 2012028548 A | 2/2012 | | |
| JP | 2013069905 A | 4/2013 | | |
| JP | 2013110262 A | 6/2013 | | |
| JP | 2014-116454 A | 6/2014 | | |
| JP | 2014116454 | * | 6/2014 | ............. C09K 11/06 |
| JP | 2014-179493 A | 9/2014 | | |
| JP | 2016149473 A | 8/2016 | | |
| KR | 2013-0057416 A | 5/2013 | | |
| KR | 2014-0020208 A | 2/2014 | | |
| KR | 2015-0100493 A | 9/2015 | | |
| KR | 1020170013152 A | 2/2017 | | |
| KR | 1020170057660 A | 5/2017 | | |
| KR | 2017-0082126 A | 7/2017 | | |
| KR | 1020170102000 A | 9/2017 | | |
| KR | 1020170127353 A | 11/2017 | | |
| WO | 2011-159872 A1 | 12/2011 | | |
| WO | 2012011756 A1 | 1/2012 | | |
| WO | 2013180020 A1 | 12/2013 | | |
| WO | 2014163083 A1 | 10/2014 | | |
| WO | 2016175068 A1 | 3/2016 | | |
| WO | 2016105161 A2 | 6/2016 | | |
| WO | 2017/018795 A2 | 2/2017 | | |
| WO | 2017078494 A1 | 5/2017 | | |
| WO | 2017/099490 A1 | 6/2017 | | |
| WO | 2017099471 A1 | 6/2017 | | |
| WO | 2017196081 A1 | 11/2017 | | |

OTHER PUBLICATIONS

JP-2014116454, downloaded Dec. 27, 2021 from Google Patents.*
JP2016149473 machine translation from Google Patents, downloaded Oct. 7, 2022.*
European Search Report issued by the European Patent Office dated Mar. 14, 2019 in the examination of the European Patent Application No. 18206972.4-1110, 7 pp.
English translation of Office Action issued in JP Patent Application No. 2017-244291 dated Nov. 2, 2021, 12 pp.
Office Action issued in JP Patent Application No. 2017-244291 dated Nov. 2, 2021, 9 pp.
English Translation of Office Action dated Dec. 26, 2022, issued in corresponding CN Patent Application No. 201811478220.X, 11 pp.
Office Action dated Dec. 26, 2022, issued in corresponding CN Patent Application No. 201811478220.X, 9 pp.
English Translation of Office Action issued in corresponding Korean application No. 10-2018-0076110, dated Mar. 16, 2023, 12 pp.
Office Action issued in corresponding Korean application No. 10-2018-0076110, dated Mar. 16, 2023, 11 pp.

* cited by examiner

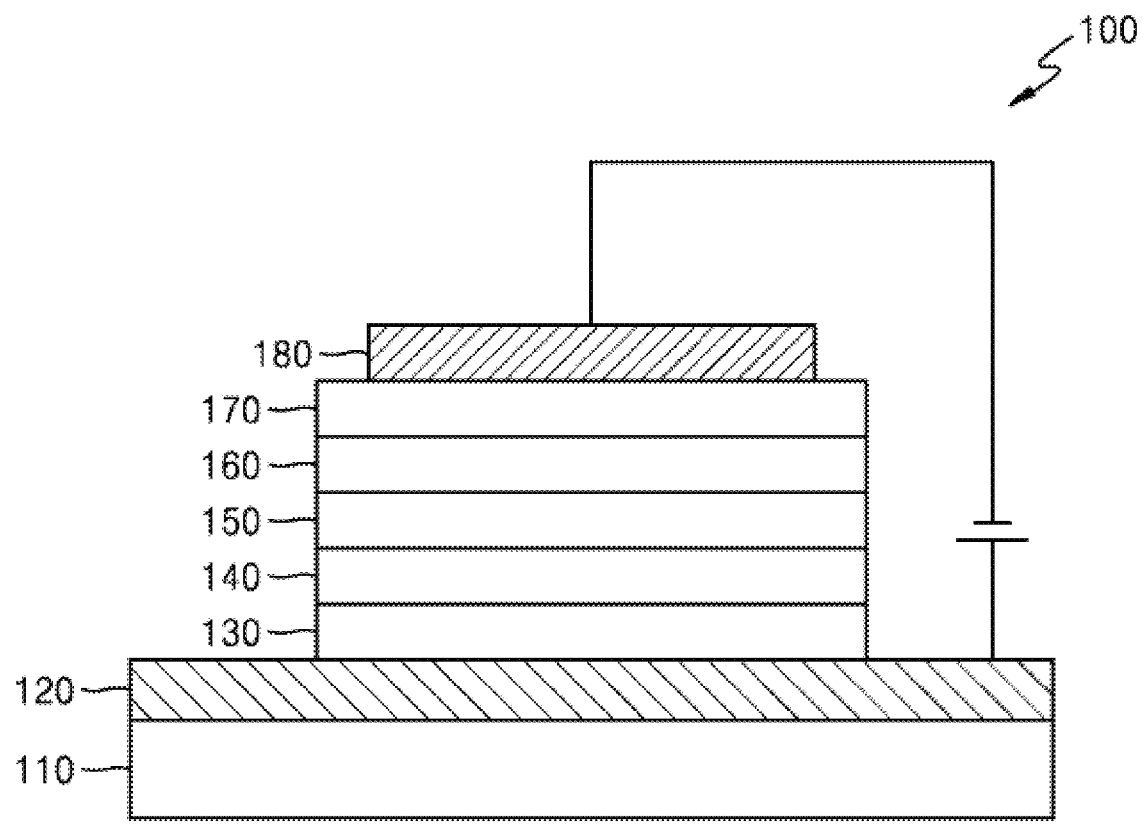

CONDENSED CYCLIC COMPOUND, COMPOSITION INCLUDING THE CONDENSED CYCLIC COMPOUND, AND ORGANIC LIGHT-EMITTING DEVICE INCLUDING THE COMPOSITION

CROSS-REFERENCE TO RELATED APPLICATIONS

This application claims priority to Japanese Patent Application No. 2017-244291, filed on Dec. 20, 2017, in the Japanese Patent Office and Korean Patent Application No. 10-2018-0076110, filed on Jun. 29, 2018, in the Korean Intellectual Property Office, and all the benefits accruing therefrom under 35 U.S.C. § 119, the contents of which are incorporated herein in their entireties by reference.

BACKGROUND

1. Field

One or more embodiments relate to a condensed cyclic compound, a composition including the condensed cyclic compound, and an organic light-emitting device including the condensed cyclic compound.

2. Description of the Related Art

Organic light-emitting devices (OLEDs) are self-emission devices, which have wide viewing angles, high contrast ratios, short response times, as well as excellent characteristics in terms of brightness, driving voltage, and response speed, and which produce full-color images.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state, thereby generating light.

Various types of organic light emitting devices are known. However, there still remains a need in OLEDs having low driving voltage, high efficiency, high brightness, and long lifespan.

SUMMARY

Aspects of the present disclosure provide a condensed cyclic compound, a composition including the condensed cyclic compound, and an organic light-emitting device including the condensed cyclic compound.

The organic light-emitting device including the condensed cyclic compound may provide high current efficiency and a long lifespan. In addition, the condensed cyclic compound may provide characteristics suitable for use in a solution coating.

Additional aspects will be set forth in part in the description which follows and, in part, will be apparent from the description, or may be learned by practice of the presented embodiments.

An aspect provides a condensed cyclic compound represented by Formula 1 and including 9 to 60 aromatic rings:

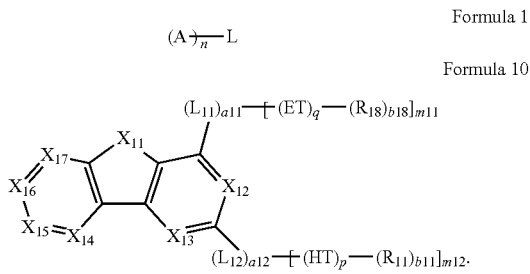

In Formulae 1 and 10,
A may be a group represented by Formula 10,
n may be selected from 1, 2, 3, and 4,
L may be hydrogen, a single bond or a linking group,
$X_{11}$ may be an oxygen atom or a sulfur atom,
$X_{12}$ may be selected from N and $C(R_{12})$, $X_{13}$ may be selected from N and $C(R_{13})$, $X_{14}$ may be selected from N and $C(R_{14})$, $X_{15}$ may be selected from N and $C(R_{15})$, $X_{16}$ may be selected from N and $C(R_{16})$, and $X_{17}$ may be selected from N and $C(R_{17})$,
$L_{11}$ and $L_{12}$ are each independently selected from a single bond, a substituted or unsubstituted carbocyclic group having 5 to 60 ring-forming carbon atoms, and a substituted or unsubstituted heterocyclic group having 5 to 60 ring-forming atoms,
a11 and a12 may each independently be selected from 0, 1, 2, 3, and 4,
HT may be selected from a substituted or unsubstituted carbazole group, a substituted or unsubstituted azacarbazole group, a substituted or unsubstituted benzocarbazole group, a substituted or unsubstituted hydrocarbazole group, a substituted or unsubstituted acridine group, a substituted or unsubstituted indole group, a substituted or unsubstituted xanthene group, a substituted or unsubstituted phenoxazine group, and a substituted or unsubstituted diphenyl amine group, and two or more substituents included in HT may optionally be linked to form a ring,
p may be selected from 0, 1, 2, 3, and 4,
ET may be a substituted or unsubstituted nitrogen-containing heteroaryl group having 5 to 60 ring-forming atoms, q may be selected from 0, 1, 2, 3, and 4,
$R_{11}$ and $R_{18}$ may each independently be selected from hydrogen, deuterium, —F, —Cl, —Br, —I, a substituted or unsubstituted aryl group having 6 to 60 ring-forming carbon atoms, and a substituted or unsubstituted heteroaryl group having 5 to 60 ring-forming atoms,
b11 and b18 may each independently be selected from 0, 1, 2, 3, 4, and 5,
$R_{12}$ to $R_{17}$ may each independently be selected from hydrogen, deuterium, —F, —Cl, —Br, —I, a substituted or unsubstituted aryl group having 6 to 60 ring-forming carbon atoms, and a substituted or unsubstituted heteroaryl group having 5 to 60 ring-forming atoms, and two neighboring groups selected from $R_{12}$ to $R_{17}$ may optionally be linked to form a ring,
m11 and m12 may each independently be selected from 1, 2, 3, and 4,
wherein, when n is 1, p is selected from 1, 2, 3, and 4, and q is selected from 1, 2, 3, and 4, and wherein the valence of the group represented by Formula 10 is determined by n and L in Formula 1.

Another aspect provides a composition including at least one of a condensed cyclic compound represented by Formula 1.

Another aspect provides an organic light-emitting device including:

a first electrode;

a second electrode; and an organic layer disposed between the first electrode and the second electrode, wherein the organic layer includes an emission layer, and wherein the organic layer includes at least one of the condensed cyclic compound.

BRIEF DESCRIPTION OF THE DRAWINGS

These and/or other aspects will become apparent and more readily appreciated from the following description of the embodiments, taken in conjunction with the FIGURE which is a schematic view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Condensed Cyclic Compound

A condensed cyclic compound according to an embodiment is represented by Formula 1:

Formula 1

In Formula 1, A may be a group represented by Formula 10, n may be selected from 1, 2, 3, and 4, and L may be hydrogen, a single bond or a linking group:

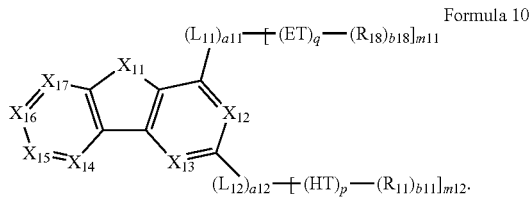

Formula 10

In Formula 10, $X_{11}$ to $X_{17}$, $L_{11}$, $L_{12}$, a11, a12, ET, HT, p, q, $R_{11}$, $R_{18}$, b11, b18, m11, and m12 may each independently be the same as described herein.

The condensed cyclic compound represented by Formula 1 includes 9 to 60 aromatic rings. The number of the aromatic rings in a term "9 to 60 aromatic rings" is obtained by counting the number of the single 6-membered aromatic rings in the condensed cyclic compound. Since the condensed cyclic compound represented by Formula 1 essentially includes 9 to 60 aromatic rings, the condensed cyclic compound may have improved solubility in an organic solvent. Since a 6-membered aromatic ring is linked in a chain shape, the degree of freedom of the condensed cyclic compound increases, thereby improving the solubility in the organic solvent. Therefore, since it is advantageous to a solution process, it is possible to provide a layer (or a thin film) having improved film-forming characteristics.

Therefore, even when an organic light-emitting device is manufactured by using solution coating, the performance (for example, current efficiency, lifespan, or the like) of the organic light-emitting device may be maintained or improved. Consequently, the organic light-emitting device may be manufactured without using expensive vacuum deposition. In particular, it may be advantageous to manufacturing a large-scale organic light-emitting device.

The term "aromatic ring" as used herein refers to a ring structure having aromaticity and may refer to a structure having (4n+2) π electrons (n is an integer of 1 or more). The aromatic ring may have only a carbon atom, or may further include heterogeneous elements. In addition, the aromatic ring may be a single cyclic structure including only one ring, or may be a multi cyclic structure.

For example, the condensed cyclic compound may include 10 or more, 11 or more, or 12 or more aromatic rings, but embodiments of the present disclosure are not limited thereto.

In an embodiment, the condensed cyclic compound may include 10 to 30 aromatic rings, but embodiments of the present disclosure are not limited thereto.

In one or more embodiments, the condensed cyclic compound may include 9 to 60 6-membered aromatic rings (for example, a benzene ring, a pyridine ring, a pyrimidine ring, or the like), but embodiments of the present disclosure are not limited thereto.

For example, the condensed cyclic compound may have a molecular weight of about 850 Daltons to about 3,000 Daltons, but embodiments of the present disclosure are not limited thereto. While not wishing to be bound by theory, it is understood that when satisfying the above-described range, the solubility of the condensed cyclic compound is improved, thereby providing a thin film having high performance.

For example, the solubility of the condensed cyclic compound to an ester-based organic solvent at room temperature (about 20° C.) may be 0.5 percent by weight (weight %) or more, but embodiments of the present disclosure are not limited thereto. For example, the solubility may be 1 weight % or more, but embodiments of the present disclosure are not limited thereto. In particular, the solubility to methyl benzoate at room temperature may be 0.5 weight % or more, but embodiments of the present disclosure are not limited thereto.

For example, in Formula 1, n may be selected from 1 and 2, but embodiments of the present disclosure are not limited thereto. When n is 1, the condensed cyclic compound may be a monomer, L may be hydrogen, the condensed cyclic compound may have a structure such as A-H. When n is two or more, L may be a n-valent linking group linked to groups A in the number of n. When n is two or more, a plurality of groups A may be identical to or different from each other. When n is 2 and L is a single bond, two same or different groups A are linked via the single bond to form the condensed cyclic compound.

For example, L in Formula 1 may be selected from hydrogen, a single bond, a substituted or unsubstituted carbocyclic group having 5 to 60 ring-forming carbon atoms, and a substituted or unsubstituted heterocyclic group having 5 to 60 ring-forming atoms, but embodiments of the present disclosure are not limited thereto.

In an embodiment, L in Formula 1 may be selected from hydrogen, a single bond, a substituted or unsubstituted benzene group, a substituted or unsubstituted biphenyl group, a substituted or unsubstituted terphenyl group, and a substituted or unsubstituted carbazole group, but embodiments of the present disclosure are not limited thereto.

In Formula 10, $X_{11}$ may be an oxygen atom or a sulfur atom.

In Formula 10, $X_{12}$ may be selected from N and $C(R_{12})$, $X_{13}$ may be selected from N and $C(R_{13})$, $X_{14}$ may be selected from N and $C(R_{14})$, $X_{15}$ may be selected from N and $C(R_{15})$, $X_{16}$ may be selected from N and $C(R_{16})$, and $X_{17}$ may be selected from N and $C(R_{17})$.

For example, in Formula 10, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, and $X_{17}$ may be $C(R_{17})$, but embodiments of the present disclosure are not limited thereto.

In Formula 10, $L_{11}$ and $L_{12}$ may each independently be selected from a single bond, a substituted or unsubstituted carbocyclic group having 5 to 60 ring-forming carbon atoms, and a substituted or unsubstituted heterocyclic group having 5 to 60 ring-forming atoms.

For example, $L_{11}$ and $L_{12}$ in Formula 10 may each independently be selected from a single bond, a substituted or unsubstituted benzene group, a substituted or unsubstituted indene group, a substituted or unsubstituted naphthalene group, a substituted or unsubstituted acenaphthalene group, a substituted or unsubstituted biphenyl group, a substituted or unsubstituted terphenyl group, a substituted or unsubstituted tetraphenyl group, a substituted or unsubstituted fluorene group, a substituted or unsubstituted spirobifluorene group, a substituted or unsubstituted phenanthrene group, a substituted or unsubstituted anthracene group, a substituted or unsubstituted fluoranthene group, a substituted or unsubstituted triphenylene group, a substituted or unsubstituted pyrene group, a substituted or unsubstituted chrysene group, a substituted or unsubstituted perylene group, a substituted or unsubstituted benzofluorene group, a substituted or unsubstituted pyrrole group, a substituted or unsubstituted imidazole group, a substituted or unsubstituted pyrazole group, a substituted or unsubstituted triazole group, a substituted or unsubstituted pyridine group, a substituted or unsubstituted pyrazine group, a substituted or unsubstituted pyrimidine group, a substituted or unsubstituted pyridazine group, a substituted or unsubstituted triazine group, a substituted or unsubstituted furan group, a substituted or unsubstituted thiophene group, a substituted or unsubstituted oxazole group, a substituted or unsubstituted isoxazole group, a substituted or unsubstituted thiazole group, a substituted or unsubstituted isothiazole group, a substituted or unsubstituted oxadiazole group, a substituted or unsubstituted isoxadiazole group, a substituted or unsubstituted thiadiazole group, a substituted or unsubstituted isothiadiazole group, a substituted or unsubstituted pyran group, a substituted or unsubstituted indazole group, a substituted or unsubstituted purine group, a substituted or unsubstituted quinoline group, a substituted or unsubstituted isoquinoline group, a substituted or unsubstituted benzoquinoline group, a substituted or unsubstituted phthalazine group, a substituted or unsubstituted naphthyridine group, a substituted or unsubstituted quinoxaline group, a substituted or unsubstituted quinazoline group, a substituted or unsubstituted cinnoline group, a substituted or unsubstituted phenanthridine group, a substituted or unsubstituted acridine group, a substituted or unsubstituted phenanthroline group, a substituted or unsubstituted phenazine group, a substituted or unsubstituted benzoxazole group, a substituted or unsubstituted benzothiazole group, a substituted or unsubstituted benzimidazole group, a substituted or unsubstituted isoindole group, a substituted or unsubstituted indole group, a substituted or unsubstituted benzofuran group, a substituted or unsubstituted benzothiophene group, a substituted or unsubstituted carbazole group, a substituted or unsubstituted dibenzofuran group, a substituted or unsubstituted dibenzothiophene group, a substituted or unsubstituted azadibenzofuran group, a substituted or unsubstituted azadibenzothiophene group, a substituted or unsubstituted diazadibenzofuran group, a substituted or unsubstituted diazadibenzothiophene group, a substituted or unsubstituted xanthene group, a substituted or unsubstituted phenoxazine group, a substituted or unsubstituted benzocarbazole group, a substituted or unsubstituted hydrocarbazole group, a substituted or unsubstituted naphtho benzofuran group, a substituted or unsubstituted naphtho benzothiophene group, a substituted or unsubstituted imidazopyrimidine group, a substituted or unsubstituted imidazopyridine group, a substituted or unsubstituted diphenylamine group, and a substituted or unsubstituted triphenylamine group, but embodiments of the present disclosure are not limited thereto.

In an embodiment, $L_{11}$ and $L_{12}$ in Formula 10 may each independently be selected from a single bond, a substituted or unsubstituted benzene group, a substituted or unsubstituted biphenyl group, a substituted or unsubstituted terphenyl group, a substituted or unsubstituted tetraphenyl group, a substituted or unsubstituted naphthalene group, a substituted or unsubstituted fluorene group, a substituted or unsubstituted pyridine group, a substituted or unsubstituted pyrimidine group, and a substituted or unsubstituted triazine group, but embodiments of the present disclosure are not limited thereto.

In an embodiment, $L_{11}$ and $L_{12}$ in Formula 10 may each independently be selected from a single bond and a substituted or unsubstituted benzene group, but embodiments of the present disclosure are not limited thereto.

In Formula 10, $L_{11}$ and $L_{12}$ may each independently have a binding site at a metha- or para-position to a 6-membered ring, but embodiments of the present disclosure are not limited thereto.

In Formula 10, a11 and a12 may each independently indicate the repetitions of $L_{11}$ and $L_{12}$, and may each independently be selected from 0, 1, 2, 3, and 4. When a11 is 0, $(L_{11})_{a11}$ may be a single bond, when a11 is two or more, a plurality of groups $L_{11}$ may be identical to or different from each other, when a12 is 0, $(L_{12})_{a12}$ may be a single bond, and when a12 is two or more, a plurality of groups $L_{12}$ may be identical to or different from each other.

For example, a11 and a12 in Formula 10 may each independently be selected from 1, 2, 3, and 4, but embodiments of the present disclosure are not limited thereto.

In an embodiment, a11 and a12 in Formula 10 may each independently be selected from 2, 3, and 4, but embodiments of the present disclosure are not limited thereto.

In Formula 10, HT may be selected from a substituted or unsubstituted carbazole group, a substituted or unsubstituted azacarbazole group, a substituted or unsubstituted benzocarbazole group, a substituted or unsubstituted hydrocarbazole group, a substituted or unsubstituted acridine group, a substituted or unsubstituted indole group, a substituted or unsubstituted xanthene group, a substituted or unsubstituted phenoxazine group, and a substituted or unsubstituted diphenyl amine group, wherein at least two substituents included in HT may be optionally linked each other to form a ring.

For example, HT in Formula 10 may be selected from:
  a carbazole group, an azacarbazole group, a benzocarbazole group, a hydrocarbazole group, an acridine group, an indolyl group, a xanthene group, a phenoxazine group, and a diphenyl amine group; and
  a carbazole group, an azacarbazole group, a benzocarbazole group, a hydrocarbazole group, an acridine group, an indole group, a xanthene group, a phenoxazine group, and a diphenyl amine group, each substituted with at least one selected from deuterium, —F, —Cl, —Br, —I, a substituted or unsubstituted aryl group having 6 to 60 ring-forming carbon atoms, and a substituted or unsubstituted heteroaryl group having 5 to 60 ring-forming atoms,
  wherein at least two substituents included in HT may be optionally linked each other to form a ring, but embodiments of the present disclosure are not limited thereto.

In an embodiment, HT in Formula 10 may be represented by one selected from Formulae 3-1 to 3-9, but embodiments of the present disclosure are not limited thereto:

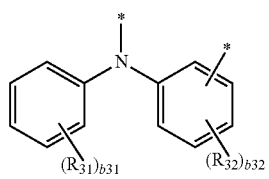

3-1

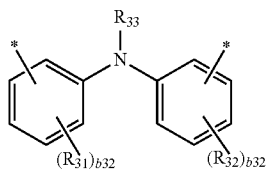

3-2

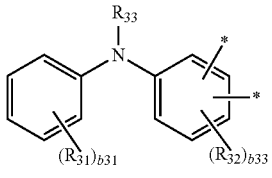

3-3

-continued

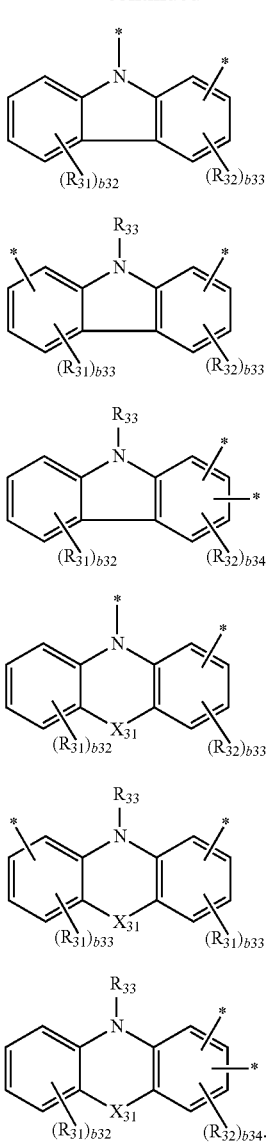

In Formulae 3-1 to 3-9,
$X_{31}$ may be selected from O and $C(R_{34})(R_{35})$,
$R_{31}$ to $R_{35}$ may each independently be selected from hydrogen, deuterium, —F, —Cl, —Br, —I, a substituted or unsubstituted aryl group having 6 to 60 ring-forming carbon atoms, and a substituted or unsubstituted heteroaryl group having 5 to 60 ring-forming atoms,
two neighboring groups selected from $R_{31}$ to $R_{35}$ may be optionally linked each other to form a ring,
b31 may be selected from 1, 2, 3, 4, and 5,
b32 may be selected from 1, 2, 3, and 4,
b33 may be selected from 1, 2, and 3,
b34 may be selected from 1 and 2, and
* indicates a binding site to a neighboring atom.

In an embodiment, $R_{31}$ to $R_{35}$ in Formulae 3-1 to 3-9 may each independently be selected from hydrogen, deuterium, a substituted or unsubstituted phenyl group, a substituted or unsubstituted indenyl group, a substituted or unsubstituted naphthyl group, a substituted or unsubstituted acenaphthyl group, a substituted or unsubstituted biphenyl group, a substituted or unsubstituted terphenyl group, a substituted or unsubstituted fluorenyl group, a substituted or unsubstituted spiro-bifluorenyl group, a substituted or unsubstituted phenanthrenyl group, a substituted or unsubstituted anthracenyl group, a substituted or unsubstituted fluoranthenyl group, a substituted or unsubstituted triphenyl group, a substituted or unsubstituted pyrenyl group, a substituted or unsubstituted chrysenyl group, a substituted or unsubstituted perylenyl group, a substituted or unsubstituted benzofluorenyl group, a substituted or unsubstituted pyrrolyl group, a substituted or unsubstituted imidazolyl group, a substituted or unsubstituted pyrazolyl group, a substituted or unsubstituted triazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted triazinyl group, a substituted or unsubstituted furanyl group, a substituted or unsubstituted thiophenyl group, a substituted or unsubstituted oxazolyl group, a substituted or unsubstituted isoxazolyl group, a substituted or unsubstituted thiazolyl group, a substituted or unsubstituted isothiazolyl group, a substituted or unsubstituted oxadiazolyl group, a substituted or unsubstituted isoxadiazolyl group, a substituted or unsubstituted thiadiazolyl group, a substituted or unsubstituted isothiadiazolyl group, a substituted or unsubstituted pyranyl group, a substituted or unsubstituted indazolyl group, a substituted or unsubstituted purinyl group, a substituted or unsubstituted quinolinyl group, a substituted or unsubstituted isoquinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzoxazolyl group, a substituted or unsubstituted benzothiazolyl group, a substituted or unsubstituted benzimidazolyl group, a substituted or unsubstituted isoindolyl group, a substituted or unsubstituted indolyl group, a substituted or unsubstituted benzofuranyl group, a substituted or unsubstituted benzothiophenyl group, a substituted or unsubstituted carbazolyl group, a substituted or unsubstituted azacarbazolyl group, a substituted or unsubstituted dibenzofuranyl group, a substituted or unsubstituted dibenzothiophenyl group, a substituted or unsubstituted azadibenzofuranyl group, a substituted or unsubstituted diazadibenzofuranyl group, a substituted or unsubstituted azadibenzothiophenyl group, a substituted or unsubstituted diazadibenzothiophenyl group, a substituted or unsubstituted xanthenyl group, a substituted or unsubstituted phenoxazinyl group, a substituted or unsubstituted benzocarbazolyl group, a substituted or unsubstituted hydrocarbazolyl group, a substituted or unsubstituted naphthobenzofuranyl group, a substituted or unsubstituted naphthobenzothiophenyl group, a substituted or unsubstituted imidazopyrimidinyl group, a substituted or unsubstituted imidazopyridinyl group, a substituted or unsubstituted group derived from diphenylamine, and a substituted or unsubstituted group derived from triphenylamine, but embodiments of the present disclosure are not limited thereto.

In one or more embodiments $R_{31}$ to $R_{35}$ in Formulae 3-1 to 3-9 may each independently be selected from hydrogen, deuterium, a substituted or unsubstituted phenyl group, a substituted or unsubstituted biphenyl group, a substituted or unsubstituted terphenyl group, a substituted or unsubstituted tetraphenyl group, a substituted or unsubstituted naphthyl group, a substituted or unsubstituted fluorenyl group, a substituted or unsubstituted phenanthrenyl group, a substituted or unsubstituted pyridinyl group, a substituted or unsubstituted pyrazinyl group, a substituted or unsubstituted pyrimidinyl group, a substituted or unsubstituted pyridazinyl group, and a substituted or unsubstituted triazinyl group, but embodiments of the present disclosure are not limited thereto.

in an embodiment, when HT in Formula 10 is a substituted or unsubstituted azacarbazole group, HT may be a group derived from compounds represented by the following formulae, but embodiments of the present disclosure are not limited thereto:

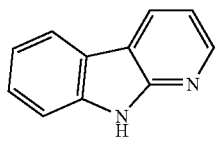
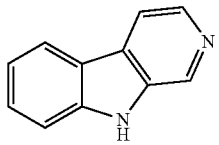

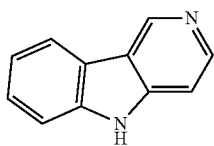
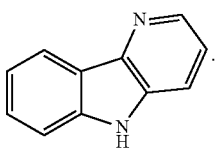

Here, two groups H may each independently be replaced with a binding site to a neighboring atom.

In an embodiment, when HT in Formula 10 is a substituted or unsubstituted benzocarbazole group, HT may be a group derived from compounds represent by Formulae 4-1 to 4-5, but embodiments of the present disclosure are not limited thereto:

4-1
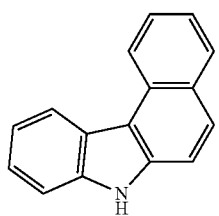

4-2
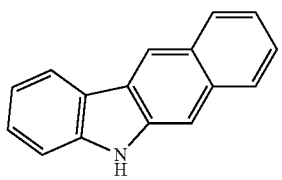

4-3
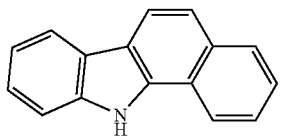

4-4
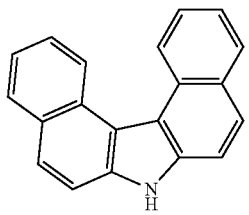

4-5
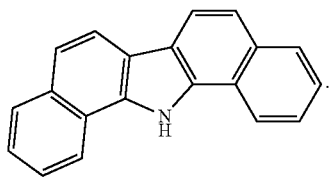

In Formulae 4-1 to 4-5, two groups H may each independently be replaced with a binding site to a neighboring atom.

In an embodiment, when HT in Formula 10 is a substituted or unsubstituted hydrocarbazole group, HT may be a group derived from compounds represent by Formulae 4-6 and 4-7, but embodiments of the present disclosure are not limited thereto:

4-6
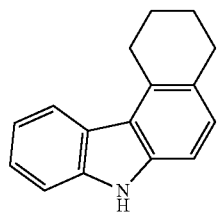

4-7
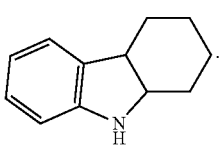

In Formulae 4-6 and 4-7, 2 two groups H may each independently be replaced with a binding site to a neighboring atom.

In an embodiment, when HT in Formula 10 is a substituted or unsubstituted acridine group, HT may be a group derived from a compound represent by Formula 4-8, but embodiments of the present disclosure are not limited thereto:

4-8
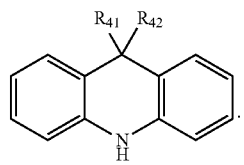

In Formula 4-8,
$R_{41}$ and $R_{42}$ may each independently be selected from hydrogen, deuterium, —F, —Cl, —Br, —I, a substituted or unsubstituted $C_{1-10}$ alkyl group, a substituted or unsubstituted $C_{3-10}$ cycloalkyl group, a substituted or unsubstituted aryl group having 6 to 60 ring-forming carbon atoms, and a substituted or unsubstituted heteroaryl group having 5 to 60 ring-forming atoms, and two groups H may each independently be replaced with a binding site to a neighboring atom.

In an embodiment, when HT in Formula 10 is a substituted or unsubstituted indole group, HT may be a group derived from a compound represented by Formula 4-9, but embodiments of the present disclosure are not limited thereto:

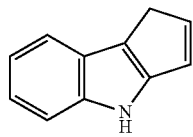

4-9

In Formula 4-9, two groups H may each independently be replaced with a binding site to a neighboring atom.

In an embodiment, when HT in Formula 10 is a substituted or unsubstituted xanthene group, HT may be a group derived from a compound represented by Formula 4-10, but embodiments of the present disclosure are not limited thereto:

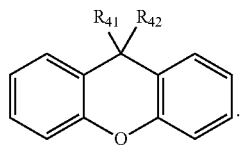

4-10

In Formula 4-10, $R_{41}$ and $R_{42}$ may each independently be selected from hydrogen, deuterium, —F, —Cl, —Br, —I, a substituted or unsubstituted $C_{1-10}$ alkyl group, a substituted or unsubstituted $C_{3-10}$ cycloalkyl group, a substituted or unsubstituted aryl group having 6 to 60 ring-forming carbon atoms, and a substituted or unsubstituted heteroaryl group having 5 to 60 ring-forming atoms, and two groups H may each independently be replaced with a binding site to a neighboring atom.

In an embodiment, when HT in Formula 10 is a substituted or unsubstituted phenoxazine group, HT may be a group derived from a compound represented by Formula 4-11, but embodiments of the present disclosure are not limited thereto:

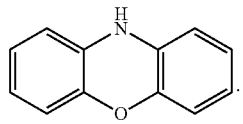

4-11

In Formula 4-11, two groups H may each independently be replaced with a binding site to a neighboring atom.

In Formula 10, p indicates the number of repetitions of HT, and may be selected from 0, 1, 2, 3, and 4. When p is two or more, a plurality of groups HT may be identical to or different from each other.

For example, p in Formula 10 may be selected from 0 and 1, but embodiments of the present disclosure are not limited thereto.

In Formula 10, ET may be a substituted or unsubstituted nitrogen-containing heteroaryl group having 5 to 60 ring-forming atoms. For example, ET in Formula 10 may have a monocyclic or polycyclic structure, wherein the structure may be a 5-membered ring structure, a 6-membered ring structure, a structure in which at least two 5-membered rings condensed, a structure in which at least two 6-membered rings are condensed, or a structure in which at least one 5-membered rings and at least one 6-membered rings are condensed, but embodiments of the present disclosure are not limited thereto.

For example, ET in Formula 10 may be selected from a substituted or unsubstituted pyrrole group, a substituted or unsubstituted pyrazole group, a substituted or unsubstituted imidazole group, a substituted or unsubstituted triazole group, a substituted or unsubstituted pyridine group, a substituted or unsubstituted pyrimidine group, a substituted or unsubstituted pyridazine group, a substituted or unsubstituted pyrazine group, a substituted or unsubstituted triazine group, a substituted or unsubstituted indole group, a substituted or unsubstituted isoindole group, a substituted or unsubstituted indazole group, a substituted or unsubstituted benzimidazole group, a substituted or unsubstituted quinoline group, a substituted or unsubstituted isoquinoline group, a substituted or unsubstituted phthalazine group, a substituted or unsubstituted naphthyridine group, a substituted or unsubstituted cinnoline group, a substituted or unsubstituted quinoxaline group, a substituted or unsubstituted quinazoline group, and a substituted or unsubstituted imidazopyridine group, but embodiments of the present disclosure are not limited thereto.

In an embodiment, ET in Formula 10 may be selected from:

a pyrrole group, a pyrazole group, an imidazole group, a triazole group, a pyridine group, a pyrimidine group, a pyridazine group, a pyrazine group, a triazine group, an indole group, an isoindole group, an indazole group, a benzimidazole group, a quinoline group, an isoquinoline group, a phthalazine group, a naphthyridine group, a cinnoline group, a quinoxaline group, a quinazoline group, and an imidazopyridine group; and a pyrrole group, a pyrazole group, an imidazole group, a triazole group, a pyridine group, a pyrimidine group, a pyridazine group, a pyrazine group, a triazine group, an indole group, an isoindole group, an indazole group, a benzimidazole group, a quinoline group, an isoquinoline group, a phthalazine group, a naphthyridine group, a cinnoline group, a quinoxaline group, a quinazoline group, and an imidazopyridine group, each substituted with at least one selected from deuterium, —F, —Cl, —Br, —I, a substituted or unsubstituted aryl group having 6 to 60 ring-forming carbon atoms, and a substituted or unsubstituted heteroaryl group having 5 to 60 ring-forming atoms, but embodiments of the present disclosure are not limited thereto.

In an embodiment, ET in Formula 10 may be a group represented by one selected from Formulae 2-1 to 2-4, but embodiments of the present disclosure are not limited thereto:

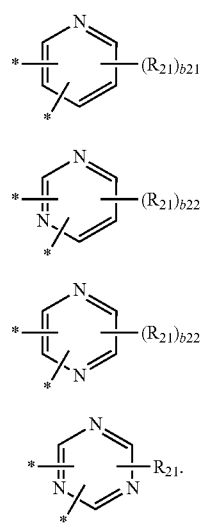

In Formulae 2-1 to 2-4, $R_{21}$ may be selected from deuterium, —F, —Cl, —Br, —I, a substituted or unsubstituted aryl group having 6 to 60 ring-forming carbon atoms, and a substituted or unsubstituted heteroaryl group having 5 to 60 ring-forming atoms, two neighboring groups selected from groups $R_{21}$ may be optionally linked each other to form a ring, b21 may be selected from 1, 2, and 3, b22 may be selected from 1 and 2, and

* indicates a binding site to a neighboring atom.

In an embodiment, $R_{21}$ in Formulae 2-1 to 2-4 may be selected from hydrogen, deuterium, a substituted or unsubstituted phenyl group, a substituted or unsubstituted indenyl group, a substituted or unsubstituted naphthyl group, a substituted or unsubstituted acenaphthyl group, a substituted or unsubstituted biphenyl group, a substituted or unsubstituted terphenyl group, a substituted or unsubstituted fluorenyl group, a substituted or unsubstituted spiro-bifluorenyl group, a substituted or unsubstituted phenanthrenyl group, a substituted or unsubstituted anthracenyl group, a substituted or unsubstituted fluoranthenyl group, a substituted or unsubstituted triphenyl group, a substituted or unsubstituted pyrenyl group, a substituted or unsubstituted chrysenyl group, a substituted or unsubstituted perylenyl group, a substituted or unsubstituted benzofluorenyl group, a substituted or unsubstituted pyrrolyl group, a substituted or unsubstituted imidazolyl group, a substituted or unsubstituted pyrazolyl group, a substituted or unsubstituted triazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted triazinyl group, a substituted or unsubstituted furanyl group, a substituted or unsubstituted thiophenyl group, a substituted or unsubstituted oxazolyl group, a substituted or unsubstituted isoxazolyl group, a substituted or unsubstituted thiazolyl group, a substituted or unsubstituted isothiazolyl group, a substituted or unsubstituted oxadiazolyl group, a substituted or unsubstituted isoxadiazolyl group, a substituted or unsubstituted thiadiazolyl group, a substituted or unsubstituted isothiadiazolyl group, a substituted or unsubstituted pyranyl group, a substituted or unsubstituted indazolyl group, a substituted or unsubstituted purinyl group, a substituted or unsubstituted quinolinyl group, a substituted or unsubstituted isoquinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzoxazolyl group, a substituted or unsubstituted benzothiazolyl group, a substituted or unsubstituted benzimidazolyl group, a substituted or unsubstituted isoindolyl group, a substituted or unsubstituted indolyl group, a substituted or unsubstituted benzofuranyl group, a substituted or unsubstituted benzothiophenyl group, a substituted or unsubstituted carbazolyl group, a substituted or unsubstituted azacarbazolyl group, a substituted or unsubstituted dibenzofuranyl group, a substituted or unsubstituted dibenzothiophenyl group, a substituted or unsubstituted azadibenzofuranyl group, a substituted or unsubstituted diazadibenzofuranyl group, a substituted or unsubstituted azadibenzothiophenyl group, a substituted or unsubstituted diazadibenzothiophenyl group, a substituted or unsubstituted xanthenyl group, a substituted or unsubstituted phenoxazinyl group, a substituted or unsubstituted benzocarbazolyl group, a substituted or unsubstituted hydrocarbazolyl group, a substituted or unsubstituted naphthobenzofuranyl group, a substituted or unsubstituted naphthobenzothiophenyl group, a substituted or unsubstituted imidazopyrimidinyl group, a substituted or unsubstituted imidazopyridinyl group, a substituted or unsubstituted group derived from diphenylamine, and a substituted or unsubstituted group derived from triphenylamine, but embodiments of the present disclosure are not limited thereto.

In one or more embodiments, $R_{21}$ in Formulae 2-1 to 2-4 may each independently be selected from hydrogen, deuterium, a substituted or unsubstituted phenyl group, a substituted or unsubstituted biphenyl group, a substituted or unsubstituted terphenyl group, a substituted or unsubstituted tetraphenyl group, a substituted or unsubstituted naphthyl group, a substituted or unsubstituted fluorenyl group, a substituted or unsubstituted phenanthrenyl group, a substituted or unsubstituted pyridinyl group, a substituted or unsubstituted pyrazinyl group, a substituted or unsubstituted pyrimidinyl group, a substituted or unsubstituted pyridazinyl group, and a substituted or unsubstituted triazinyl group, but embodiments of the present disclosure are not limited thereto.

In Formula 10, q indicates the number of the repetitions of ET, and may be selected from 0, 1, 2, 3, and 4. When q is two or more, a plurality of groups ET may be identical to or different from each other.

For example, q in Formula 10 may be selected from 0 and 1, but embodiments of the present disclosure are not limited thereto.

In Formula 10, $R_{11}$ and $R_{18}$ may each independently be selected from hydrogen, deuterium, —F, —Cl, —Br, —I, a substituted or unsubstituted aryl group having 6 to 60 ring-forming carbon atoms, and a substituted or unsubstituted heteroaryl group having 5 to 60 ring-forming atoms.

In Formula 10, $R_{12}$ to $R_{17}$ may each independently be selected from hydrogen, deuterium, —F, —Cl, —Br, —I, a substituted or unsubstituted aryl group having 6 to 60 ring-forming carbon atoms, and a substituted or unsubstituted heteroaryl group having 5 to 60 ring-forming atoms, and two neighboring groups selected from $R_{12}$ to $R_{17}$ may be optionally linked each other to form a ring.

For example, $R_{11}$ to $R_{18}$ in Formula 10 may each independently be selected from hydrogen, deuterium, a substituted or unsubstituted phenyl group, a substituted or unsubstituted indenyl group, a substituted or unsubstituted naphthyl group, a substituted or unsubstituted acenaphthyl group, a substituted or unsubstituted biphenyl group, a substituted or unsubstituted terphenyl group, a substituted or unsubstituted fluorenyl group, a substituted or unsubstituted spiro-bifluorenyl group, a substituted or unsubstituted phenanthrenyl group, a substituted or unsubstituted anthracenyl group, a substituted or unsubstituted fluoranthenyl group, a substituted or unsubstituted triphenyl group, a substituted or unsubstituted pyrenyl group, a substituted or unsubstituted chrysenyl group, a substituted or unsubstituted perylenyl group, a substituted or unsubstituted benzofluorenyl group, a substituted or unsubstituted pyrrolyl group, a substituted or unsubstituted imidazolyl group, a substituted or unsubstituted pyrazolyl group, a substituted or unsubstituted triazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted triazinyl group, a substituted or unsubstituted furanyl group, a substituted or unsubstituted thiophenyl group, a substituted or unsubstituted oxazolyl group, a substituted or unsubstituted isoxazolyl group, a substituted or unsubstituted thiazolyl group, a substituted or unsubstituted isothiazolyl group, a substituted or unsubstituted oxadiazolyl group, a substituted or unsubstituted isoxadiazolyl group, a substituted or unsubstituted thiadiazolyl group, a substituted or unsubstituted isothiadiazolyl group, a substituted or unsubstituted pyranyl group, a substituted or unsubstituted indazolyl group, a substituted or unsubstituted purinyl group, a substituted or unsubstituted quinolinyl group, a substituted or unsubstituted isoquinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzoxazolyl group, a substituted or unsubstituted benzothiazolyl group, a substituted or unsubstituted benzimidazolyl group, a substituted or unsubstituted isoindolyl group, a substituted or unsubstituted indolyl group, a substituted or unsubstituted benzofuranyl group, a substituted or unsubstituted benzothiophenyl group, a substituted or unsubstituted carbazolyl group, a substituted or unsubstituted azacarbazolyl group, a substituted or unsubstituted dibenzofuranyl group, a substituted or unsubstituted dibenzothiophenyl group, a substituted or unsubstituted azadibenzofuranyl group, a substituted or unsubstituted diazadibenzofuranyl group, a substituted or unsubstituted azadibenzothiophenyl group, a substituted or unsubstituted diazadibenzothiophenyl group, a substituted or unsubstituted xanthenyl group, a substituted or unsubstituted phenoxazinyl group, a substituted or unsubstituted benzocarbazolyl group, a substituted or unsubstituted hydrocarbazolyl group, a substituted or unsubstituted naphtho benzofuranyl group, a substituted or unsubstituted naphtho benzothiophenyl group, a substituted or unsubstituted imidazopyrimidinyl group, a substituted or unsubstituted imidazopyridinyl group, a substituted or unsubstituted group derived from diphenyl amine, and a substituted or unsubstituted group derived from triphenylamine, but embodiments of the present disclosure are not limited thereto.

In an embodiment, $R_{11}$ to $R_{18}$ in Formula 10 may each independently be selected from hydrogen, deuterium, a substituted or unsubstituted phenyl group, a substituted or unsubstituted biphenyl group, a substituted or unsubstituted terphenyl group, a substituted or unsubstituted tetraphenyl group, a substituted or unsubstituted naphthyl group, a substituted or unsubstituted fluorenyl group, a substituted or unsubstituted phenanthrenyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted triazinyl group, a substituted or unsubstituted carbazolyl group, a substituted or unsubstituted azacarbazolyl group, a substituted or unsubstituted benzocarbazolyl group, a substituted or unsubstituted hydrocarbazolyl group, a substituted or unsubstituted acridinyl group, a substituted or unsubstituted indolyl group, a substituted or unsubstituted xanthenyl group, a substituted or unsubstituted phenoxazinyl group, a substituted or unsubstituted group derived from diphenyl amine, and a substituted or unsubstituted group derived from triphenylamine, but embodiments of the present disclosure are not limited thereto.

In an embodiment, $R_{11}$ to $R_{18}$ in Formula 10 may each independently be selected from hydrogen, deuterium, a substituted or unsubstituted phenyl group, a substituted or unsubstituted biphenyl group, a substituted or unsubstituted terphenyl group, a substituted or unsubstituted tetraphenyl group, a substituted or unsubstituted naphthyl group, a substituted or unsubstituted fluorenyl group, a substituted or unsubstituted pyridinyl group, and a substituted or unsubstituted pyrimidinyl group, but embodiments of the present disclosure are not limited thereto.

In Formula 10, b11 and b18 respectively indicate the number of groups $R_{11}$ and groups $R_{18}$, and b11 and b18 may each independently be selected from 0, 1, 2, 3, 4, and 5.

In Formula 10, m11 and m12 may each independently be selected from 1, 2, 3, and 4.

For example, in Formula 10, m11 and m12 may each independently be selected from 1 and 2, but embodiments of the present disclosure are not limited thereto.

In Formula 1, when n is 1, p may be selected from 1, 2, 3, and 4, and q may be selected from 1, 2, 3, and 4.

In an embodiment, the condensed cyclic compound may be represented by one selected from Formulae 1-1 to 1-6, but embodiments of the present disclosure are not limited thereto:

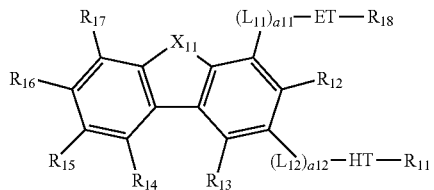

1-1

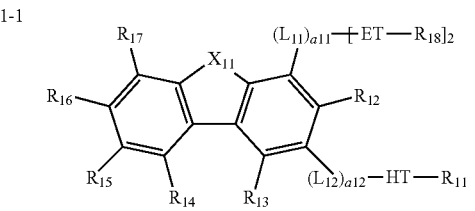

1-2

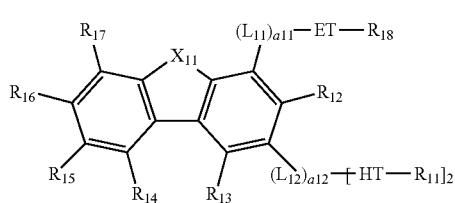

1-3

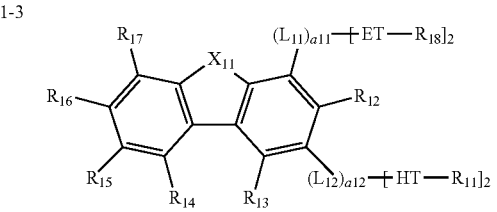

1-4

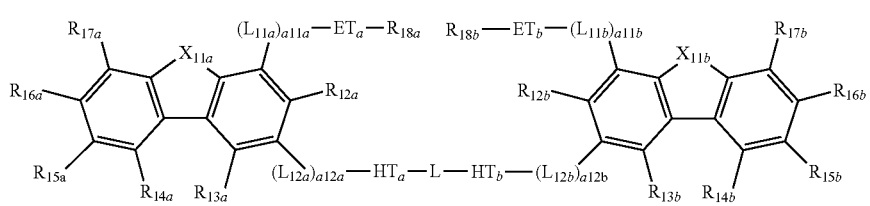

1-5

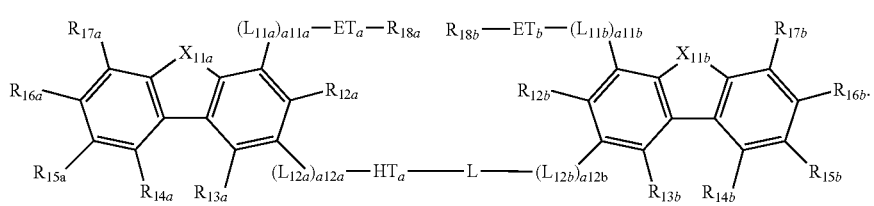

1-6

In Formulae 1-1 to 1-6,

L may be the same as described in Formula 1, $X_{11}$, $R_{11}$ to $R_{18}$, ET, HT, $L_{11}$, $L_{12}$, a11, and a12 may each independently be the same as described in Formula 10, $X_{11a}$ and $X_{11b}$ may each independently be the same as described in connection with $X_{11}$ in Formula 10, $R_{12a}$, $R_{12b}$, $R_{13a}$, $R_{13b}$, $R_{14a}$, $R_{14b}$, $R_{15a}$, $R_{15b}$, $R_{16a}$, $R_{16b}$, $R_{17a}$, $R_{17b}$, $R_{18a}$, and $R_{18b}$ may each independently be the same as described in connection with $R_{11}$ in Formula 10, $ET_a$ and $ET_b$ may each independently be the same as described in connection with ET in Formula 10, $HT_a$ and $HT_b$ may each independently be the same as described in connection with HT in Formula 10, $L_{11a}$ and $L_{11b}$ are each independently the same as described in connection with in Formula 10, $L_{12a}$ and $L_{12b}$ are each independently the same as described in connection with $L_{12}$ in Formula 10, $a_{11a}$ and $a_{11b}$ are each independently the same as described in connection with $a_{11}$ in Formula 10, and $a_{12a}$ and $a_{12b}$ are each independently the same as described in connection with $a_{12}$ in Formula 10.

In one or more embodiments, the condensed cyclic compound may be selected from Compounds 1-1 to 1-24 and 2-1 to 2-14, but embodiments of the present disclosure are not limited thereto:

1-1
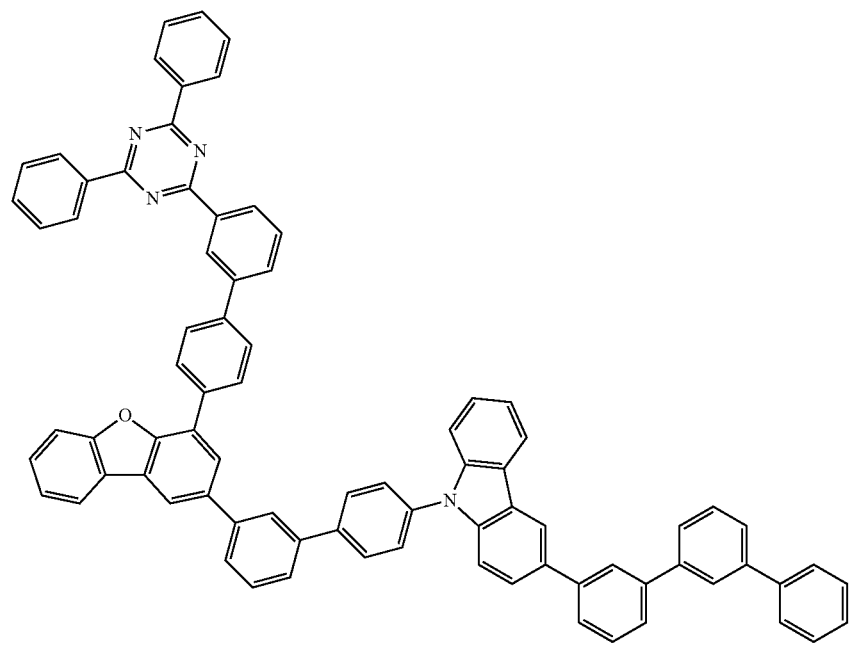
1-2
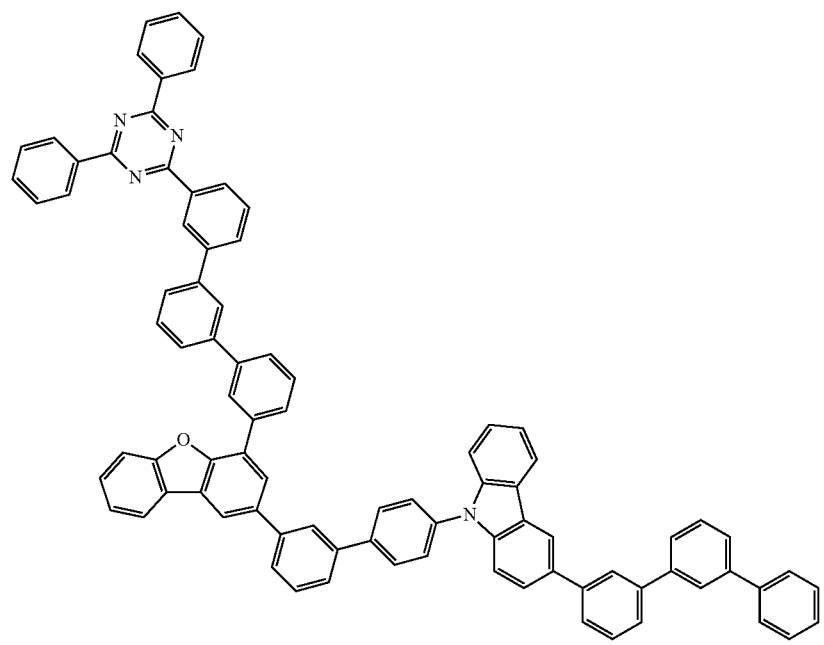

1-3
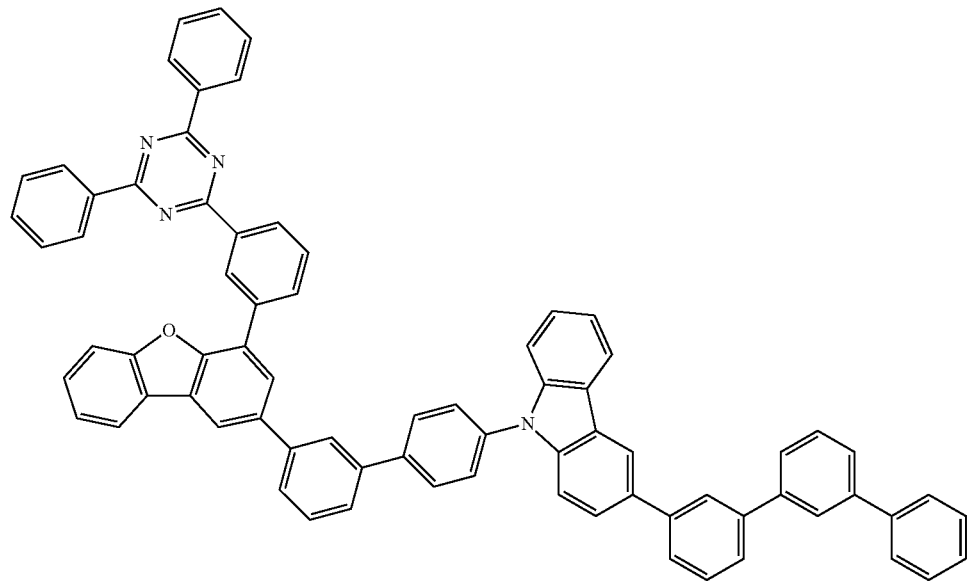
1-4
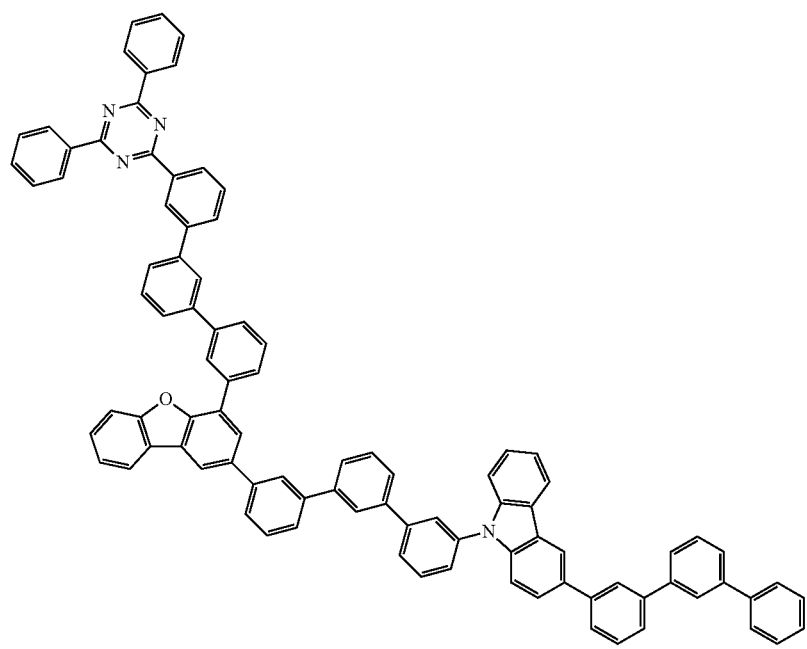

-continued
1-5
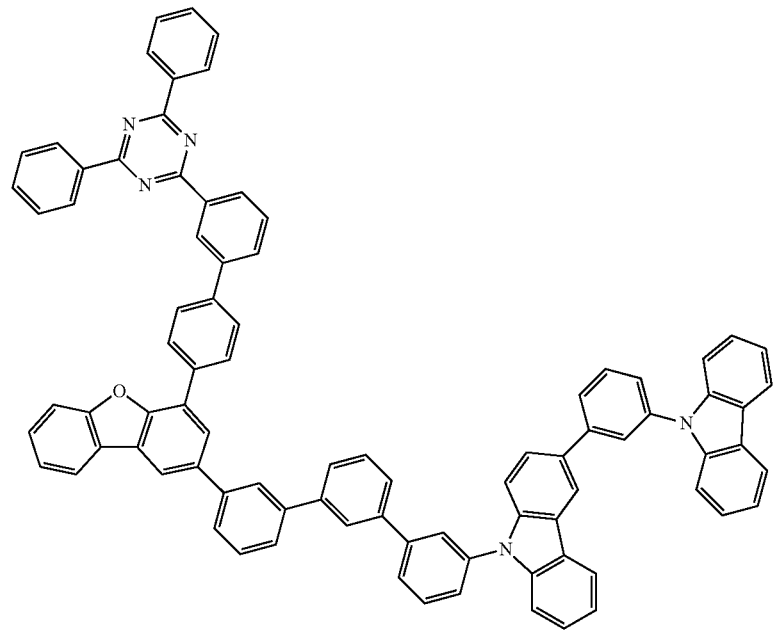
1-6
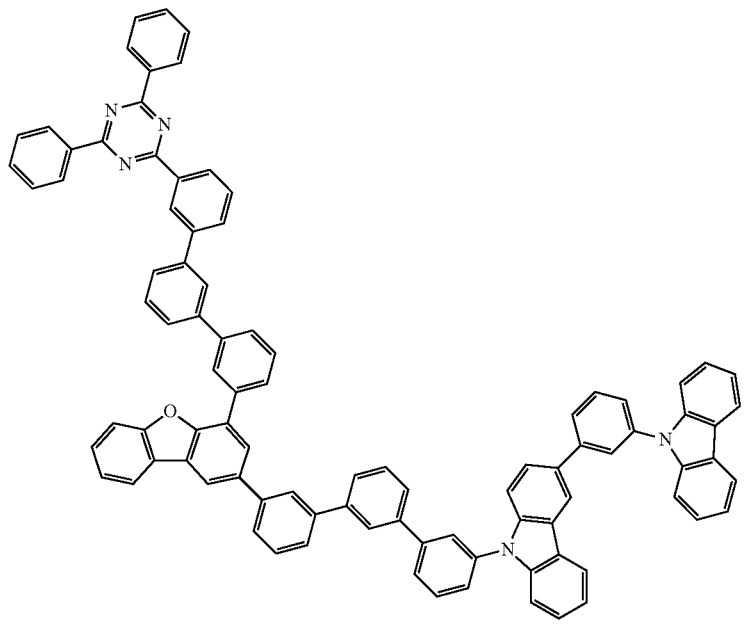

1-7
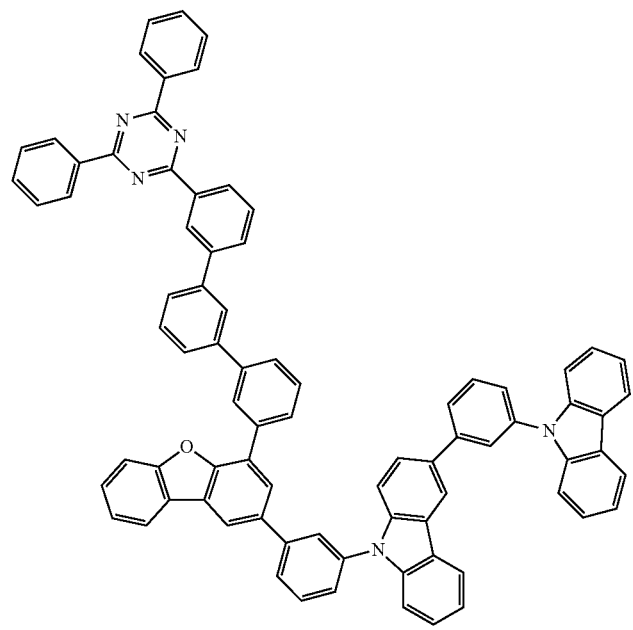
1-8
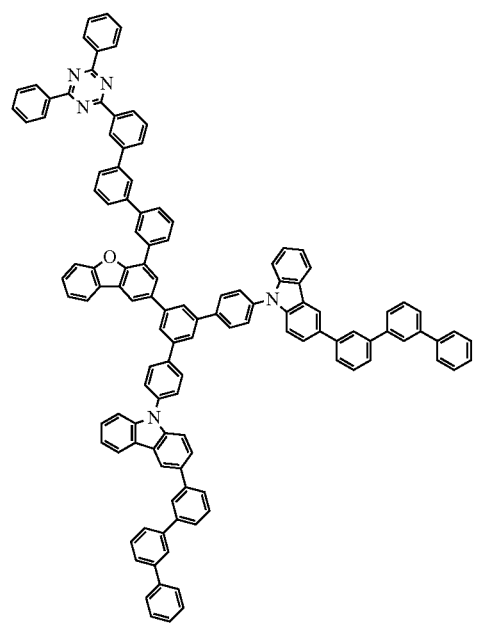

-continued
1-9
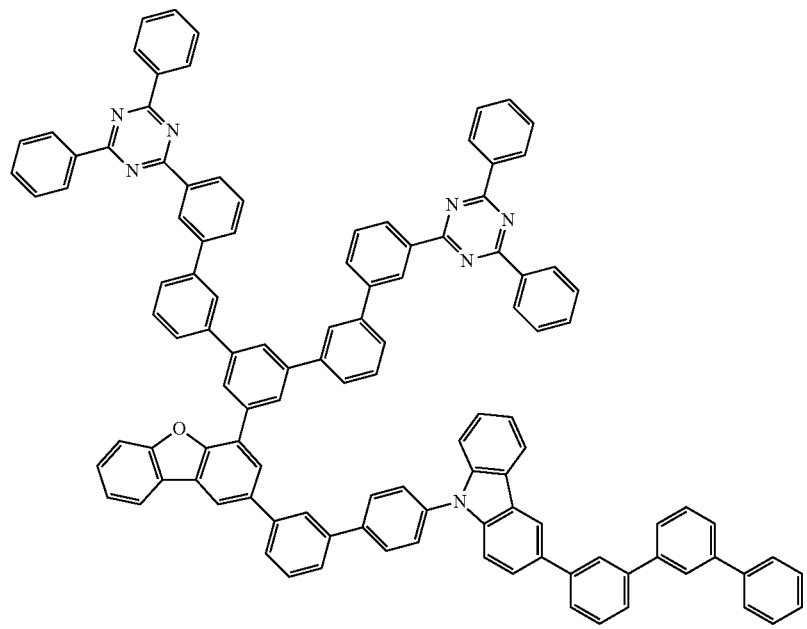
1-10
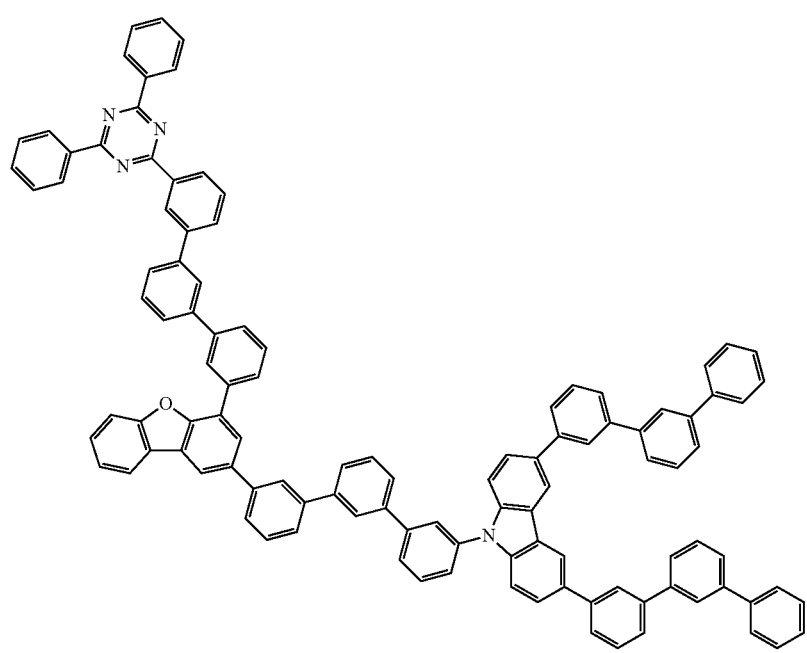

1-11
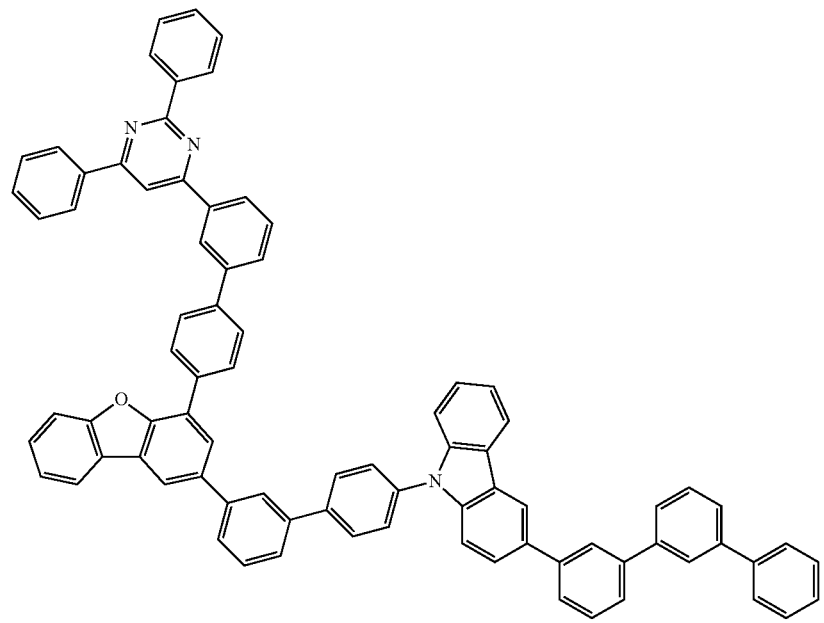
1-12
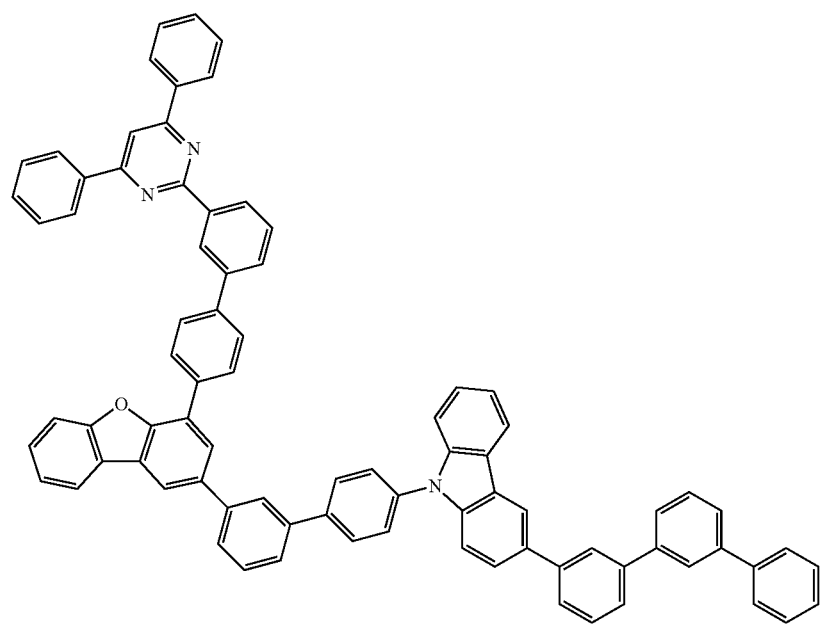

1-13
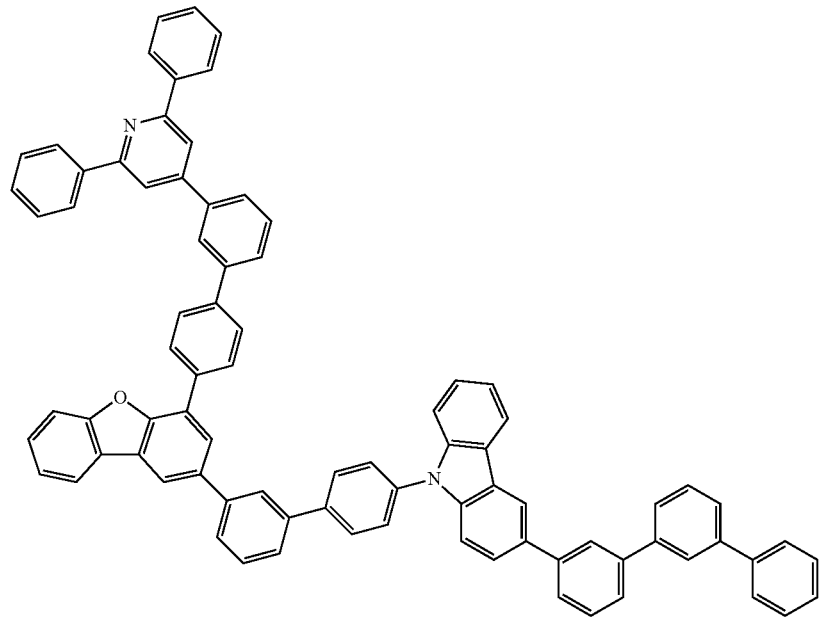
1-14
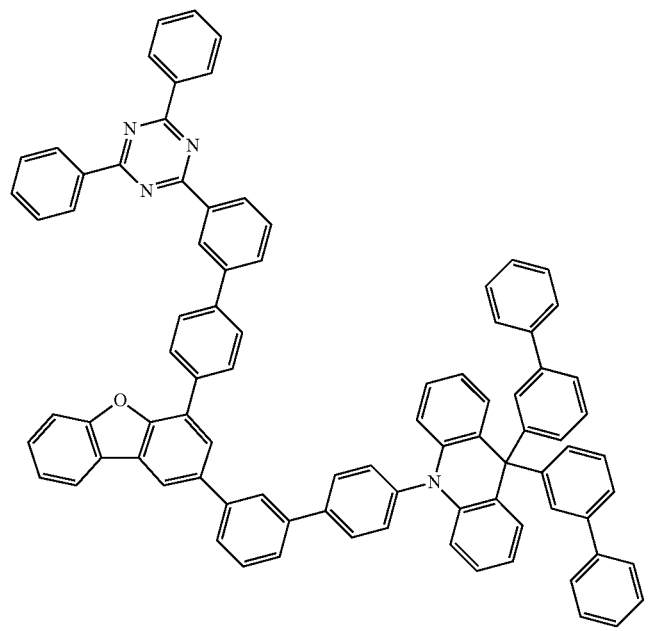

1-15
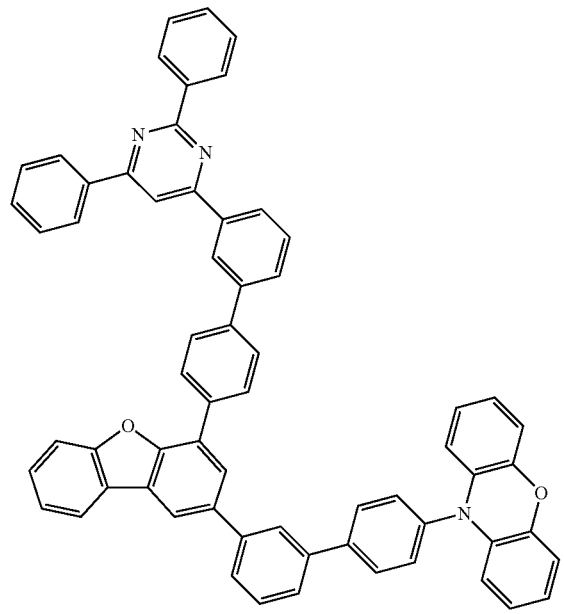
1-16
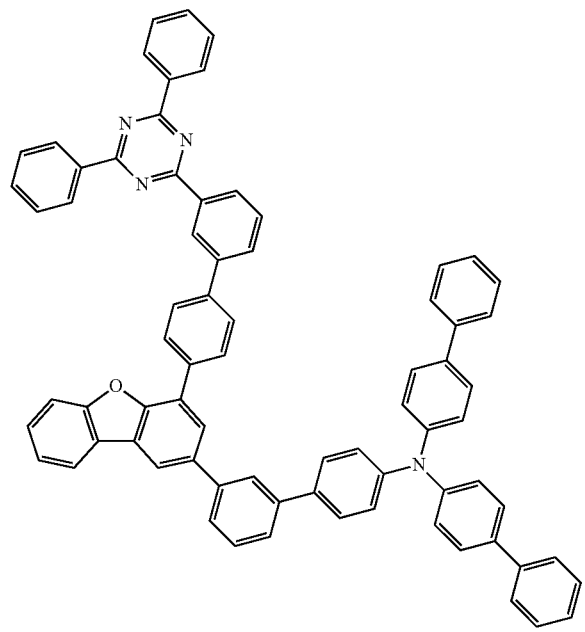

-continued
1-17
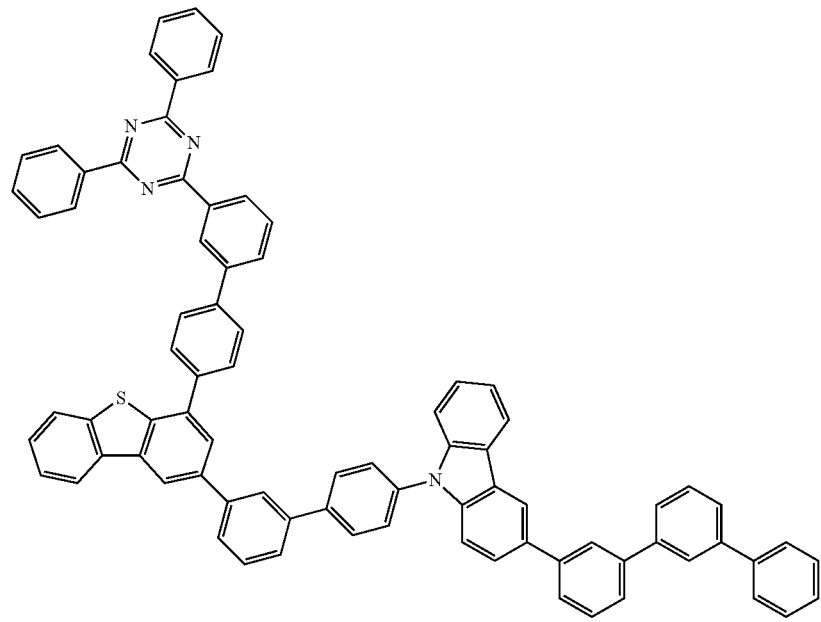
1-18
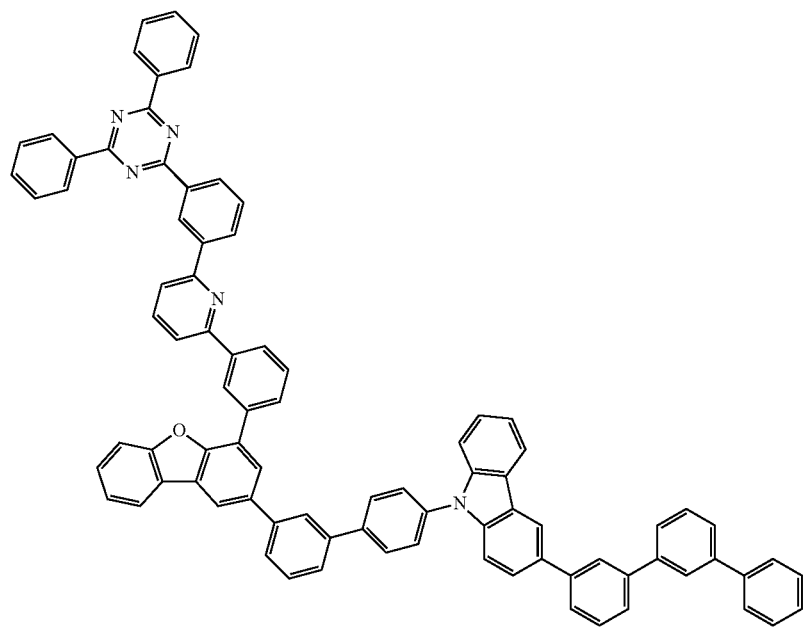

-continued
1-19
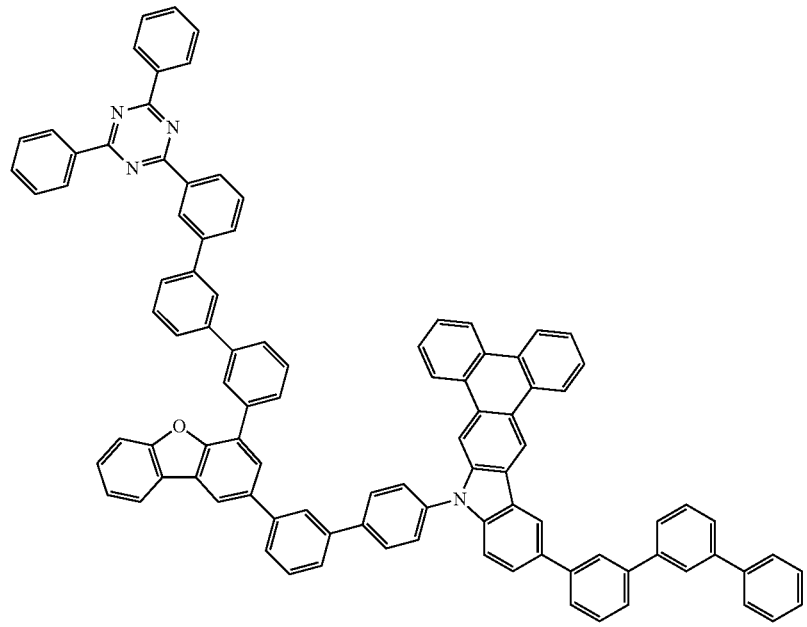
1-20
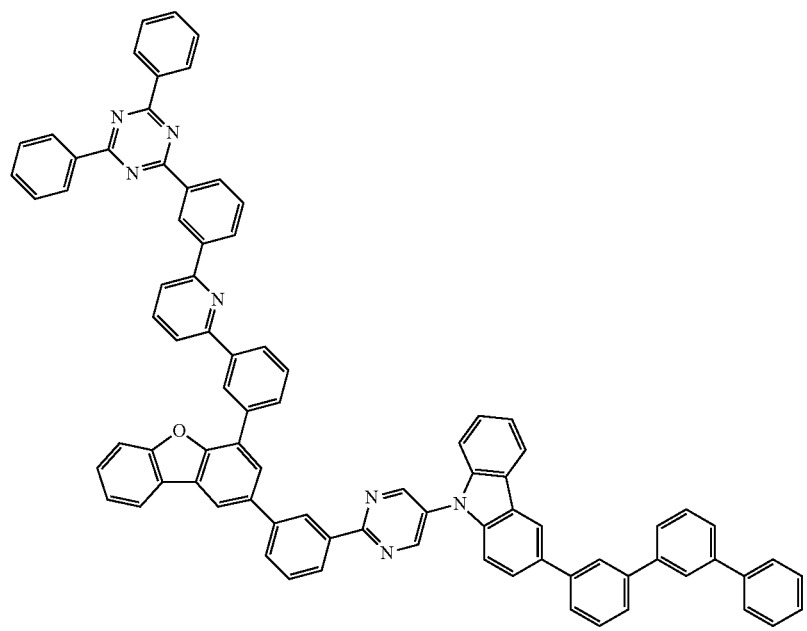

1-21
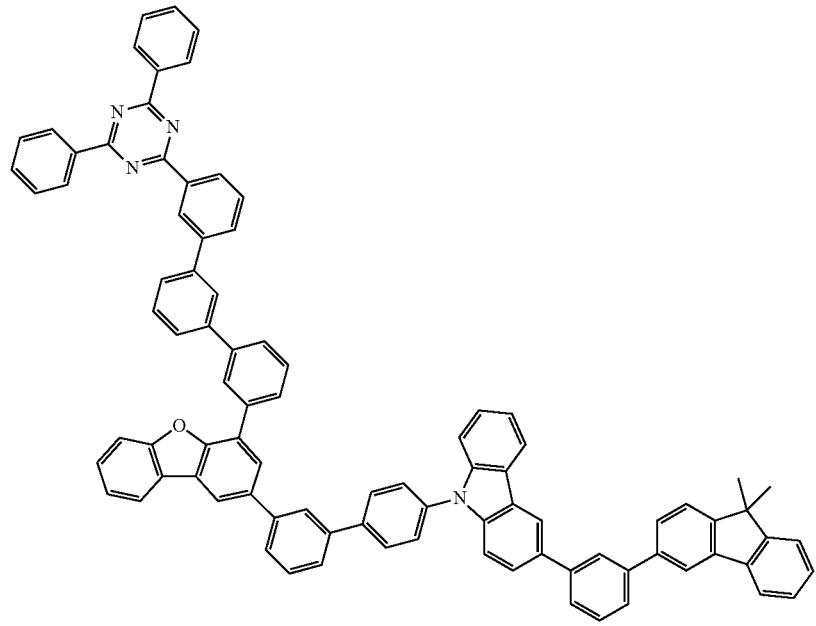
1-22
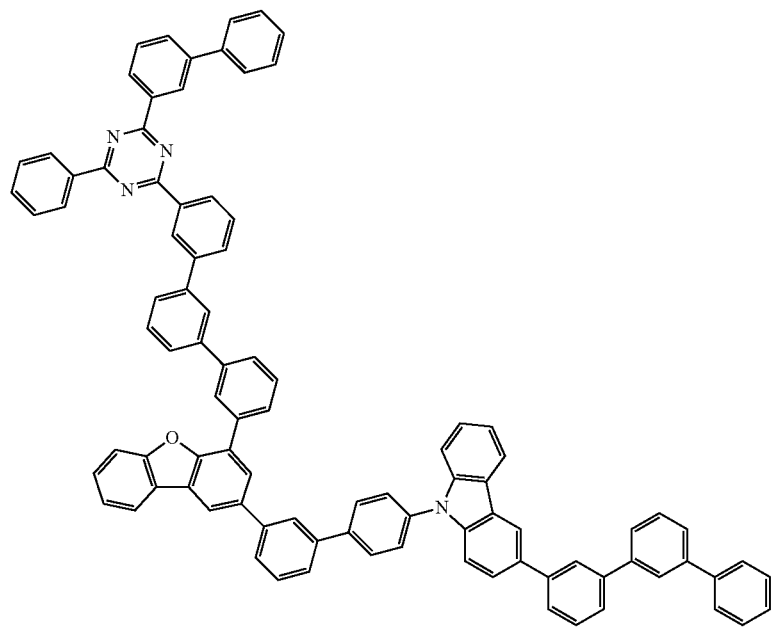

-continued
1-23
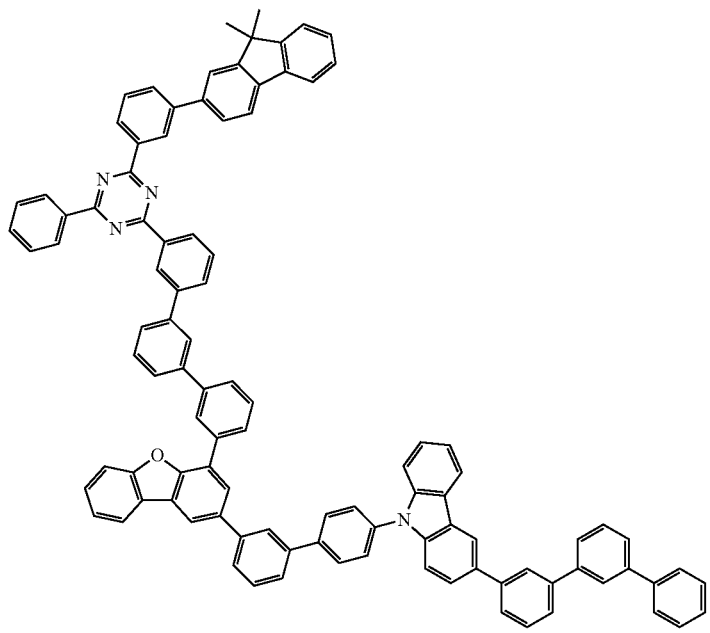
1-24
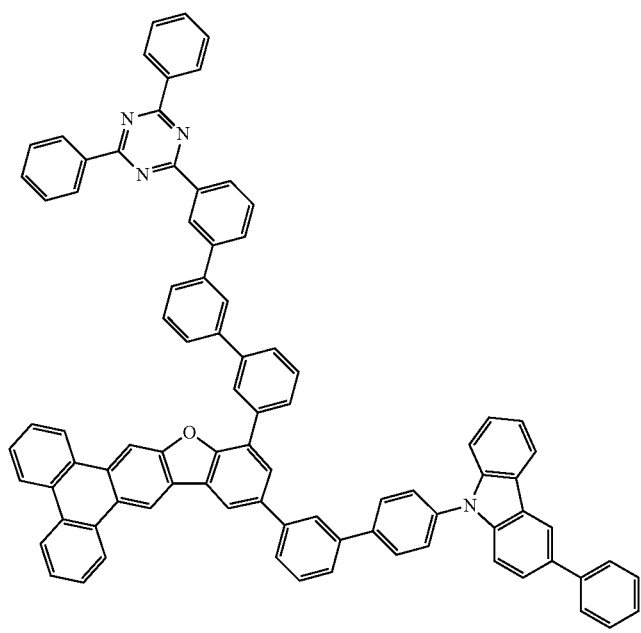

-continued
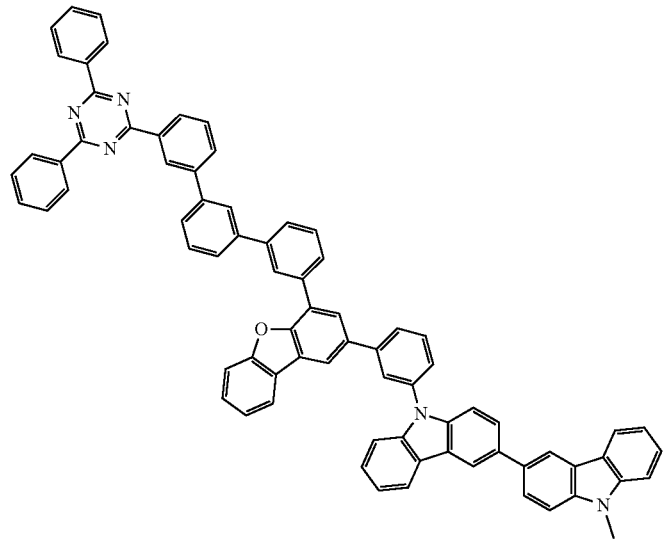
2-1
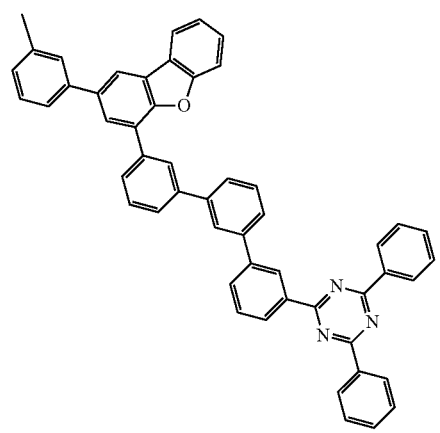
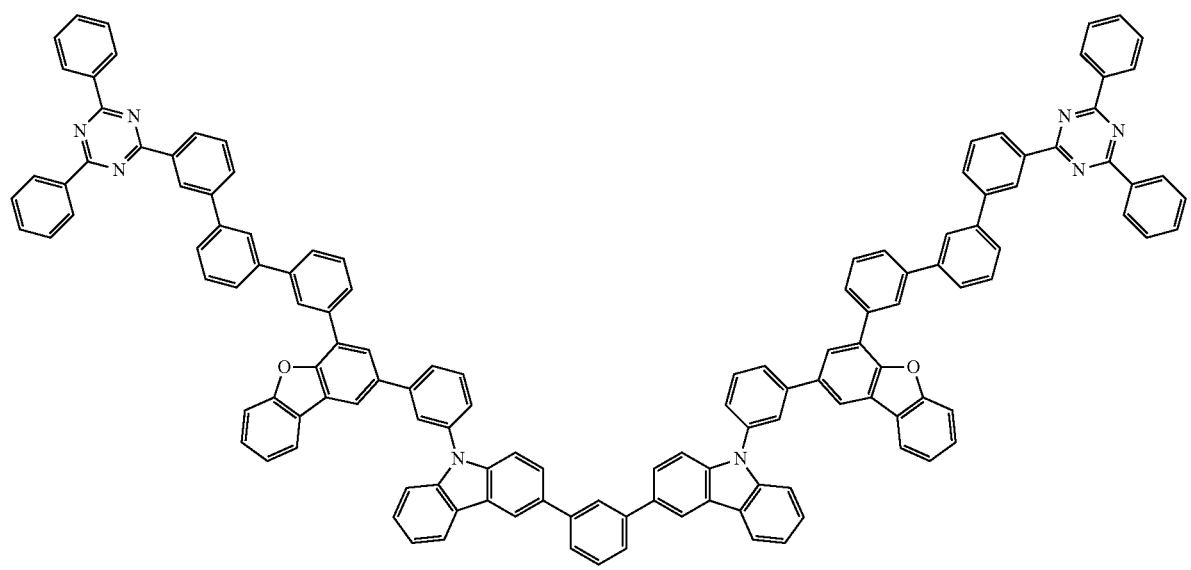
2-2

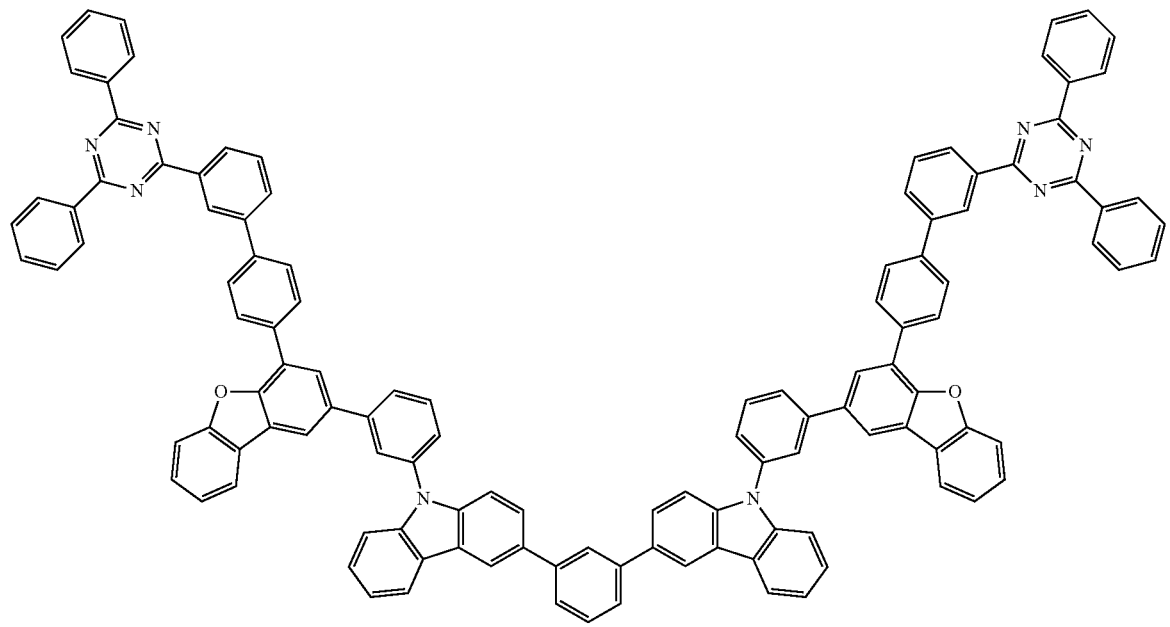
2-3
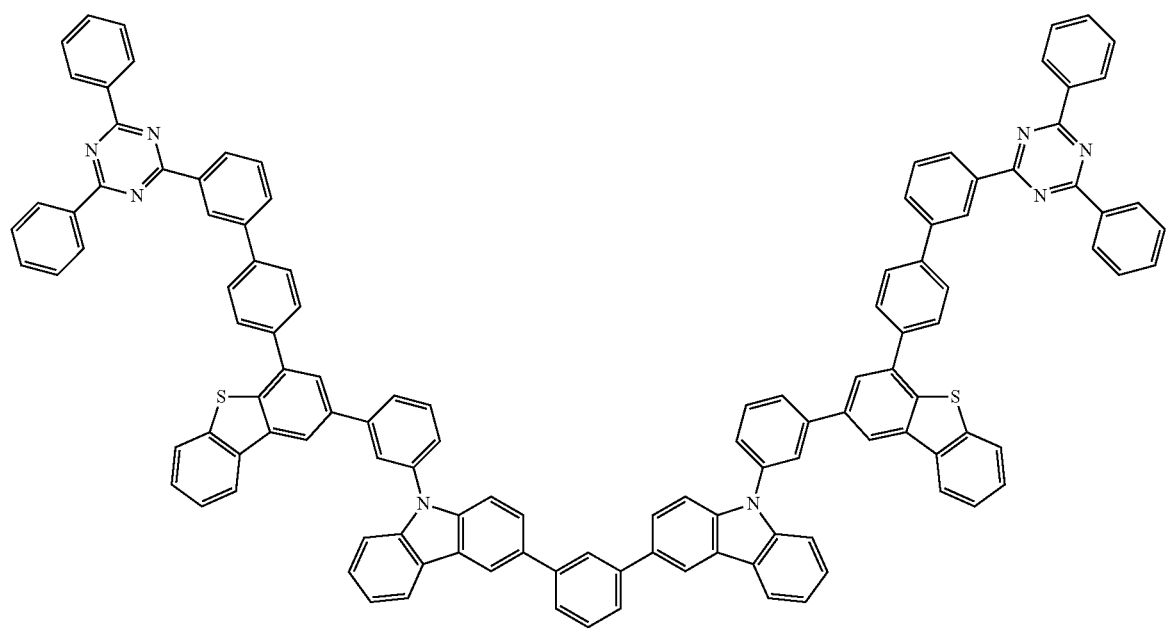
2-4

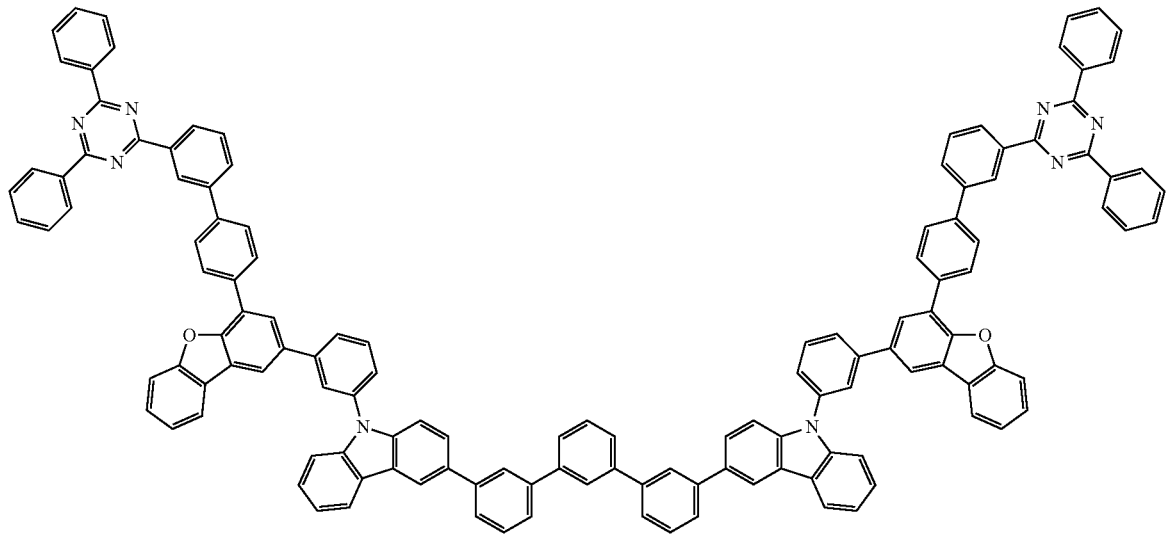
2-5
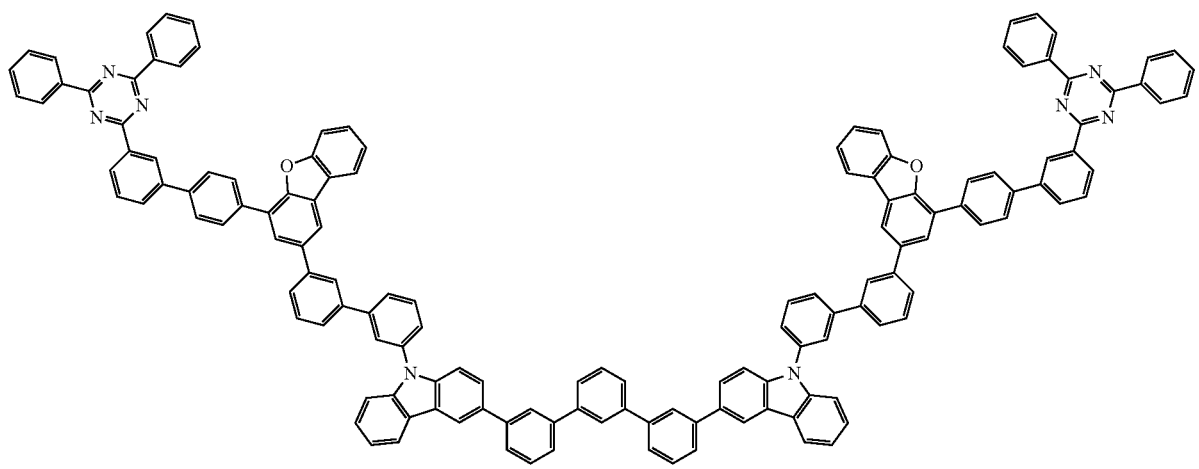
2-6
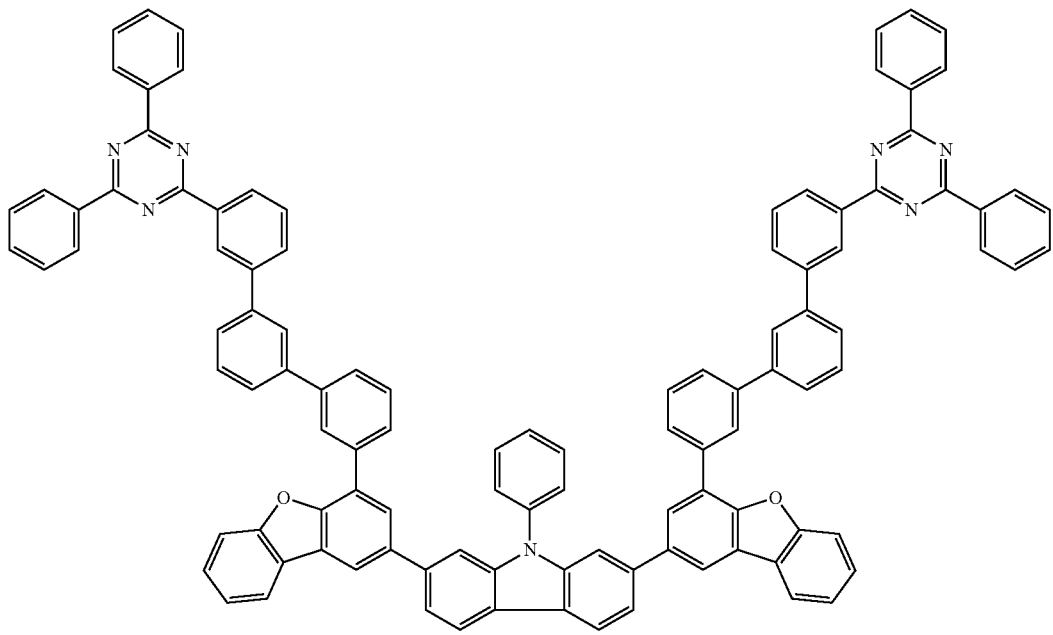
2-7

2-8
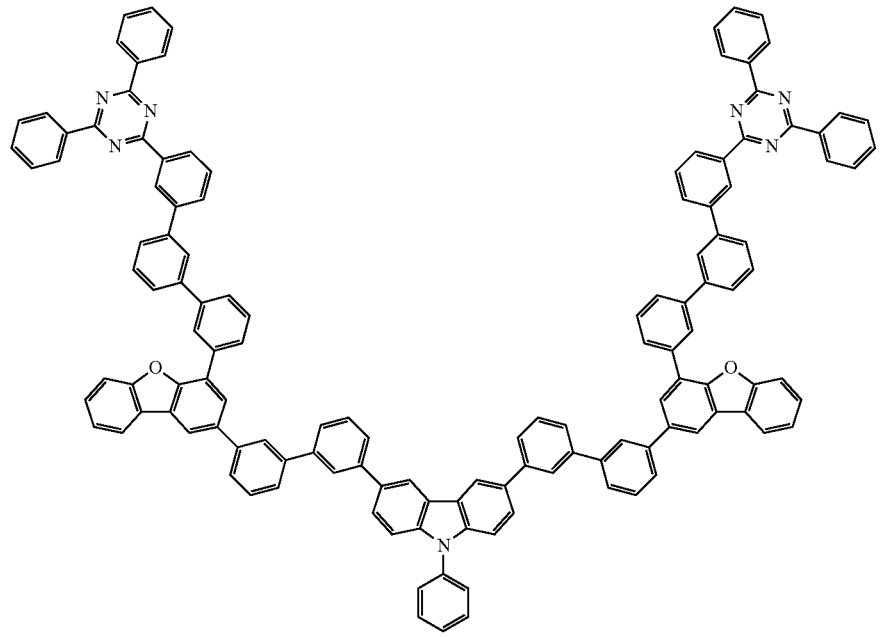
2-9
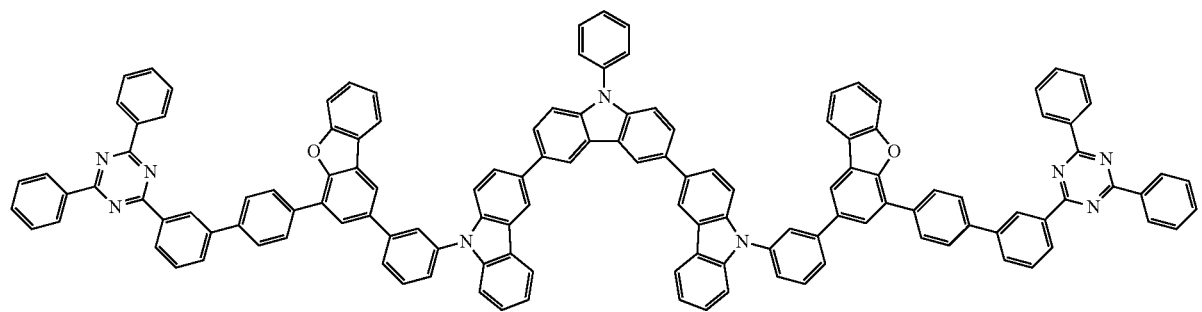
2-10
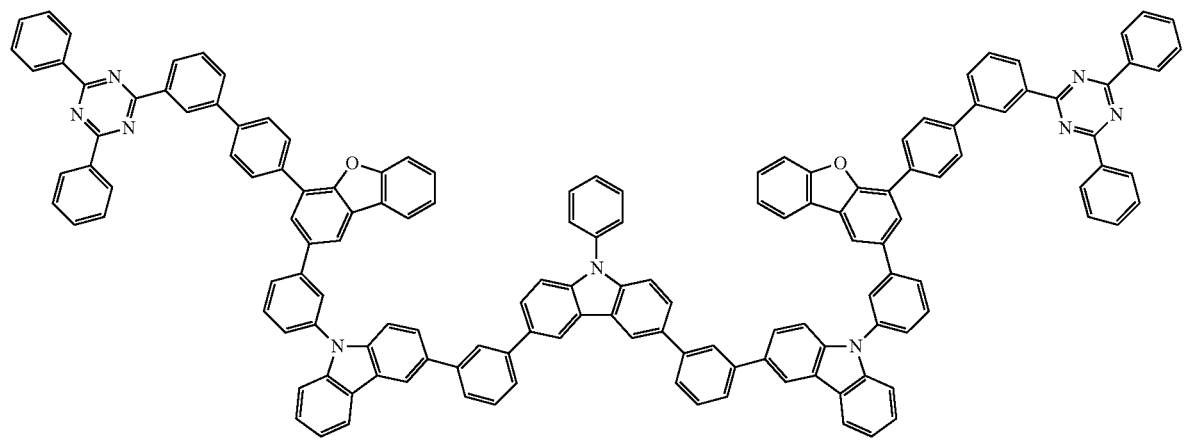

2-11
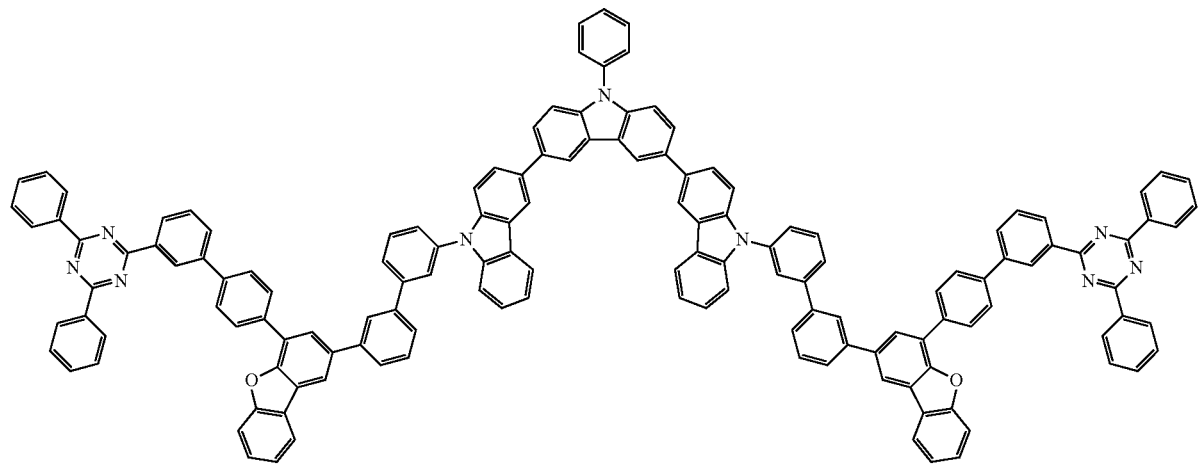
2-12
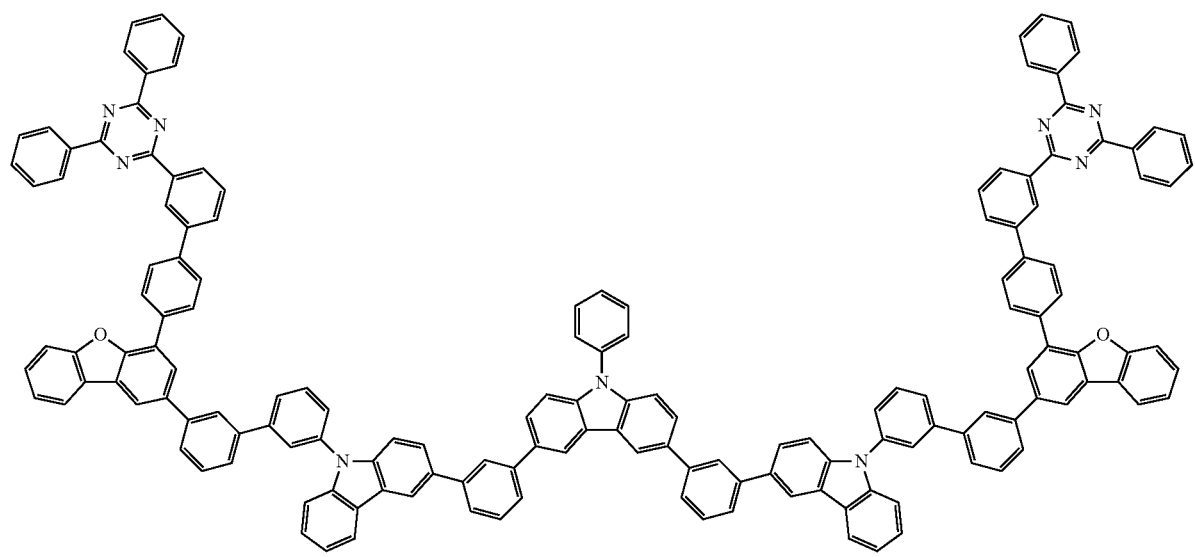
2-13
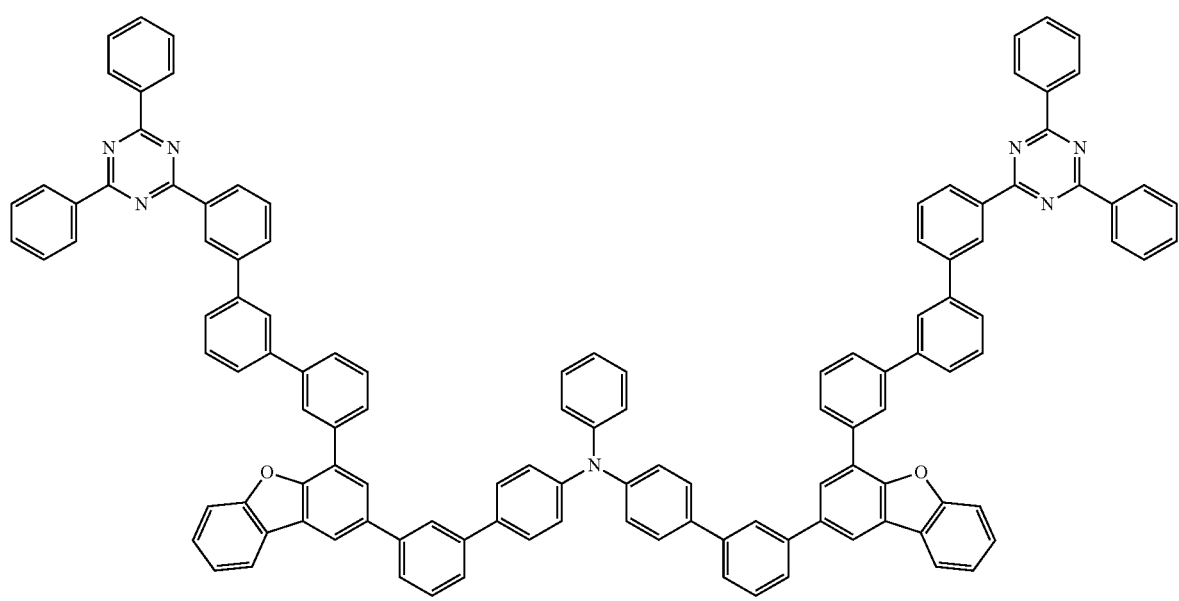

-continued 2-14

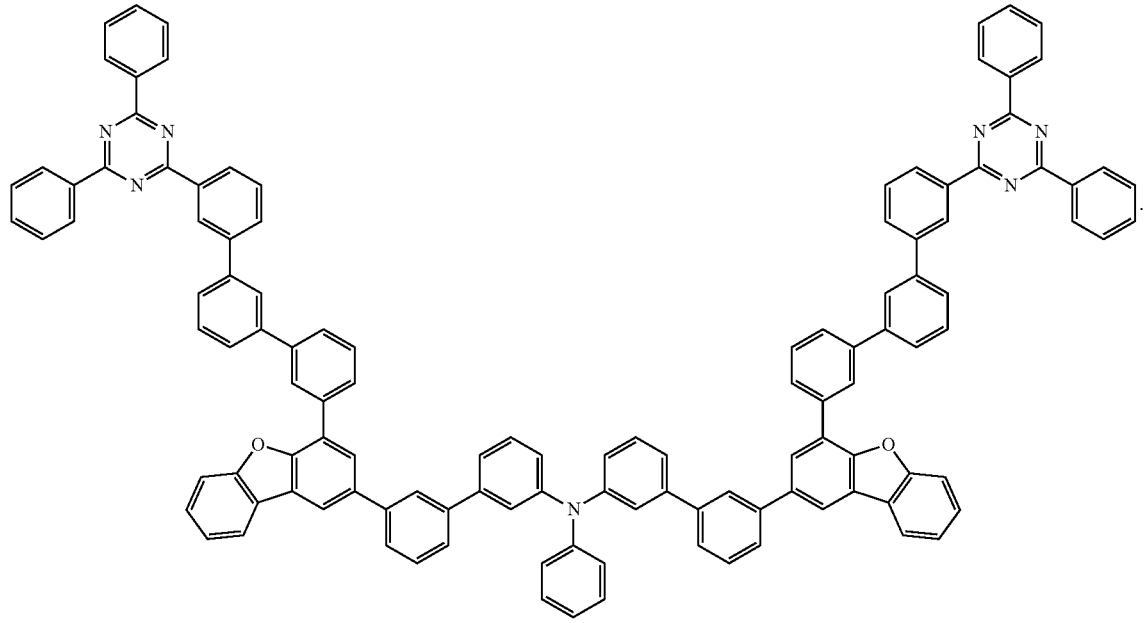

Compounds 1-1 to 1-24 correspond to an embodiment in which n in Formula 1 is 1, and Compounds 2-1 to 2-14 correspond to an embodiment in which n Formula 1 is 2.

The condensed cyclic compound represented by Formula 1 may be included in an organic layer disposed between a pair of electrodes of an organic light-emitting device. For example, the condensed cyclic compound represented by Formula 1 may be included in an emission layer and may be suitable as a host. In an embodiment, the condensed cyclic compound represented by Formula 1 may be suitable as a charge transport material.

The condensed cyclic compound represented by Formula 1 may be synthesized by using a known organic synthesis method. A method of synthesizing the condensed cyclic compound represented by Formula 1 can be understood by a person skilled in the art by referring to Examples provided below.

Composition

Hereinafter, a composition according to an embodiment will be described in detail.

The composition may include at least one of the condensed cyclic compound described above.

For example, the composition may further include at least one of a first compound represented by one selected from Formulae 5 and 6:

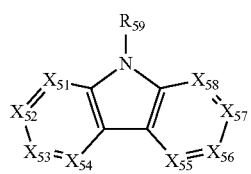

Formula 5

-continued

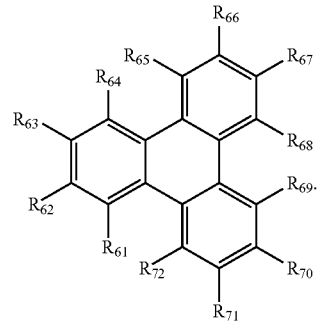

Formula 6

In Formulae 5 and 6, $X_{51}$ may be N or $C(R_{51})$, $X_{52}$ may be N or $C(R_{52})$; $X_{53}$ may be N or $C(R_{53})$; $X_{54}$ may be N or $C(R_{54})$; $X_{55}$ may be N or $C(R_{55})$, $X_{56}$ may be N or $C(R_{56})$, $X_{57}$ may be N or $C(R_{57})$; and $X_{58}$ may be N or $C(R_{58})$, $R_{51}$ to $R_{58}$ and $R_{61}$ to $R_{72}$ may each independently be selected from hydrogen, deuterium, a substituted or unsubstituted $C_6$-$C_{60}$ aryl group, a substituted or unsubstituted heteroaryl group, a substituted or unsubstituted monovalent non-aromatic condensed polycyclic group, and a substituted or unsubstituted monovalent non-aromatic condensed heteropolycyclic group, and $R_{59}$ may be selected from a substituted or unsubstituted aryl group having 6 to 60 ring-forming carbon atoms, a substituted or unsubstituted heteroaryl group having 5 to 60 ring-forming atoms, a substituted or unsubstituted monovalent non-aromatic condensed polycyclic group, and a substituted or unsubstituted monovalent non-aromatic condensed heteropolycyclic group.

For example, in Formulae 5 and 6, two neighboring groups selected from $R_{51}$ to $R_{55}$ and $R_{61}$ to $R_{72}$ may optionally be linked to form a ring, but embodiments of the present disclosure are not limited thereto.

When the composition includes the condensed cyclic compound and the first compound, the composition may be excellent in terms of electron injection and/or electron transport, and the composition may be used for an electron injection layer, an electron transport layer, and/or an emission layer of an organic light-emitting device.

The composition may further include a light-emitting material.

The light-emitting material is not particularly limited as long as the light-emitting material has a light-emitting function, and may be a fluorescent dopant, a phosphorescent dopant, a quantum dot, or the like. For example, the light-emitting material may be a phosphorescent dopant, but embodiments of the present disclosure are not limited thereto.

The fluorescent dopant is a compound that can emit light from singlet exciton. For example, the fluorescent dopant may be a perylene and a derivative thereof, a rubrene and a derivative thereof, a coumarin and a derivative thereof, or a 4-dicyanomethylene-2-(p-dimethylaminostyryl)-6-methyl-4H-pyran (DCM) and a derivative thereof, but embodiments of the present disclosure are not limited thereto.

The phosphorescent dopant is a compound that can emit light from triplet exciton, and may be an organometallic compound. For example, the phosphorescent dopant may be an iridium complex, such as bis[2-(4,6-difluorophenyl)pyridinate]picolinate iridium(III) (Flrpic), bis(1-phenylisoquinoline)(acetylacetonate) iridium(III) (Ir(piq)$_2$(acac)), tris(2-phenylpyridine) iridium(III) (Ir(ppy)$_3$), or tris(2-(3-p-xylyl)phenyl)pyridine iridium(III) (dopant), an osmium complex, a platinum complex, or the like, but embodiments of the present disclosure are not limited thereto.

The quantum dot may be a nanoparticle including group II-VI semiconductor, group III-V semiconductor, or group IV-IV semiconductor. For example, the quantum dot may be CdO, CdS, CdSe, CdTe, ZnO, ZnS, ZnSe, ZnTe, HgS, HgSe, HgTe, MgSe, MgS CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, GaN, GaP, GaAs, AlN, AlP, AlAs, InN, InP, InAs, InSb, GaNP, GaNAs, GaNSb, GaPAs, GaPSb, AlNP, AlNAs, AlNSb, AlPAs, AlPSb, InNP, InNAs, InPAs, InPSb, GaAlNP, SnS, SnSe, SnTe, PbS, PbSe, PbTe, SnSeS, SnSeTe, SnSTe, PbSeS, PbSeTe, PbSTe, SnPbS, SnPbSe, SnPbTe, or the like, but embodiments of the present disclosure are not limited thereto. In addition, the diameter of the quantum dot is not particularly limited, but may be in a range of about 1 nanometer (nm) to about 20 nm. The quantum dot may be a single core structure, or may be a core-shell structure.

The composition may further include a solvent.

The solvent is not particularly limited as long as the solvent is dissolved in the condensed cyclic compound represented by Formula 1.

For example, the solvent may be ketone, aliphatic ester, an aromatic ester, a halogenated hydrocarbon, a non-fluorinated alcohol, fluorinated alcohol, aliphatic hydrocarbon, an aromatic hydrocarbon, or an aromatic hydrocarbon substituted compound, but embodiments of the present disclosure are not limited thereto.

In an embodiment, the solvent may be toluene, xylene, ethylbenzene, diethylbenzene, mesitylene, propylbenzene, cyclohexylbenzene, dimethoxybenzene, anisole, ethoxytoluene, phenoxytoluene, iso-propylbiphenyl, dimethylanisole, phenyl acetate, phenyl propionic acid, methyl benzoate, ethyl benzoate, or the like, but embodiments of the present disclosure are not limited thereto.

The solvent may be an aromatic ester, and for example, may be methyl benzoate or ethyl benzoate, but embodiments of the present disclosure are not limited thereto.

The concentration of the composition is not particularly limited, and may be appropriately controlled according to the purpose thereof.

In the composition, the concentration of the condensed cyclic compound represented by Formula 1 may be in a range of about 0.1 weight % to about 20 weight %, and for example, in a range of about 0.5 weight % to about 10 weight %, but embodiments of the present disclosure are not limited thereto. When the concentration of the condensed cyclic compound is within this range, the coatability may be improved.

Therefore, the composition may be used as a material for forming a light-emitting device (for example, an organic light-emitting device, a quantum dot light-emitting device, or the like). For example, the composition may be used for an emission layer, a charge injection layer, and/or a charge transport layer of a light-emitting device. In another example, the composition may be used for an emission layer of a light-emitting device. In yet another example, the composition may be used when a light-emitting device is manufactured by using solution coating. At this time, the current efficiency and light-emitting lifespan of the light-emitting device may be improved.

Organic Light-Emitting Device

Hereinafter, an organic light-emitting device according to an embodiment will be described in detail with reference to the FIGURE. The FIGURE is a schematic cross-sectional view of an organic light-emitting device according to an embodiment.

The organic light-emitting device 100 according to the embodiment may include a substrate 110, a first electrode 120 on the substrate 110, a hole injection layer 130 on the first electrode 120, a hole transport layer 140 on the hole injection layer 130, an emission layer 150 on the hole transport layer 140, an electron transport layer 160 on the emission layer 150, an electron injection layer 170 on the electron transport layer 160, and a second electrode 180 on the electron injection layer 170.

The condensed cyclic compound represented by Formula 1, may be included in, for example, an organic layer disposed between the first electrode 120 and the second electrode 180 (for example, one selected from the hole injection layer 130, the hole transport layer 140, the emission layer 150, the electron transport layer 160, and the electron injection layer 170). For example, the condensed cyclic compound represented by Formula 1 may be included in the emission layer 150 as a host. Alternatively, the condensed cyclic compound represented by Formula 1 may be included in another organic layer other than the emission layer 150. For example, the condensed cyclic compound represented by Formula 1 may be included in the electron transport layer 160 and/or the electron injection layer 170 as a charge transport material.

The term "organic layer" as used herein refers to a single layer and/or a plurality of layers between the first electrode and the second electrode of the organic light-emitting device. The "organic layer" may include, in addition to an organic compound, an organometallic compound including metal.

The expression "(an organic layer) includes at least one organometallic compound" as used herein may include a case in which "(an organic layer) includes identical compounds represented by Formula 1" and a case in which "(an organic layer) includes two or more different condensed cyclic compounds represented by Formula 1."

For example, the organic layer may include, as the condensed cyclic compound, only Compound 1-1. In this regard, Compound 1-1 may be included only in the emission layer of the organic light-emitting device. In one or more embodiments, the organic layer may include, as the condensed cyclic compound, Compound 1-1 and Compound 1-2. In this regard, Compound 1-1 and Compound 1-2 may be included in an identical layer (for example, Compound 1 and Compound 2 all may exist in an emission layer).

The substrate 110 may be any substrate that is used in an organic light-emitting device according to the related art. For example, the substrate 110 may be a glass substrate, a silicon substrate, or a transparent plastic substrate, each having excellent mechanical strength, thermal stability, surface smoothness, ease of handling, and water resistance, but embodiments of the present disclosure are not limited thereto.

The first electrode 120 may be formed on the substrate 110. The first electrode 120 may be, for example, an anode, and may be formed of a material with a high work function to facilitate hole injection, such as an alloy or a conductive compound. The first electrode 120 may be a reflective electrode, a semi-transmissive electrode, or a transmissive electrode. The first electrode 120 may have a single-layered structure or a multi-layered structure including two or more layers. For example, the first electrode 120 may be a transparent electrode formed of indium tin oxide (ITO), indium zinc oxide (IZO), tin oxide (SnO2), or zinc oxide (ZnO), which has excellent transparency and conductivity. On the transparent first electrode 120, magnesium (Mg), aluminum (Al), aluminum-lithium (Al—Li), calcium (Ca), magnesium-indium (Mg—In), or magnesium-silver (Mg—Ag) may be disposed, so as to form a reflective electrode. In an embodiment, the first electrode 120 may have a three-layered structure of ITO/Ag/ITO, but embodiments of the present disclosure are not limited thereto.

The hole transport region may be disposed on the first electrode 120.

The hole transport region may include at least one selected from selected from a hole injection layer 130, a hole transport layer 140, an electron blocking layer (not shown), and a buffer layer (not shown).

The hole transport region may include only either a hole injection layer 130 or a hole transport layer 140. In an embodiment, the hole transport region may have a hole injection layer/hole transport layer structure or a hole injection layer/hole transport layer/electron blocking layer structure, wherein for each structure, constituting layers are sequentially stacked from the first electrode 120 in the stated order.

The hole injection layer 130 may include at least one selected from, for example poly(ether ketone)-containing triphenylamine (TPAPEK), 4-iso-propyl-4'-methyldiphenyliodonium tetrakis(pentafluorophenyl) borate (PPBI), N,N'-diphenyl-N,N'-bis-[4-(phenyl-m-tolyl-amino)-phenyl]-biphenyl-4,4'-diamine (DNTPD), copper phthalocyanine, 4,4',4"-tris(3-methylphenylphenylamino) triphenylamine (m-MTDATA), N,N'-di(1-naphthyl)-N,N'-diphenylbenzidine (NPB), 4,4',4"-tris(diphenylamino) triphenylamine (TDATA), 4,4',4"-tris(N,N-2-naphthylphenylamino) triphenylamine (2-TNATA), polyaniline/dodecylbenzene sulphonic acid (PANI/DBSA), poly(3,4-ethylenedioxythiophene)/poly(4-styrene sulfonate) (PEDOT/PSS), polyaniline/10-camphor sulfonic acid (PANI/CSA), and polyaniline/poly(4-styrene sulfonate) (PANI/PSS).

The hole injection layer 130 may be formed to a thickness in a range of about 10 nm to about 1,000 nm, for example, about 10 nm to about 100 nm.

The hole transport layer 140 may include at least one selected from, for example, a carbazole derivative, such as 1,1-bis[(di-4-tolylamino)phenyl]cyclohexane (TAPC), N-phenylcarbazole, and polyvinylcarbazole, N, N'-bis(3-methylphenyl)-N, N'-diphenyl-[1,1-biphenyl]-4,4'-diamine (TPD), 4,4',4"-tris(N-carbazolyl) triphenylamine (TCTA), N, N'-di(1-naphthyl)-N, N'-diphenylbenzidine (NPB), poly (9,9-dioctyl-fluorene-co-N-(4-butylphenyl)-diphenylamine (TFB), P-1, and FA-14:

P-1

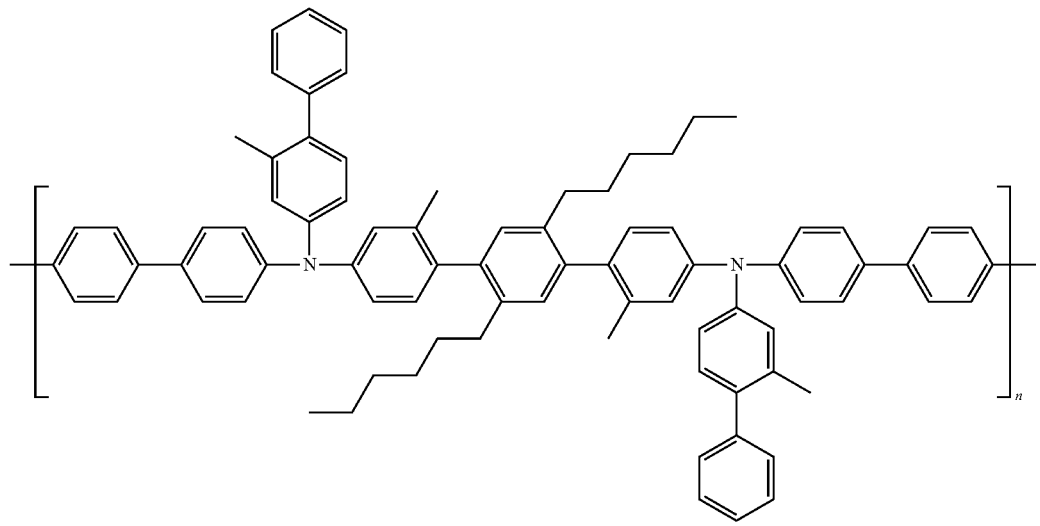

Number average molecular weight $M_n$=141,000.
Weight average molecular weight $M_w$=511,000.

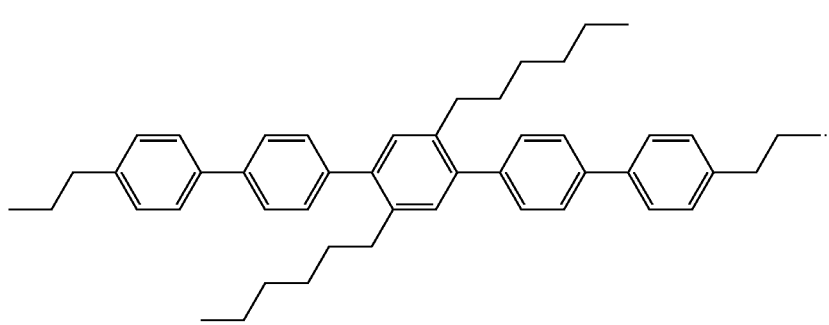

FA-14

The hole transport layer 140 may be formed to a thickness in a range of about 10 nm to about 1,000 nm, for example, about 10 nm to about 150 nm.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 or Compound HT-D2, but are not limited thereto.

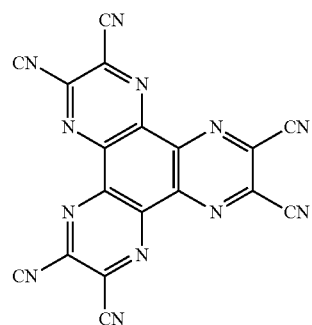

HT-D1

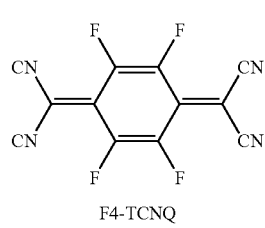

F4-TCNQ

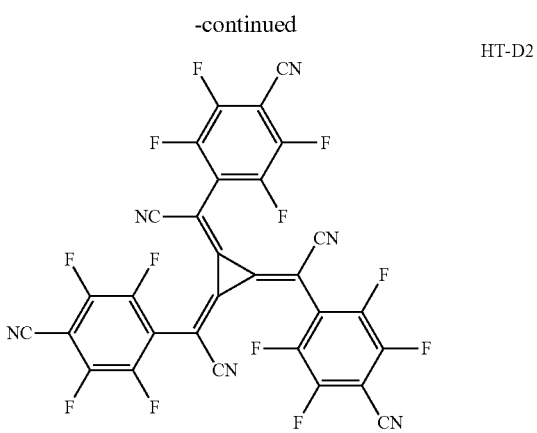

HT-D2

Meanwhile, when the hole transport region includes a buffer layer, a material for the buffer layer may be selected from materials for the hole transport region described above and materials for a host to be explained later. However, the material for the electron blocking layer is not limited thereto.

In addition, when the hole transport region includes an electron blocking layer, a material for the electron blocking layer may be selected from materials for the hole transport region described above and materials for a host to be explained later. However, the material for the electron blocking layer is not limited thereto. For example, when the hole transport region includes an electron blocking layer, a material for the electron blocking layer may be mCP.

The mission layer 150 may be formed on the hole transport region. The emission layer 150 is a layer that emits light by fluorescence or phosphorescence. The emission layer 150 may include a host and/or a dopant, and when included, the host may include the condensed cyclic compound represented by Formula 1. In addition, the host and/or the dopant included in the emission layer 150 may be known materials.

For example, the host may include tris(8-quinolinato) aluminium ($Alq_3$), 4,4'-bis(carbazol-9-yl)biphenyl (CBP), poly(n-vinylcarbazole) (PVK), 9,10-di(naphthalene)anthracene (ADN), 4,4',4''-tris(N-carbazolyl)triphenylamine (TCTA), 1,3,5-tris(N-phenyl-benzimidazol-2-yl)benzene (TPBi) 3-tert-butyl-9,10-di(naphth-2-yl)anthracene (TBADN), distyrylarylene (DSA), 4,4'-bis(9-carbazole)-2,2'-dimethyl-bipheny (dmCBP), HT-Host-A, or HT-Host-B, but embodiments of the present disclosure are not limited thereto:

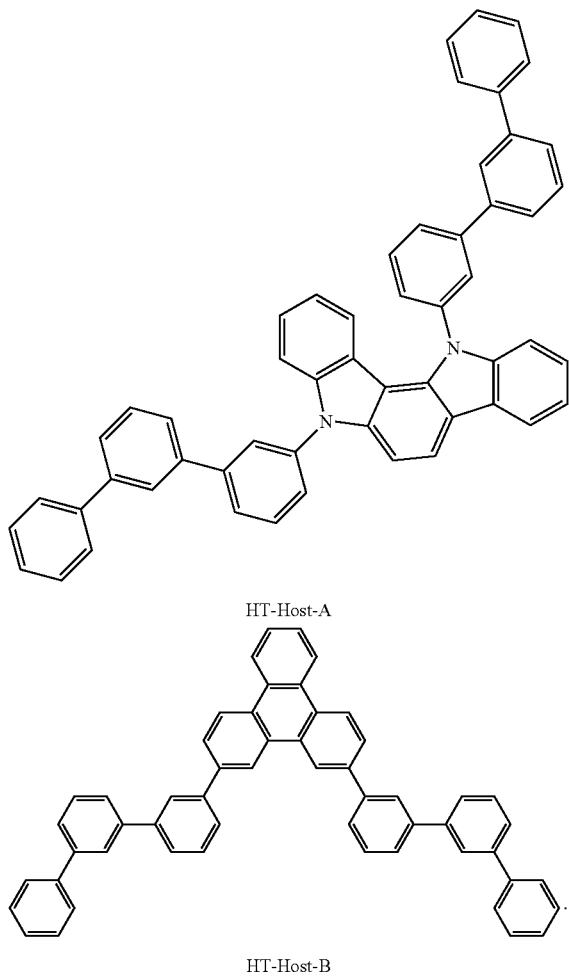

HT-Host-A

HT-Host-B

For example, the dopant may include a perylene and a derivative thereof, a rubrene and a derivative thereof, a coumarin and a derivative thereof, 4-dicyanomethylene-2-(p-dimethylaminostyryl)-6-methyl-4H-pyran (DCM) and a derivative thereof, an iridium complex, such as bis[2-(4,6-difluorophenyl)pyridinate]picolinate iridium (III) (Flrpic), bis(1-phenylisoquinoline)(acetylacetonate) iridium (III) (Ir(piq)$_2$(acac)), tris(2-phenylpyridine) iridium (III) (Ir(ppy)$_3$), tris(2-(3-p-xylyl)phenyl)pyridine iridium (III) (dopant), an osmium complex, or a platinum complex, but embodiments of the present disclosure are not limited thereto.

When the emission layer 150 includes the host and/or the dopant, an amount of the host may be greater than that of the dopant, and an amount of the dopant may be in a range of about 0.01 parts by weight to about 15 parts by weight based on 100 parts by weight of the host, but embodiments of the present disclosure are not limited thereto.

In addition, when the emission layer 150 includes the condensed cyclic compound represented by Formula 1 as an electron transporting host, a ratio of the condensed cyclic compound to the entire host in the emission layer 150 may be in a range of about 1 weight % to about 99 weight %, for example, about 5 weight % to about 95 weight %, for example, about 10 weight % to about 90 weight %, but embodiments of the present disclosure are not limited thereto.

The emission layer 150 may be formed to a thickness in a range about 10 nm to about 60 nm.

When the organic light-emitting device is a full-color organic light-emitting device, the emission layer may be patterned into a red emission layer, a green emission layer, and a blue emission layer. In one or more embodiments, due to a stacked structure including a red emission layer, a green emission layer, and/or a blue emission layer, the emission layer may emit white light.

The electron transport region may be disposed on the emission layer 150.

The electron transport region may include at least one selected from a hole blocking layer (not shown), an electron transport layer 160, and an electron injection layer 170.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

For example, the organic light-emitting device 100 may include, to prevent the excitons or holes from diffusing into the electron transport layer 160, a hole blocking layer disposed between the electron transport layer 160 and the emission layer 150. The hole blocking layer may include, for example, at least one selected from an oxadiazole derivative, a triazole derivative, BCP, Bphen, and BAlq, but a material therefor is not limited thereto.

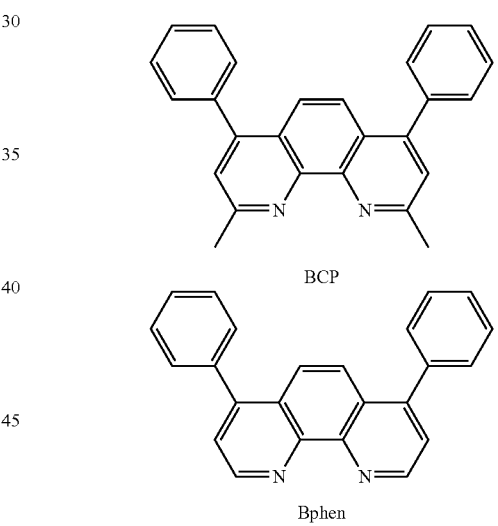

BCP

Bphen

A thickness of the hole blocking layer may be in a range of about 20 Angstroms (Å) to about 1,000 Å, for example, about 30 Å to about 300 Å. While not wishing to be bound by theory, it is understood that when the thickness of the hole blocking layer is within these ranges, the hole blocking layer may have excellent hole blocking characteristics without a substantial increase in driving voltage.

In an embodiment, the electron transport layer 160 may include tris(8-quinolinato) aluminium (Alq$_3$), BAlq, a compound including a pyridine ring, such as 1,3,5-tri[(3-pyridyl)-phen-3-yl]benzene, a compound including a triazine ring, such as 2,4,6-tris(3'-(pyridin-3-yl)biphenyl-3-yl)-1,3,5-triazine, a compound including an imidazole ring, such as 2-(4-(N-phenylbenzimidazolyl-1-yl-phenyl)-9,10-di-naphthylanthracene, a compound including a triazole ring, such as TAZ and NTAZ, 1,3,5-tris(N-phenyl-benzimidazol-2-yl)benzene (TPBi), BCP, or Bphen:

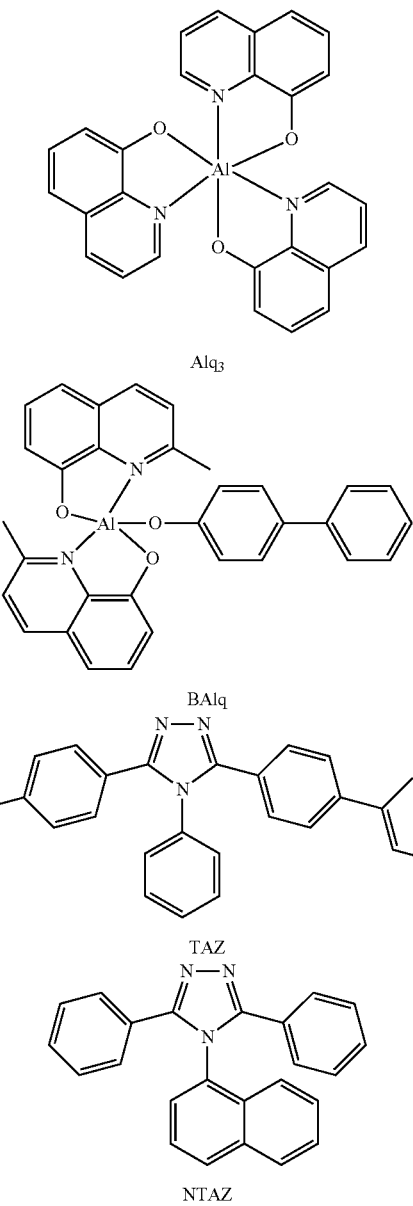

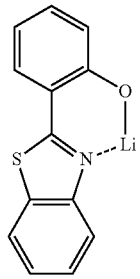

ET-D2

The electron transport layer 160 may be formed to a thickness, for example, in a range of about 15 nm to about 50 nm.

The electron injection layer 170 may be formed on the electron transport layer 160.

The electron injection layer 170 may include, for example, an lithium compound, such as (8-hydroxyquinolinato)lithium (LiQ) and lithium fluoride (LiF), sodium chloride (NaCl), cesium fluoride (CsF), lithium oxide ($Li_2O$), or barium oxide (BaO).

The electron injection layer 170 may be formed to a thickness in a range of about 0.3 nm to about 9 nm.

The second electrode 180 may be formed on the electron injection layer 170. The second electrode 180 may be a cathode and may be formed by using a material having a low work function among a metal, an alloy, an electrically conductive compound, and any combination thereof. For example, the second electrode 180 may be formed as a reflective electrode by using a metal such as lithium (Li), magnesium (Mg), aluminum (Al), and calcium (Ca), or an alloy such as aluminum-lithium (Al—Li), magnesium-indium (Mg—In), and magnesium-silver (Mg—Ag). Alternatively, the second electrode 180 may be formed as a transparent electrode by using the metal or the alloy thin film having a thickness of 20 nm or less, or a transparent conductive film such as indium tin oxide ($In_2O_3$—$SnO_2$) and indium zinc oxide ($In_2O_3$—ZnO).

In addition, the stacked structure of the organic light-emitting device 100 according to the embodiment is not limited to the above-described stacked structure. The organic light-emitting device 100 according to the embodiment may be formed in other known stacked structures. For example, in the organic light-emitting device 100, at least one of the hole injection layer 130, the hole transport layer 140, the electron transport layer 160, and the electron injection layer 170 may be omitted. The organic light-emitting device 100 may further include another layer. In addition, each layer of the organic light-emitting device 100 may be a single layer or a multi-layer.

A method of manufacturing each layer of the organic light-emitting device 100 according to the embodiment is not particularly limited. For example, each layer of the organic light-emitting device 100 according to the embodiment may be manufactured by using various methods, such as vacuum deposition, solution coating, and Langmuir-Blodgett (LB) deposition.

The solution coating may include spin coating, casting, micro gravure coating, gravure coating, bar coating, roll coating, wire bar coating, dip coating, spry coating, screen printing, flexographic printing, offset printing, and ink-jet printing.

Examples of the solvent used in the solution coating may include toluene, xylene, diethyl ether, chloroform, ethyl In one or more embodiments, the electron transport layer 160 may include a commercial product, such as KLET-01, KLET-02, KLET-03, KLET-10, or KLET-M1 (these products are available from Chemipro Kasei).

The electron transport layer 160 may further include, in addition to the materials described above, a metal-containing material.

The metal-containing material may include a Li complex. The Li complex may include, for example, Compound ET-D1 (lithium 8-hydroxyquinolate, LiQ) or ET-D2.

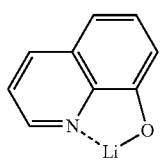

ET-D1 acetate, dichloromethane, tetrahydrofuran, acetone, acetonitrile, N,N-dimethylformamide, dimethylsulfoxide, anisole, hexamethylphosphoric acid triamide, 1,2-dichloroethane, 1,1,2-trichloroethane, chlorobenzene, o-dichlorobenzene, dioxane, cyclohexane, n-pentane, n-hexane, n-heptane, n-octane, n-nonane, n-decane, methyl ethyl ketone, cyclohexanone, butyl acetate, ethyl cellosolve acetate, ethylene glycol, ethylene glycol monobutyl ether, ethylene glycol monoethyl ether, ethylene glycol monomethyl ether, dimethoxy ethane, propylene glycol, diethoxymethane, triethylene glycol monoethyl ether, glycerine, 1,2-hexanediol, methanol, ethanol, propanol, iso-propanol, cyclohexanol, and N-methyl-2-pyrrolidone, but the solvent is not limited as long as the solvent can dissolve the material used to form each layer.

Considering the coatability, the concentration of the composition used in the solution coating may be in a range from 0.1 weight % to 10 weight %, and for example, in a range from 0.5 weight % to 5 weight %, but embodiments of the present disclosure are not limited thereto.

The compound used in the vacuum deposition may be different according to the structure and thermal characteristics of the target layer, but may be selected from, for example, a deposition temperature of about 100° C. to about 500° C., a vacuum degree of about $10^{-8}$ torr to about $10^{-3}$ torr, a deposition rate of about 0.01 Angstroms per second (Å/sec) to about 100 Å/sec.

In an embodiment, the first electrode 120 may be an anode, and the second electrode 180 may be a cathode.

For example, the first electrode 120 may be an anode; the second electrode 180 may be a cathode; the organic layer may include the emission layer 150 between the first electrode 120 and the second electrode 180; the organic layer may further include a hole transport region disposed between the first electrode 120 and the emission layer 150 and an electron transport region disposed between the emission layer 150 and the second electrode 180; the hole transport region may include at least one selected from a hole injection layer 130, a hole transport layer 140, a buffer layer, and an electron blocking layer; and the electron transport region may include at least one selected from a hole blocking layer, an electron transport layer 160, and an electron injection layer 170.

In one or more embodiments, the first electrode 120 may be a cathode, and the second electrode 180 may be an anode.

Hereinbefore, the organic light-emitting device has been described with reference to the FIGURE, but embodiments of the present disclosure are not limited thereto.

Description of Substituents

The expression "X and Y may each independently be" as used herein refers to a case where X and Y may be identical to each other, or a case where X and Y may be different from each other.

The term "substituted" as used herein refers to a case where hydrogen of a substituent such as $R_{11}$ may be further substituted with other substituents.

The term "derived" as used herein refers to a case where a compound is modified without changing the basic structure and properties of the compound. For example, a group derived from an aromatic compound maintains the skeletal structure of the aromatic compound. In addition, a group derived from a given compound may be understood as an n-th group in which hydrogen in the number of n is excluded from the given compound.

The term "$C_1$-$C_{10}$ alkyl group" as used herein refers to a linear or branched aliphatic hydrocarbon monovalent group having 1 to 10 carbon atoms, and non-limiting examples thereof include a methyl group, an ethyl group, an n-propyl group, an iso-propyl group, an n-butyl group, an iso-butyl group, a sec-butyl group, a tert-butyl group, an n-pentyl group, an iso-pentyl group, a tert-pentyl group, a neo-pentyl group, a 1,2-dimethylpropyl group, an n-hexyl group, an iso-hexyl group, a 1,3-dimethylbutyl group, 1-iso-propylpropyl group, a 1,2-dimethylbutyl group, an n-heptyl group, a 1,4-dimethylpentyl group, a 3-ethylpentyl group, a 2-methyl-1-iso-propylpropyl group, a 1-ethyl-3-methylbutyl group, an n-octyl group, a 2-ethylhexyl group, 3-methyl-1-iso-propylbutyl group, a 2-methyl-1-iso-propyl group, a 1-tert-butyl-2-methylpropyl group, an n-nonyl group, an n-decyl group, and an iso-decyl group.

The term "$C_3$-$C_{10}$ cycloalkyl group" as used herein refers to a monovalent saturated hydrocarbon monocyclic group having 3 to 10 carbon atoms involved in the ring formation, and examples thereof include a cyclopropyl group, a cyclobutyl group, a cyclopentyl group, a cyclohexyl group, and a cycloheptyl group.

The term "aryl group having 5 to 60 ring-forming carbon atoms" as used herein refers to a monovalent group having an carbocyclic aromatic system including 5 to 60 carbon atoms involved in ring formation (that is, when substituted with a substituent, an atom included in the substituent is not counted as a ring-forming carbon). Non-limiting examples of the aryl group having 6 to 60 ring-forming carbon atoms include a phenyl group, a naphthyl group, an anthracenyl group, a phenanthrenyl group, a pyrenyl group, and a chrysenyl group.

The term "heteroaryl group having 5 to 60 ring-forming atoms" as used herein refers to a monovalent heterocyclic aromatic system having at least one heteroatom selected from N, O, Si, P, and S as a ring-forming atom and 5 to 60 carbon atoms. Non-limiting examples of the heteroaryl group having 5 to 60 ring-forming atoms include a pyridinyl group, a pyrimidinyl group, a pyrazinyl group, a pyridazinyl group, a triazinyl group, a quinolinyl group, and an isoquinolinyl group.

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 2 to 60 carbon atoms) having two or more rings condensed to each other, a heteroatom selected from N, O, P, Si, and S, other than carbon atoms, as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "carbocyclic group having 5 to 60 ring-forming carbon atoms" as used herein refers to a saturated or unsaturated cyclic group having, as a ring-forming atom, 5 to 60 carbon atoms only. The term "carbocyclic group having 5 to 60 ring-forming carbon atoms" as used herein refers to a monocyclic group or a polycyclic group, and, according to its chemical structure, a monovalent, divalent, trivalent, tetravalent, pentavalent, or hexavalent group.

The term "heterocyclic group having 5 to 60 ring-forming atoms" as used herein refers to a saturated or unsaturated cyclic group having, as a ring-forming atom, at least one heteroatom selected from N, O, P, Si, and S, in addition to a carbon atom, wherein the number of atoms involved in ring formation is 5 to 60. The term "$C_5$-$C_{60}$ heterocyclic group" as used herein refers to a monocyclic group or a polycyclic group, and, according to its chemical structure, a monovalent, divalent, trivalent, tetravalent, pentavalent, or hexavalent group.

At least one substituent of the substituted $C_1$-$C_{10}$ alkyl group, the substituted $C_3$-$C_{10}$ cycloalkyl group, the substituted aryl group having 6 to 60 ring-forming carbon atoms, the substituted heteroaryl group having 5 to 60 ring-forming atoms, the substituted monovalent non-aromatic condensed polycyclic group, the substituted monovalent non-aromatic condensed heteropolycyclic group, the substituted carbocyclic group having 5 to 60 ring-forming carbon atoms, and the substituted heterocyclic group having 5 to 60 ring-forming atoms may be selected from:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —P(=O)($Q_{18}$)($Q_{19}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —C$_1$, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —P(=O)($Q_{28}$)($Q_{29}$); and —N($Q_{31}$)($Q_{32}$), —Si($Q_{33}$)($Q_{34}$)($Q_{35}$), —B($Q_{36}$)($Q_{37}$), and —P(=O)($Q_{38}$)($Q_{39}$), and $Q_1$ to $Q_9$, $Q_{11}$ to $Q_{19}$, $Q_{21}$ to $Q_{29}$, and $Q_{31}$ to $Q_{39}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one selected from a $C_1$-$C_{60}$ alkyl group, and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

Others

The expression "A to B" as used herein refers to a range from A to B, including A and B.

While the embodiments of the present disclose have been described with reference to the accompanying drawings, it is understood that the present disclosure is not limited to these embodiments. It is apparent to those of ordinary skill in the art that various modifications or changes may be made thereto without departing from the spirit and scope of the appended claims. It is understood that various modifications or changes fall within the technical scope of the present disclosure.

Hereinafter, a condensed cyclic compound represented by Formula 1 and an organic light-emitting device including the same will be described in detail with reference to Examples and Comparative Examples. Examples provided below are merely an example, and the condensed cyclic compound and the organic light-emitting device, according to embodiments, are not limited to Examples provided below.

The expression "B was used instead of A" used in describing Synthesis Examples means that a molar equivalent of "A" was identical to a molar equivalent of "B".

In addition, "%" is weight % unless specified otherwise.

EXAMPLES
Synthesis Example 1: Synthesis of Compound 1-1
Compound 1-1 was synthesized according to the Reaction Scheme:
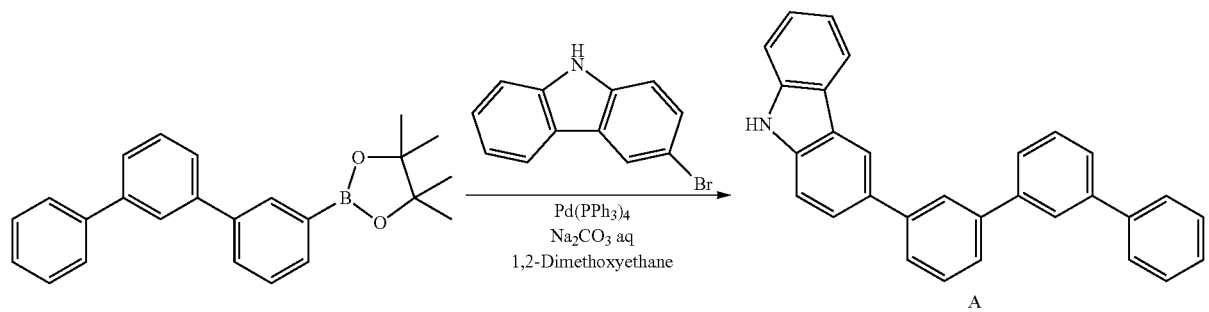
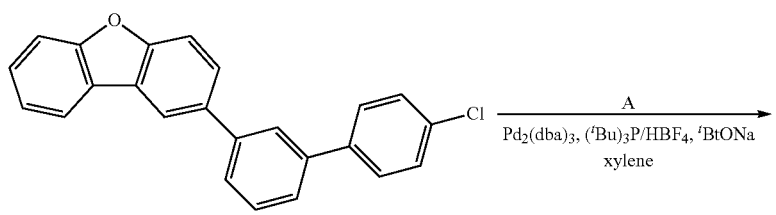
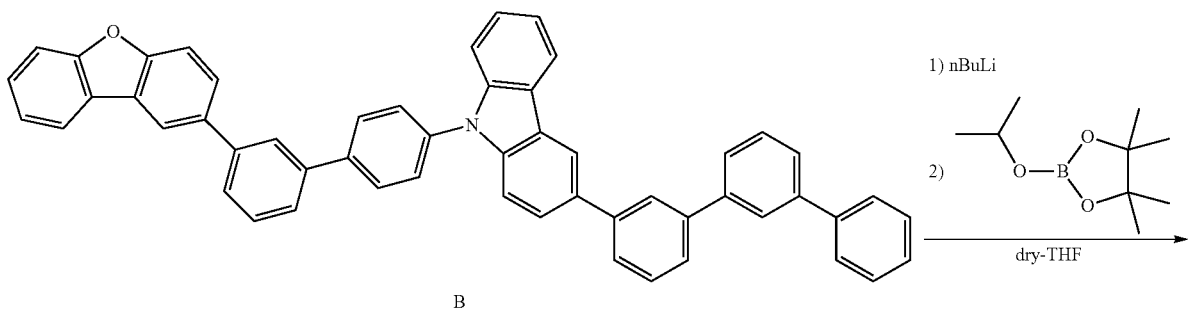
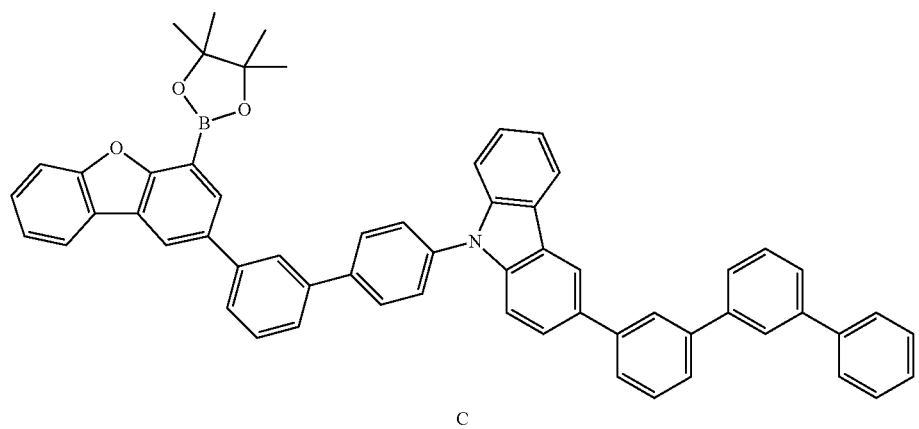

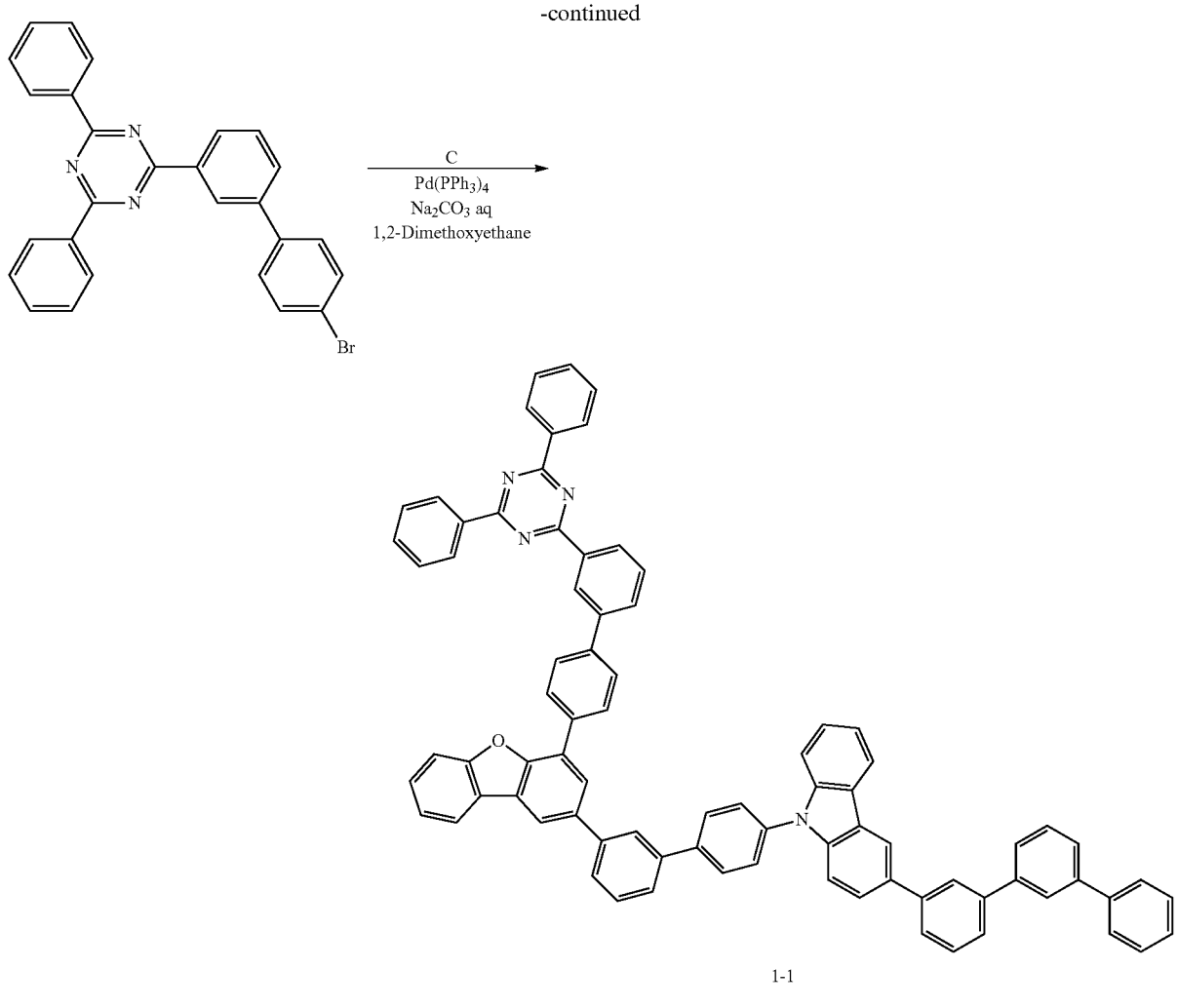

1-1

1) Synthesis of Intermediate A

In an argon atmosphere, 3-bromo-9H-carbazole (12.3 grams (g), 50 mmol, millimoles), 2-([1,1':3'1'-terphenyl]-3-yl)-4,4,5,5-tetramethyl-1,3,2-dioxaborolane (18.0 g, 50.5 mmol), tetrakis(triphenylphosphine)palladium (1.73 g, 1.50 mmol), 100 milliliters (ml) of 1,2-dimethoxyethane, and 75 ml of 2 molar (M) aqueous sodium carbonate solution were added to a 200-ml three-neck flask, and the mixture was stirred at a temperature of 80° C. for 8 hours. After the mixture was left at room temperature, impurities were filtered and separated by using celite. The organic layer was concentrated and purified by column chromatography to obtain Intermediate A (14.6 g, 36.9 mmol, yield of 73.8%).

2) Synthesis of Intermediate B

In an argon atmosphere, 2-(4'-chloro-[1,1'-biphenyl]-3-yl) dibenzo[b,d]furan) (3.35 g, 10.0 mmol), Intermediate A (4.15 g, 10.5 mmol), tris(dibenzylideneacetone)dipalladium) (0.916 g, 1.00 mmol), tetrafluoroboric acid tri-t-butylphosphine (1.16 g, 4.00 mmol), sodium-t-butoxide (1.44 g, 15.0 mmol), and 30 ml of anhydrous xylene were added to a 300-ml three-neck flask, and the mixture was stirred at a temperature of 120° C. for 4 hours. After the mixture was left at room temperature, impurities were filtered and separated by using celite. The organic layer was concentrated and purified by column chromatography to obtain Intermediate B (5.02 g, 7.03 mmol, yield of 70.3%).

3) Synthesis of Intermediate C

In an argon atmosphere, Intermediate B (5.00 g, 7.00 mmol) and 100 ml of anhydrous tetrahydrofuran (THF) were added to a 300-ml three-neck flask, and the mixture was cooled to a temperature of −78° C. Then, n-butyllithium, 1.6 M hexane solution (n-butyllithium, 1.6 M in hexane) (6.6 ml, 10.5 mmol) were added dropwise thereto for 30 minutes. For 4 hours after the dropwise addition, the mixture was maintained at a temperature of −78° C. and stirred. Then, 2.2 ml of 2-iso-propoxy-4,4,5,5-tetramethyl-1,3,2-dioxaborolane was added dropwise thereto, a reaction was allowed to proceed for 15 minutes, and the mixture was stirred again at room temperature for 5 hours. Then, 100 ml of ion-exchange water was added thereto, the product was extracted by using dichloromethane and recrystallized by using methanol to obtain Intermediate C (4.6 g, 5.48 mmol, yield of 78.2%).

4) Synthesis of Compound 1-1

In an argon atmosphere, 2-(4'-bromo-[1,1'-biphenyl]-3-yl)-4,6-diphenyl-1,3,5-triazine (0.99 g, 2 mmol), Intermediate C (1.72 g, 2.05 mmol), tetrakis(triphenylphosphine) palladium (0.07 g, 0.06 mmol), 10 ml of 1,2-dimethoxyethane, 10 ml of toluene, and 3 ml of 2 M aqueous sodium carbonate solution were added to a 100-ml three-neck flask, and the mixture was stirred at a temperature of 100° C. for 8 hours. After the mixture was cooled to room temperature, impurities were filtered and separated by using celite. The organic layer was concentrated and purified by column chromatography to obtain Compound 1-1 (1.10 g, 1.0 mmol, yield of 50.0%).

A molecular weight (m/z value) of Compound 1-1 measured by LC-MS was 1097 ($M^+$), which was identical to a calculated value. The number of aromatic rings in Compound 1-1 was 14.

Synthesis Example 2: Synthesis of Compound 1-2

Compound 1-2 was synthesized according to the Reaction Scheme:

A molecular weight (m/z value) of Compound 1-2 measured by LC-MS was identical to 1173 ($M^+$), which was a calculated value. The number of aromatic rings in Compound 1-2 was 15.

Evaluation Example 1: Measurement of Solubility 50 milligrams (mg) of Compound 1-1 and 450 mg of methyl benzoate (solvent) were added to a colorless sample bottle, the mixture was irradiated with ultrasonic waves at room temperature for 5 minutes, and the presence or absence of Compound 1-1 was visually confirmed. If Compound 1-1 did not remain, the solubility of Compound 1-1 was 10 percent by weight (weight %) or more. If Compound 1-1 remained, a small amount of the solvent was added, the irradiation with ultrasonic waves was repeated, and an amount of the solvent was measured until Compound 1-1 was completely dissolved. The solubility was calculated from an amount of the solvent finally used. The solubility

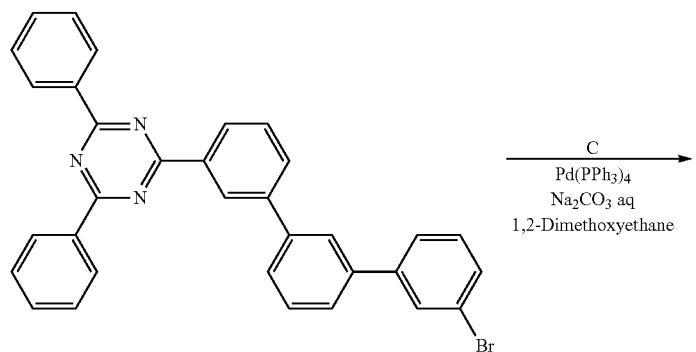

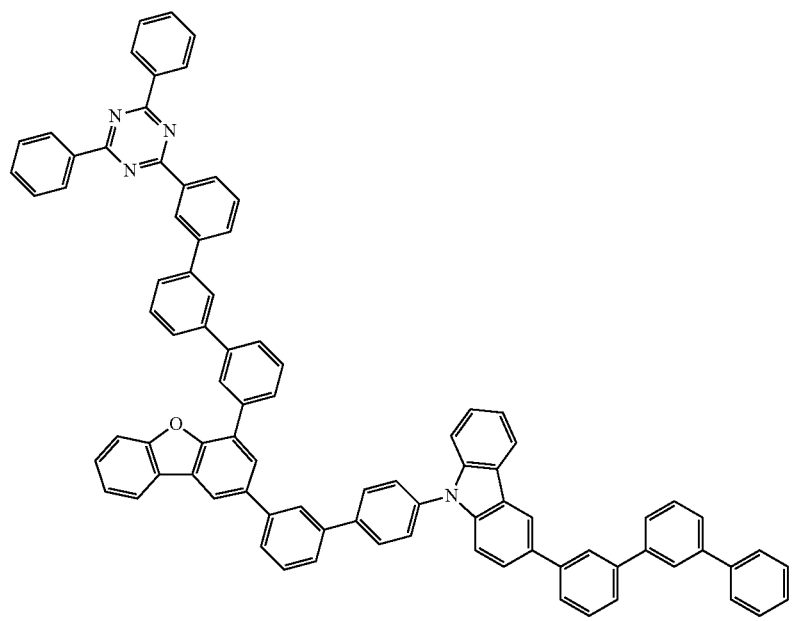

1-2 values of Compound 1-2 and host-c were calculated in the same manner. The results are shown in Table 1.

TABLE 1

| | Solubility (weight %) |
|---|---|
| Compound 1-1 | 4 |
| Compound 1-2 | 4 |
| host-c | 0.1 |

Referring to Table 1, it is confirmed that Compounds 1-1 and 1-2 have high solubility in an organic solvent, as compared with host-c. Therefore, it is confirmed that Compound 1-1 and 1-2 are suitable for manufacturing an organic light-emitting device at a low cost, as compared with host-c.

Example 1

Poly(3,4-ethylene dioxythiophene)/poly(4-styrene sulfonate) (PEDOT/PSS) (manufactured by Sigma-Aldrich) were spin-coated on a glass substrate having a 150-nm stripe-shaped ITO such that a thickness of a dried film was 15 nanometers (nm), thereby forming a hole injection layer.

Then, a solution in which P-1 and FA-14 were dissolved in anisole was spin-coated on the hole injection layer such that a thickness of a dried film was 125 nm, thereby forming a hole transport layer. At this time, P-1 was 80 weight % based on a total weight of the hole transport layer, FA-14 was 20 weight % based on a total weight of the hole transport layer.

Then, a methyl benzoate solution including Compound 1-1 (host), HT-Host-A (host), and tris(2-(3-p-xylyl)phenyl) pyridine iridium (TEG) (dopant) was spin-coated on the hole transport layer such that a thickness of a dried film was 55 nm, thereby forming an emission layer. At this time, TEG was 10 weight % based on a total weight of the emission layer, and Compound 1-1 and HT-Host-A were at a weight ratio of 5:5.

Then, the substrate on which the emission layer was formed was introduced into a vacuum evaporator, and LiQ and KLET-03 were co-deposited at a volume ratio of 1:1, thereby forming an electron transport layer having a thickness of 20 nm.

LiQ was deposited on the electron transport layer to form an electron injection layer having a thickness of 3.5 nm.

Then, aluminum was deposited on the electron injection layer to form a cathode having a thickness of 100 nm, thereby completing the manufacture of an organic light-emitting device.

P-1 was manufactured according to a method of preparing Compound T, disclosed in International Publication No. WO 2011/159872. The constitutional formula of P-1 is as follows:

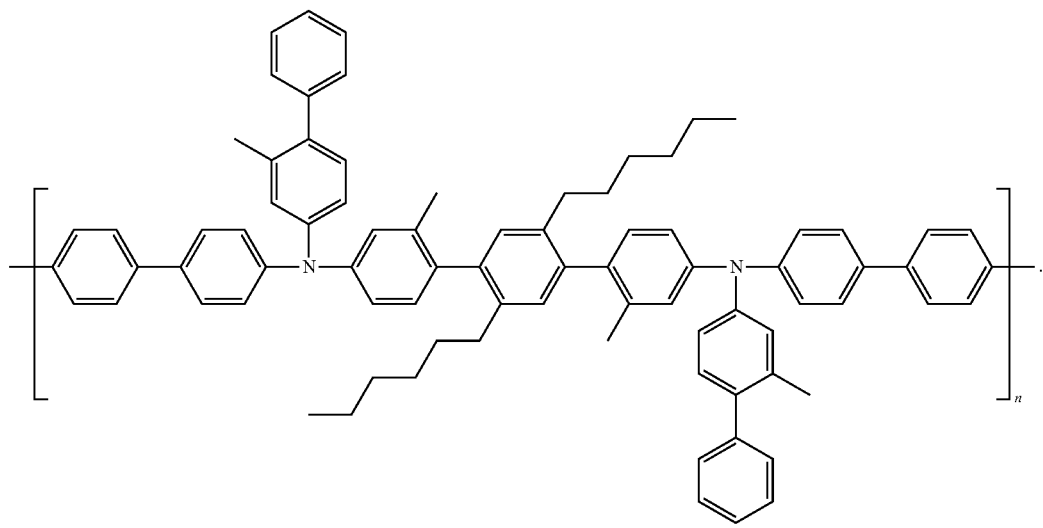

P-1

Number average molecular weight $M_n$=141,000
Weight average molecular weight $M_w$=511,000
In addition, FA-14 is a compound disclosed in US Patent Application Publication No. 2016/0315259, which is incorporated herein in its entirety by reference, and the constitutional formula of FA-14 is as follows:

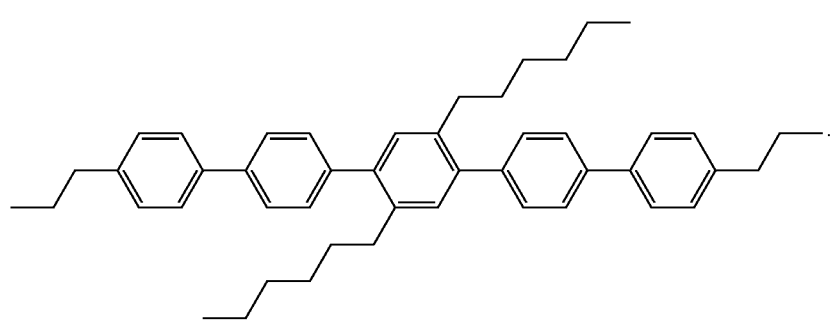

FA-14

HT-Host-A and HT-Host-B used in Examples 1 to 6 are hole transport host materials.

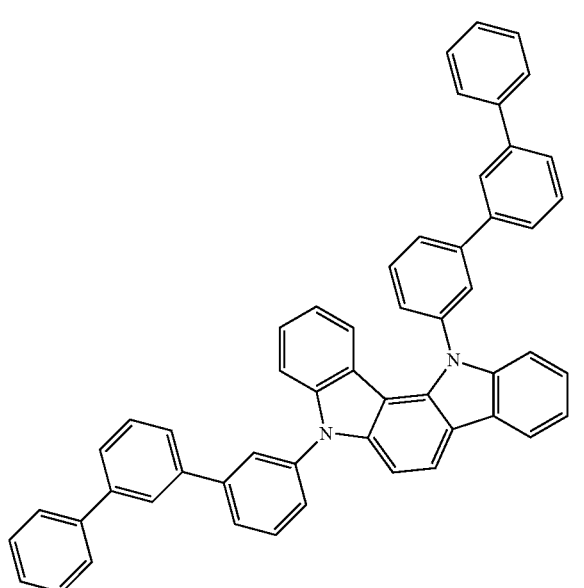

HT-Host-A

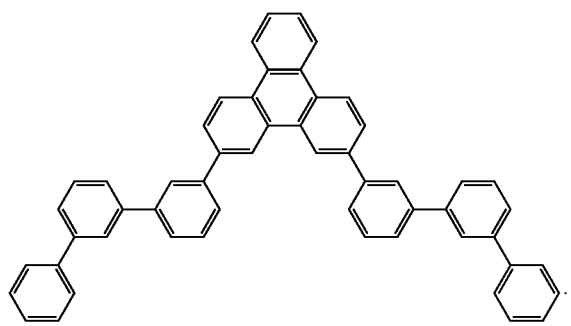

HT-Host-B

In addition, the constitutional formula of TEG is as follows:

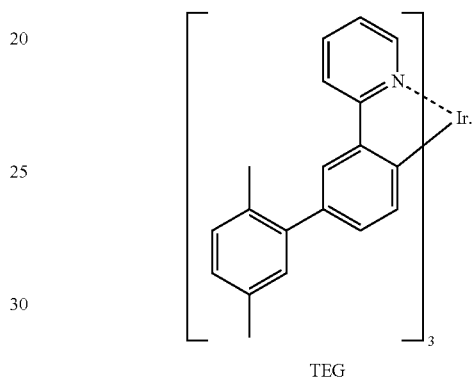

TEG

Examples 2 to 6 and Comparative Examples 1 and 2

Organic light-emitting devices were manufactured in the same manner as in Example 1, except that an emission layer was changed to the compositions shown in Table 2.

Evaluation Example 2

The current efficiency and light-emitting lifespan of the organic light-emitting devices of Examples 1 to 6 and Comparative Examples 1 and 2 were evaluated by using the following method. The organic light-emitting device was caused to emit light by applying a predetermined voltage thereto by using a DC constant voltage power supply (for example, Source Meter manufactured by KEYENCE). The light emission of the organic light-emitting device was measured by using a luminance measurement device (for example, SR-3 manufactured by Topcom), a current was set to be constant when a luminance was 6,000 candelas per square meter ($cd/m^2$) while gradually increasing a current applied thereto, and the organic light-emitting device was left.

Here, the current density (current value per unit area) of the organic light-emitting device was calculated, and the "current efficiency (cd/A)" was calculated by dividing the luminance ($cd/m^2$) by the current density (amperes per square meter, $A/m^2$).

In addition, the "light-emitting lifespan ($LT_{80}$, hr)" indicates an amount of time until the luminance value measured by using the luminance measurement device gradually decreased and becomes 80% of initial luminance.

These evaluation results are shown in Table 2.

The current efficiency and light-emitting lifespan of Examples 1 to 6 and Comparative Examples 1 and 2 are relative values when the measured values of Comparative Example 1 are 100.

TABLE 2

|  | Host (weight ratio) | Current efficiency | Light-emitting lifespan |
| --- | --- | --- | --- |
| Example 1 | Compound 1-1:HT-Host-A (5:5) | 128 | 360 |
| Example 2 | Compound 1-1:HT-Host-A (7:3) | 147 | 390 |
| Example 3 | Compound 1-2:HT-Host-A (5:5) | 122 | 300 |
| Example 4 | Compound 1-2:HT-Host-A (7:3) | 139 | 325 |
| Example 5 | Compound 1-1:HT-Host-B (5:5) | 143 | 360 |
| Example 6 | Compound 1-1:HT-Host-B (2:8) | 136 | 500 |
| Comparative Example 1 | host-a:host-b (5:5) | 100 | 100 |
| Comparative Example 2 | host-c | Since device could not be manufactured, measurement was impossible. | |

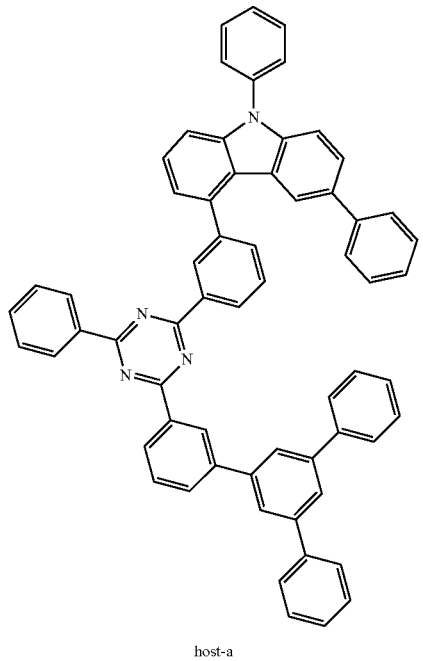 [SMILES: c1ccc(-c2cc(-c3ccccc3)cc(-c3cccc(-c4nc(-c5ccccc5)nc(-c5cccc(-c6cccc7c6c6cc(-c8ccccc8)ccc6n7-c6ccccc6)c5)n4)c3)c2)cc1]

host-a

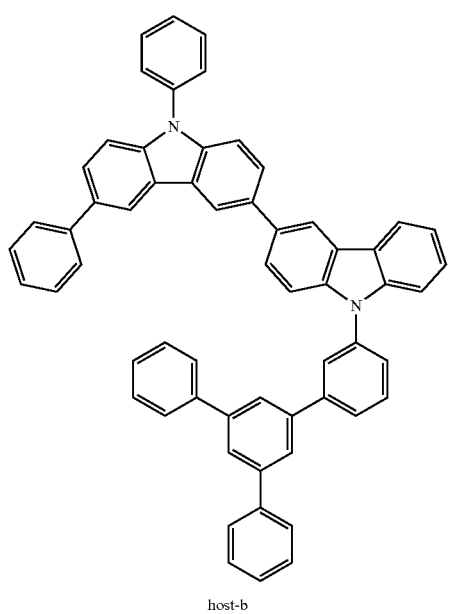 [SMILES: c1ccc(-c2cc(-c3ccccc3)cc(-c3cccc(-n4c5ccccc5c5cc(-c6ccc7c(c6)c6cc(-c8ccccc8)ccc6n7-c6ccccc6)ccc54)c3)c2)cc1]

host-b

TABLE 2-continued

| | Host (weight ratio) | Current efficiency | Light-emitting lifespan |
|---|---|---|---| host-c

Referring to Table 2, it is confirmed that the condensed cyclic compound has excellent characteristics in terms of the solubility to the solvent and is suitable for the solution process.

In addition, it is confirmed that the OLEDs described in Examples 1 to 6 have improved current efficiency and lifespan, as compared with that described in Comparative Example 1.

Since the condensed cyclic compound has improved electrical characteristics and/or thermal stability, the organic light-emitting device including the condensed cyclic compound has improved current efficiency and lifespan characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope of the present disclosure as defined by the following claims.

What is claimed is:

1. A condensed cyclic compound represented by Compounds 1-1 to 1-24 and 2-1 to 2-14:

1-1

1-2

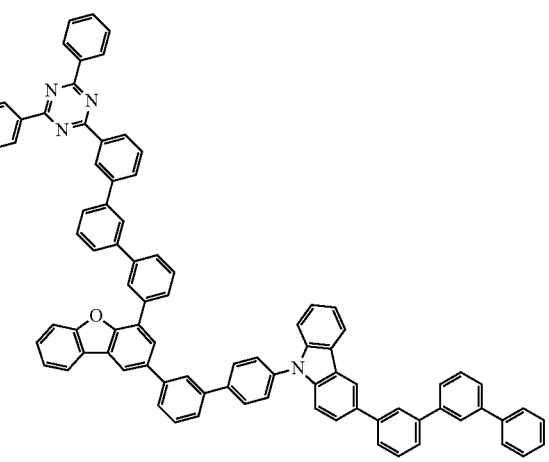

1-3

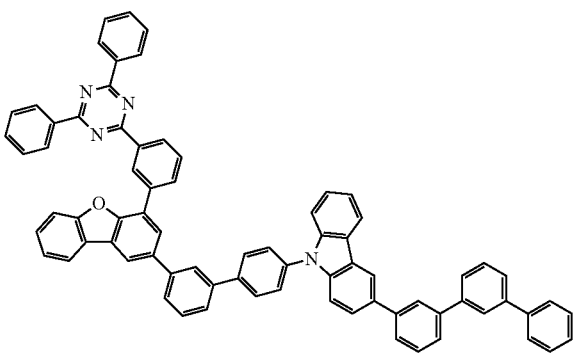

1-4
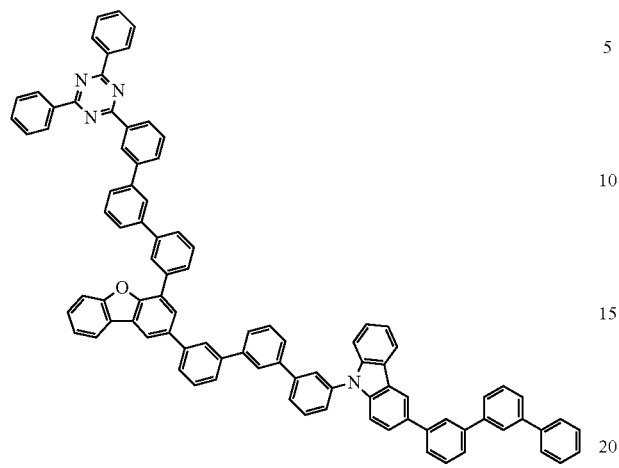
1-5
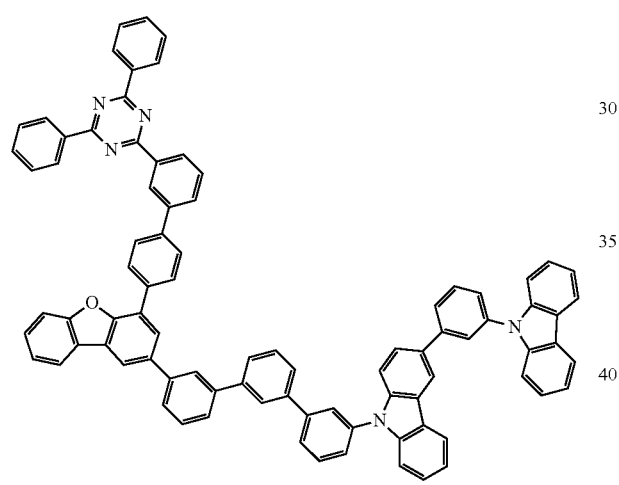
1-7
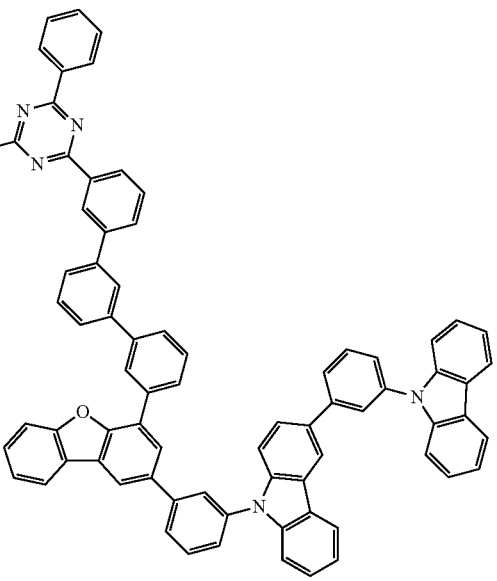
1-8
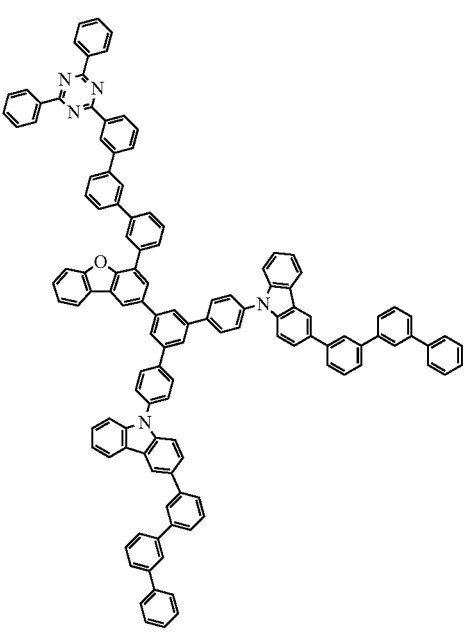
1-6

1-9
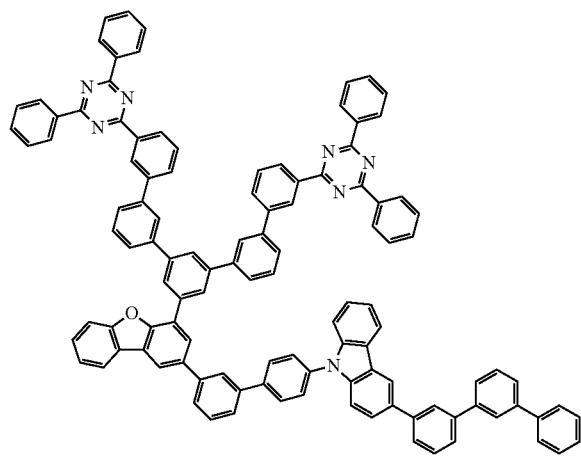
1-10
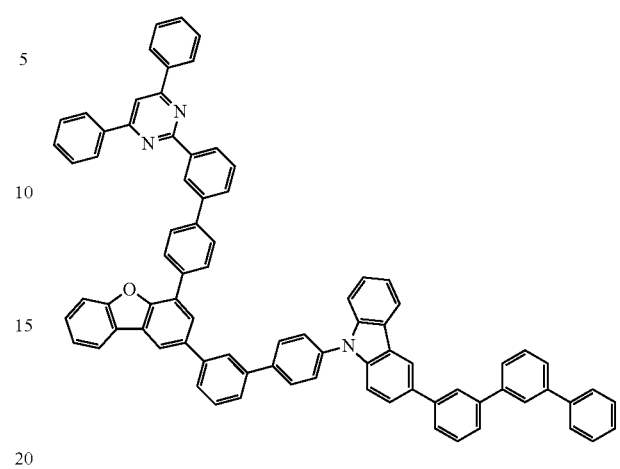
1-11
1-12
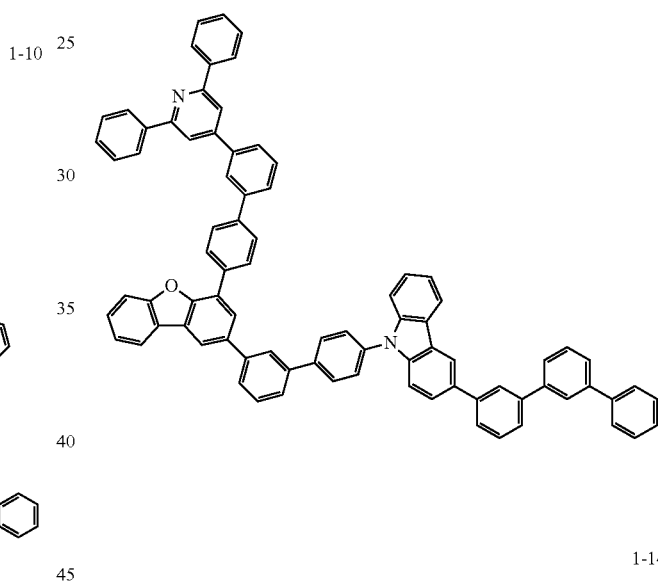
1-13
1-14
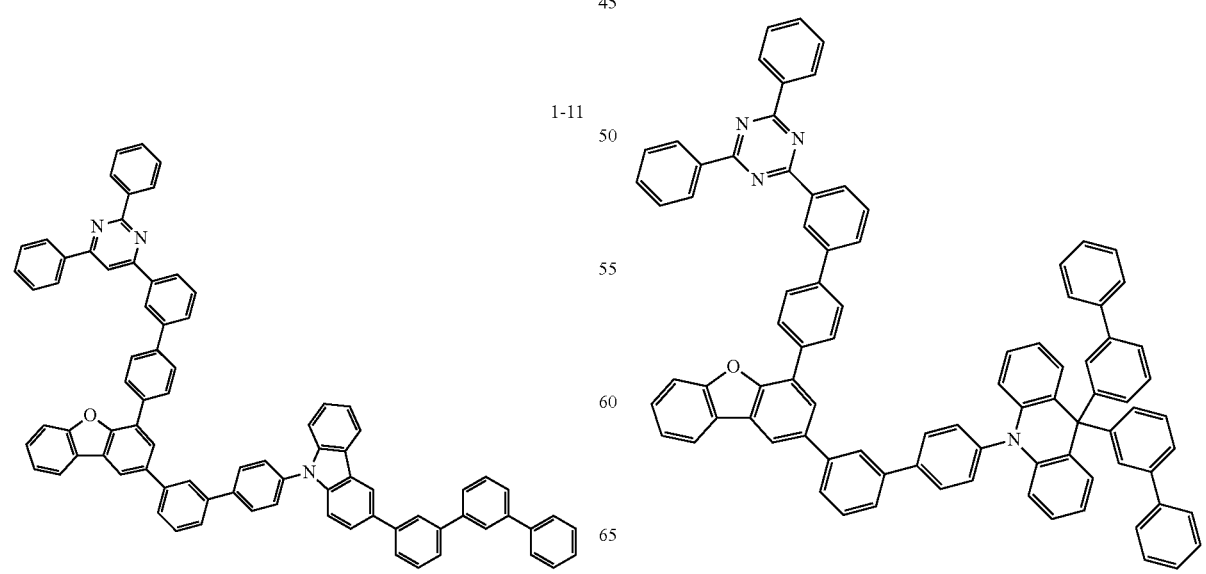

1-15
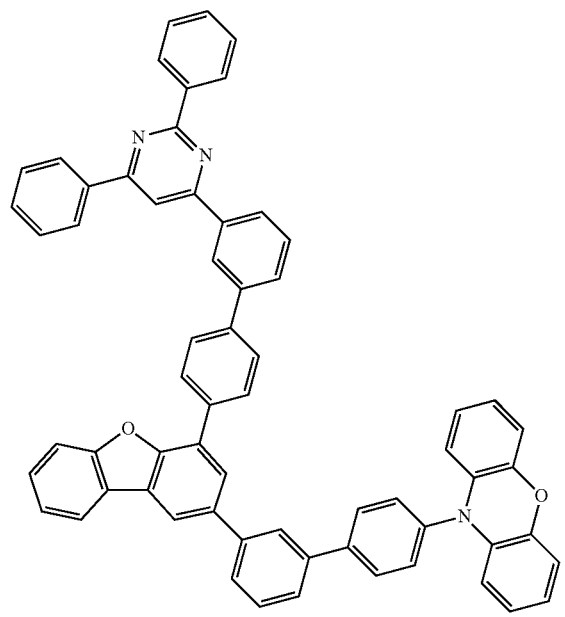
1-17
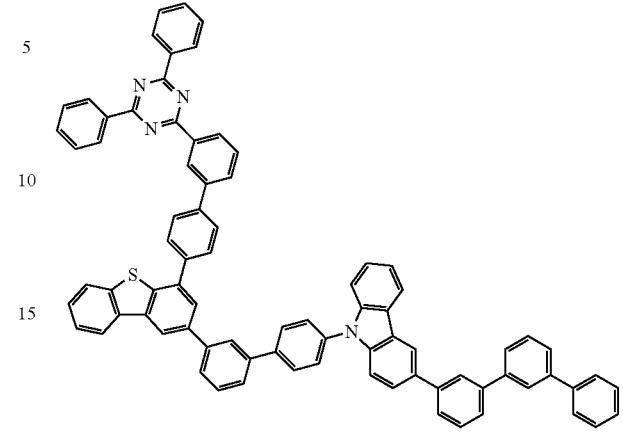
1-18
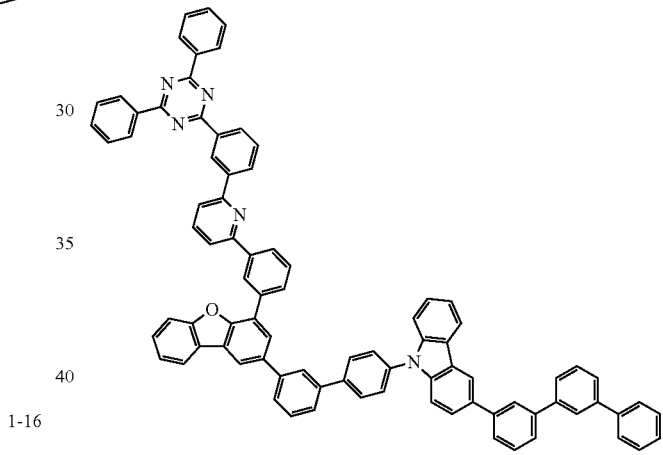
1-16
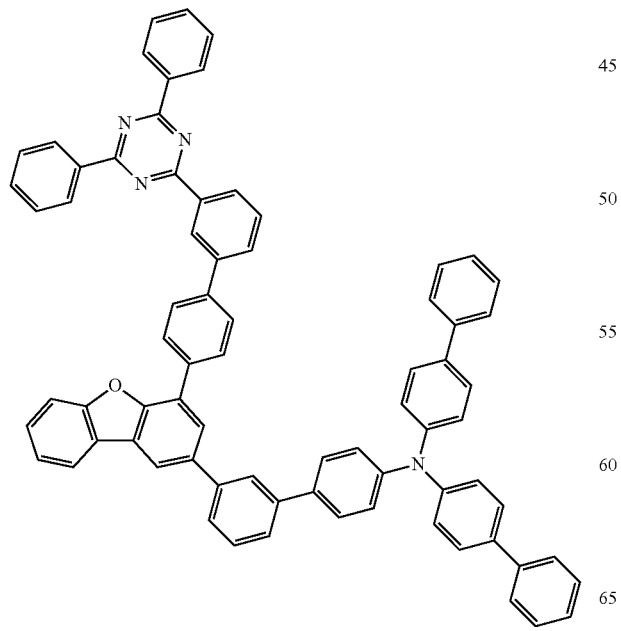
1-19

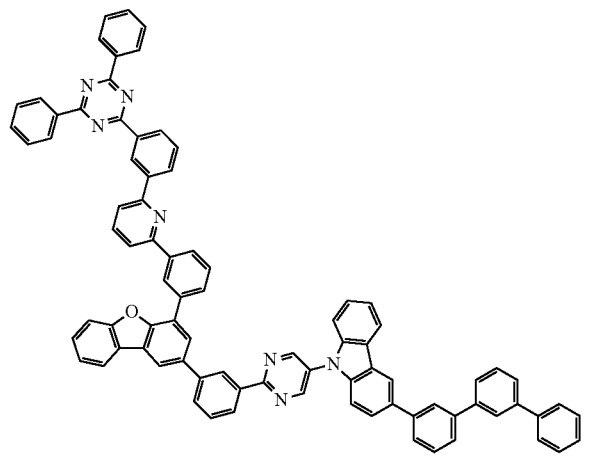
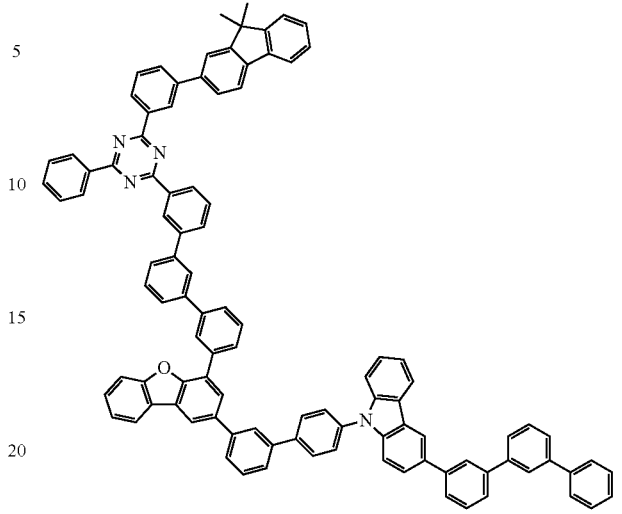
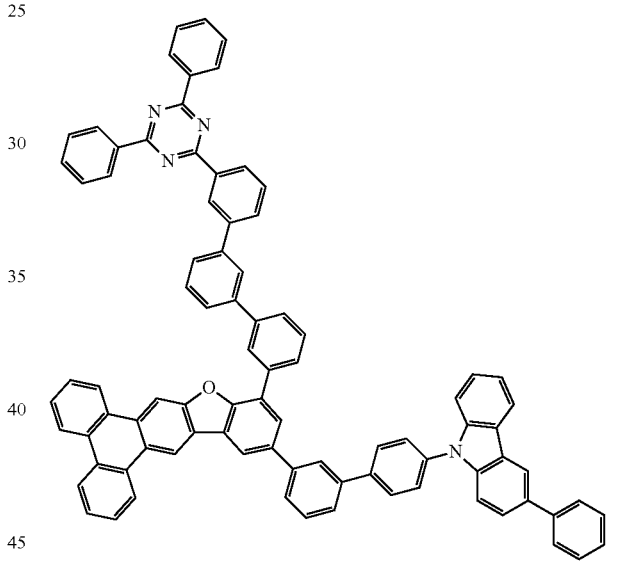
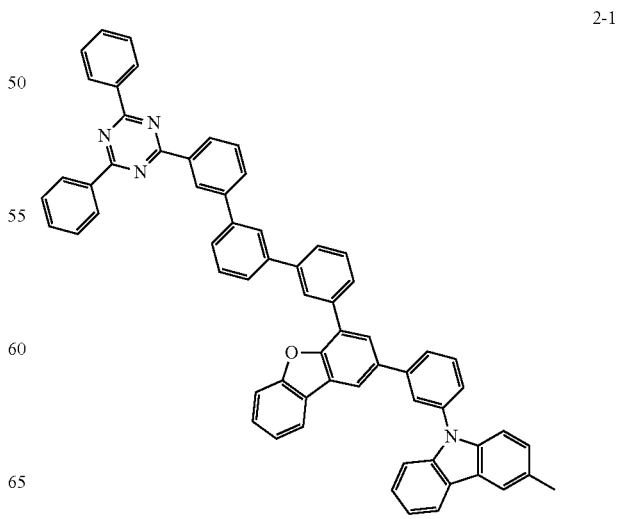

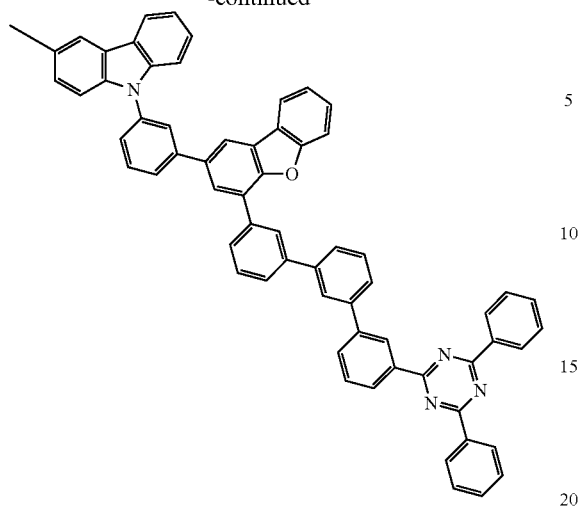
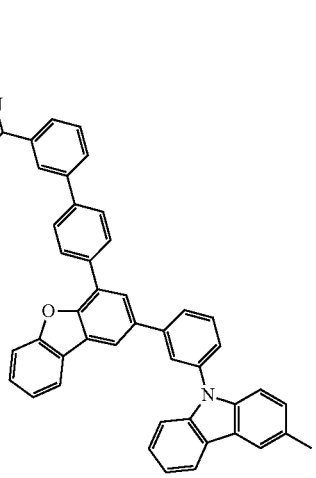
2-3
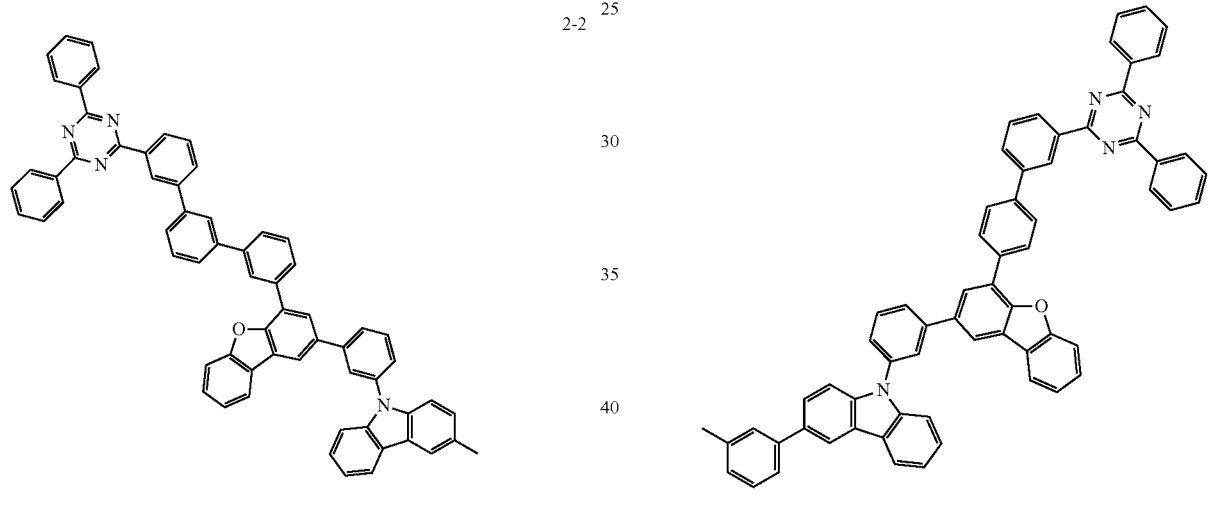
2-2
2-4
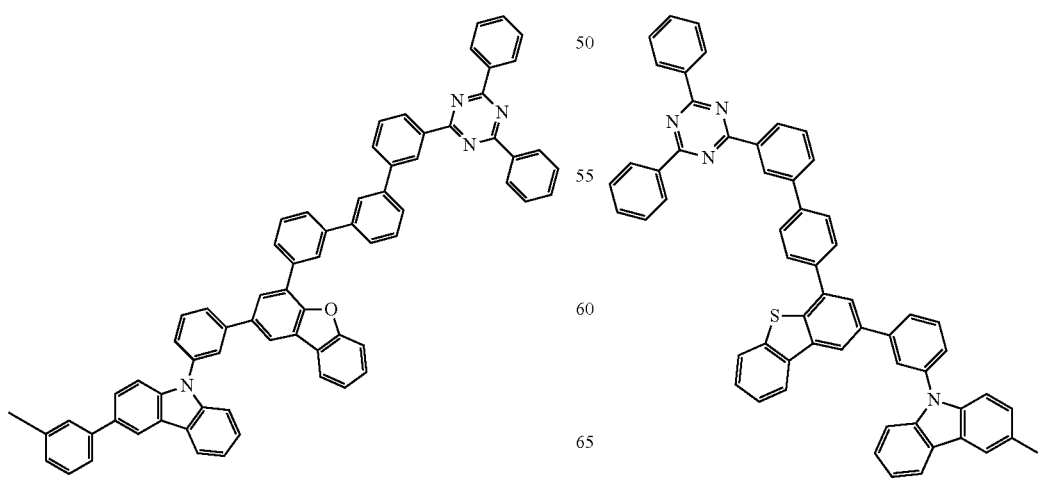

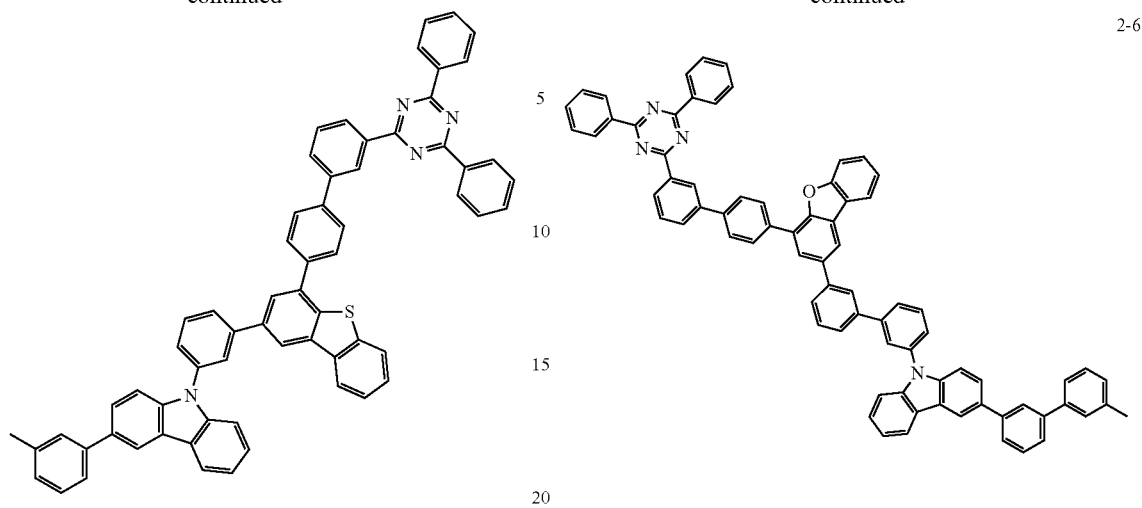
2-5
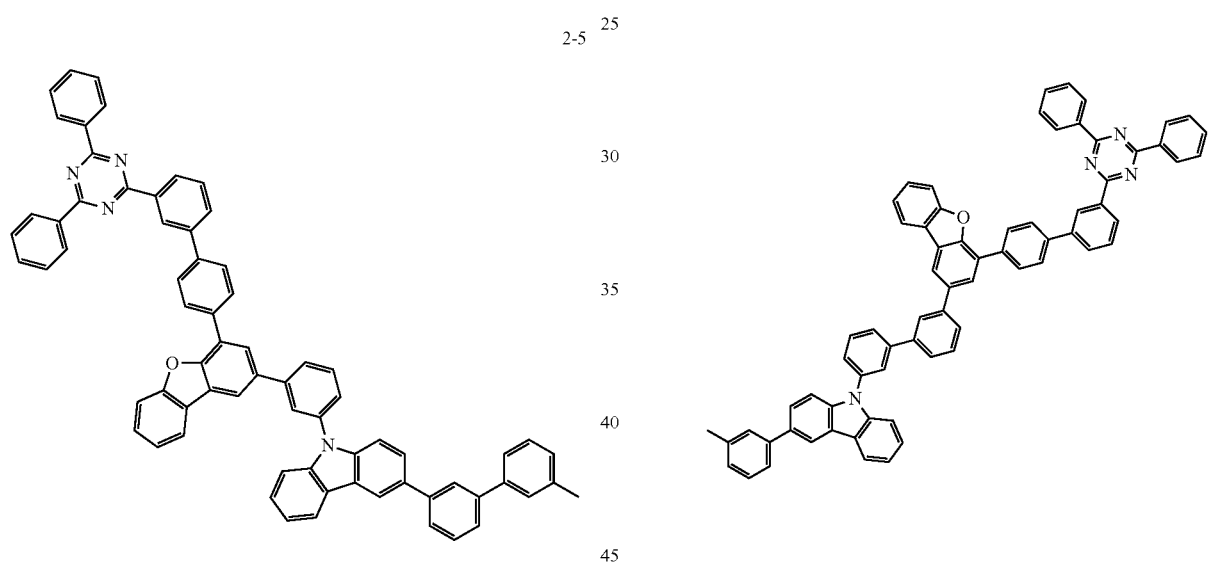
2-6
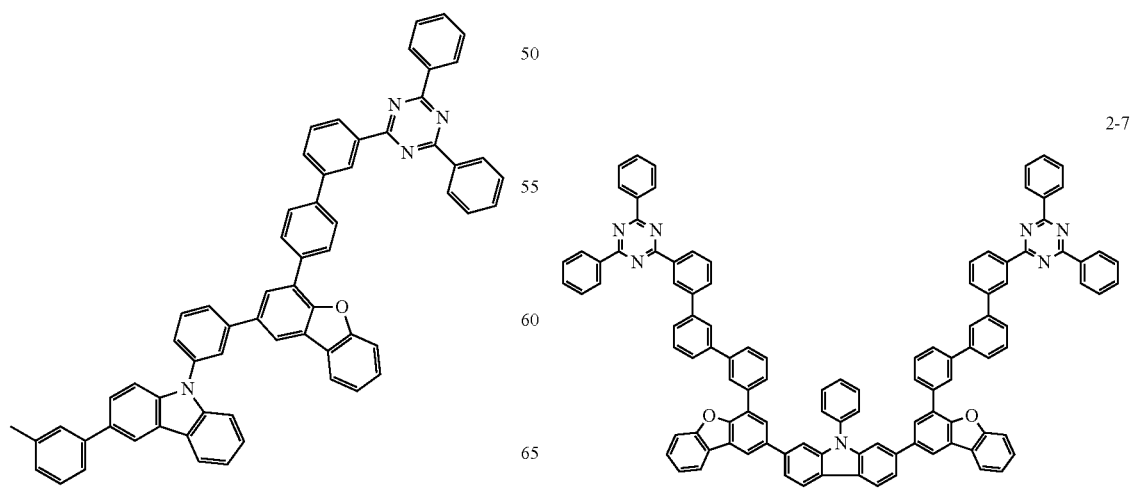
2-7

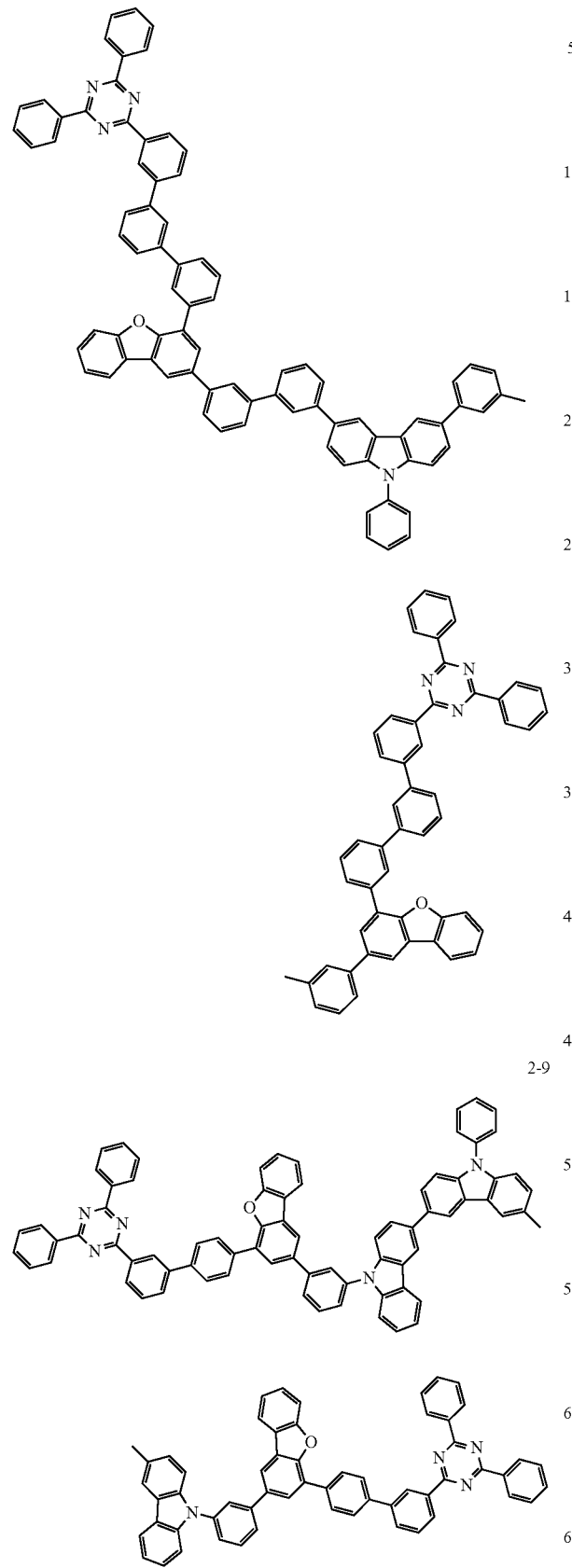
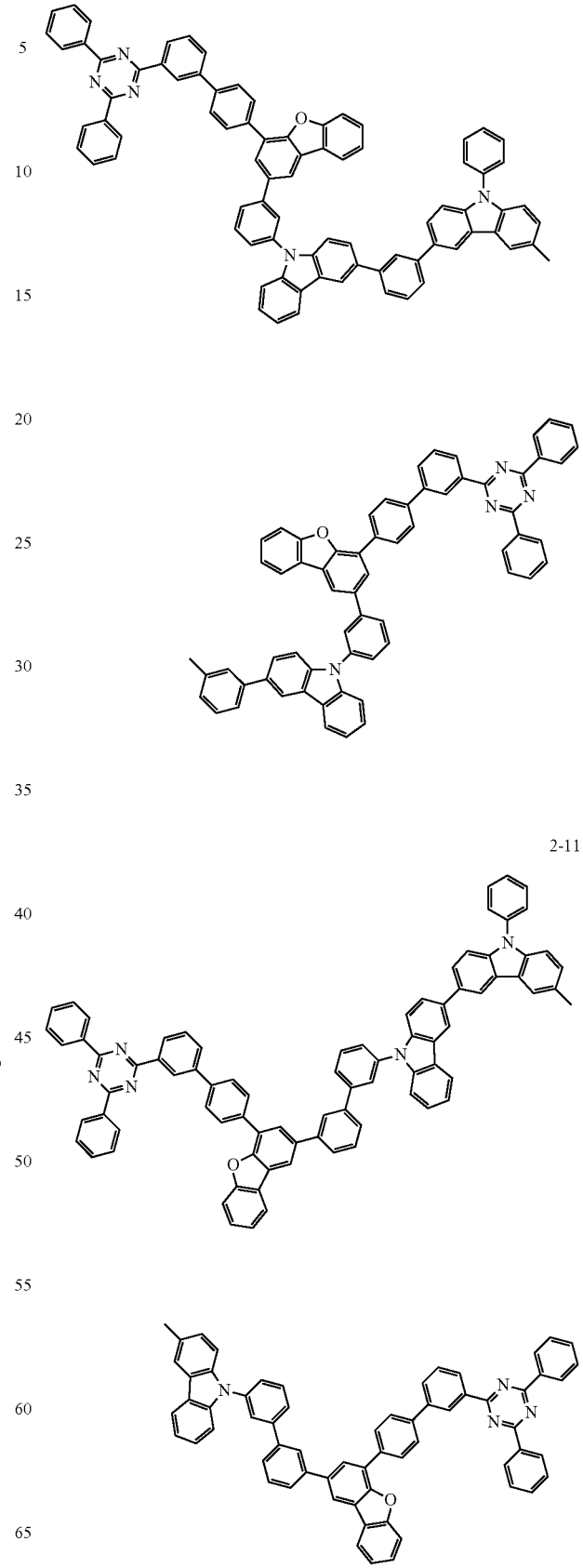

2-12
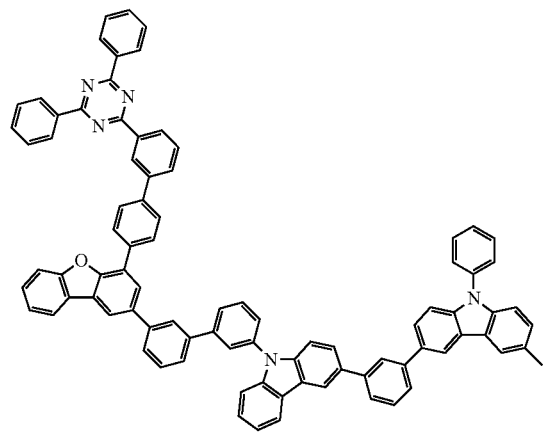
2-14
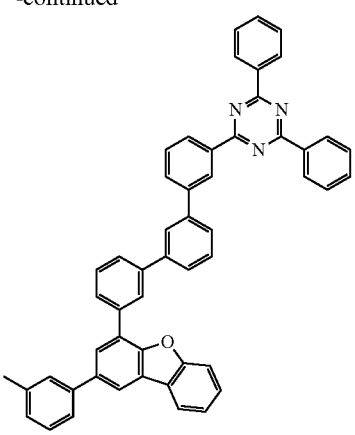
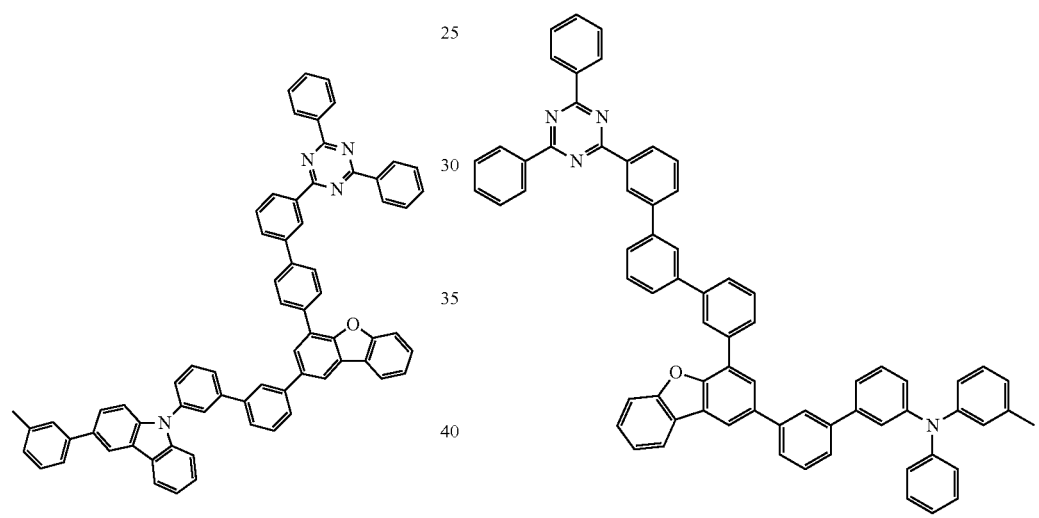
2-13
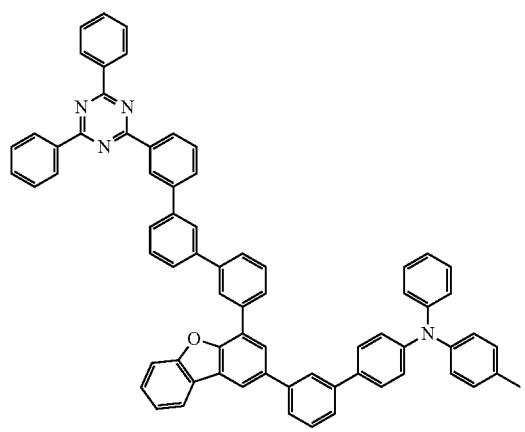
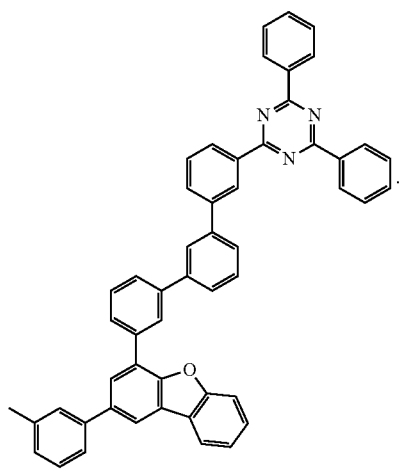

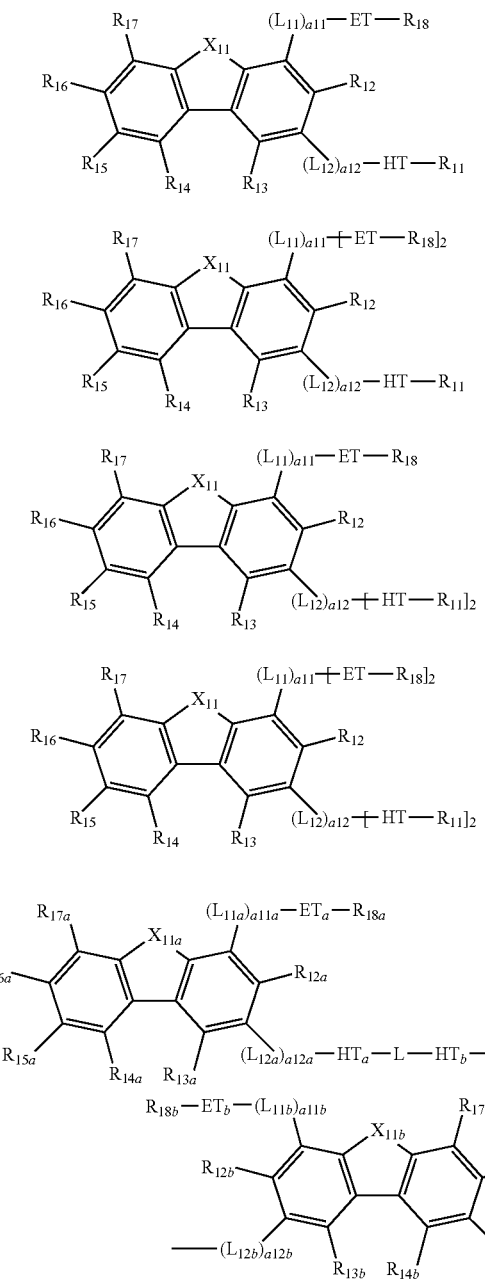

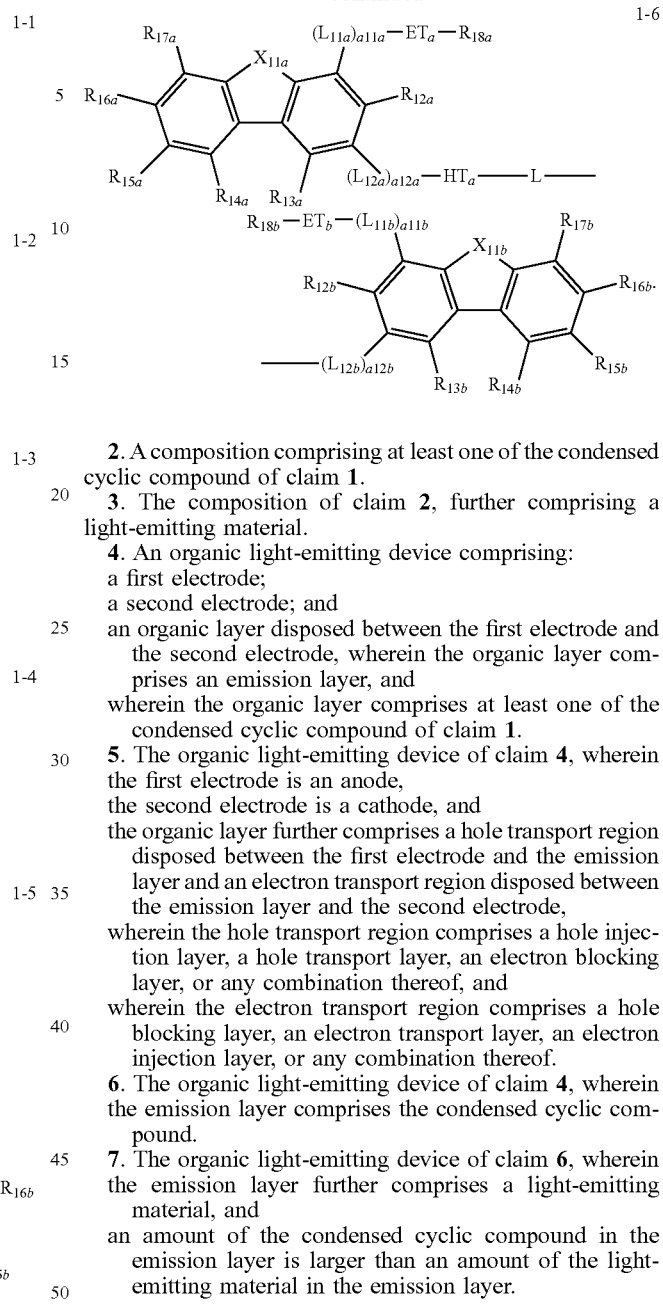

2. A composition comprising at least one of the condensed cyclic compound of claim 1.

3. The composition of claim 2, further comprising a light-emitting material.

4. An organic light-emitting device comprising:
a first electrode;
a second electrode; and
an organic layer disposed between the first electrode and the second electrode, wherein the organic layer comprises an emission layer, and
wherein the organic layer comprises at least one of the condensed cyclic compound of claim 1.

5. The organic light-emitting device of claim 4, wherein the first electrode is an anode,
the second electrode is a cathode, and
the organic layer further comprises a hole transport region disposed between the first electrode and the emission layer and an electron transport region disposed between the emission layer and the second electrode,
wherein the hole transport region comprises a hole injection layer, a hole transport layer, an electron blocking layer, or any combination thereof, and
wherein the electron transport region comprises a hole blocking layer, an electron transport layer, an electron injection layer, or any combination thereof.

6. The organic light-emitting device of claim 4, wherein the emission layer comprises the condensed cyclic compound.

7. The organic light-emitting device of claim 6, wherein the emission layer further comprises a light-emitting material, and
an amount of the condensed cyclic compound in the emission layer is larger than an amount of the light-emitting material in the emission layer.

* * * * *